(12) United States Patent
Quake et al.

(10) Patent No.: US 10,196,689 B2
(45) Date of Patent: *Feb. 5, 2019

(54) MEASUREMENT AND COMPARISON OF IMMUNE DIVERSITY BY HIGH-THROUGHPUT SEQUENCING

(71) Applicant: The Board of Trustees of the Leland Stanford Junior University, Stanford, CA (US)

(72) Inventors: Stephen R. Quake, Stanford, CA (US); Joshua Weinstein, Stanford, CA (US); Ning Jiang, Austin, TX (US); Daniel S. Fisher, Los Altos, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 261 days.

This patent is subject to a terminal disclaimer.

(21) Appl. No.: 15/040,887

(22) Filed: Feb. 10, 2016

(65) Prior Publication Data

US 2016/0333405 A1    Nov. 17, 2016

Related U.S. Application Data

(63) Continuation of application No. 14/735,066, filed on Jun. 9, 2015, now Pat. No. 9,290,811, which is a (Continued)

(51) Int. Cl.
*C40B 50/06* (2006.01)
*C12Q 1/6876* (2018.01)
(Continued)

(52) U.S. Cl.
CPC ......... *C12Q 1/6876* (2013.01); *C12Q 1/6809* (2013.01); *C12Q 1/6883* (2013.01);
(Continued)

(58) Field of Classification Search
None
See application file for complete search history.

(56) References Cited

U.S. PATENT DOCUMENTS 5,750,341 A    5/1998 Macevicz
5,969,119 A    10/1999 Macevicz
(Continued)

FOREIGN PATENT DOCUMENTS

EP    1544308 B1    6/2005
EP    2364368 B1    1/2014
(Continued)

OTHER PUBLICATIONS

Lim et al. (Jul. 15, 2007) The Journal of Allergy and Clinical Immunology vol. 120 pp. 696 to 706.*
(Continued)

*Primary Examiner* — Christian C Boesen
(74) *Attorney, Agent, or Firm* — Pamela J. Sherwood; Bozicevic, Field & Francis LLP

(57) ABSTRACT

A precise measurement of the immunological receptor diversity present in a sample is obtained by sequence analysis. Samples of interest are generally complex, comprising more than $10^2$, $10^3$, $10^4$, $10^5$, $10^6$, $10^7$, $10^8$, $10^9$, $10^{10}$, $10^{11}$, $10^{12}$ or more different sequences for a receptor of interest. Immunological receptors of interest include immunoglobulins, T cell antigen receptors, and major histocompatibility receptors. The specific composition of immunological receptor sequence variations in the sample can be recorded and output. The composition is useful for predictive, diagnostic and therapeutic methods relating to the immune capabilities and history of an individual. Such predictions and diagnoses are used to guide clinical decisions.

13 Claims, 16 Drawing Sheets
(14 of 16 Drawing Sheet(s) Filed in Color)
Specification includes a Sequence Listing.

Related U.S. Application Data continuation of application No. 13/696,375, filed as application No. PCT/US2011/035507 on May 6, 2011, now Pat. No. 9,234,240.

(60) Provisional application No. 61/395,116, filed on May 7, 2010.

(51) Int. Cl.

| | | |
|---|---|---|
| *C12Q 1/6883* | (2018.01) | |
| *C12Q 1/6809* | (2018.01) | |
| *G06F 19/18* | (2011.01) | |
| *G06F 19/22* | (2011.01) | |
| *C12Q 1/6886* | (2018.01) | |
| *C12Q 1/6874* | (2018.01) | |

(52) U.S. Cl.
CPC .......... *C12Q 1/6886* (2013.01); *G06F 19/18* (2013.01); *G06F 19/22* (2013.01); *C12Q 1/6874* (2013.01); *C12Q 2600/106* (2013.01); *C12Q 2600/118* (2013.01); *C12Q 2600/124* (2013.01); *C12Q 2600/156* (2013.01); *C12Q 2600/16* (2013.01); *C40B 50/06* (2013.01)

(56) References Cited

U.S. PATENT DOCUMENTS

| | | | |
|---|---|---|---|
| 5,994,076 | A | 11/1999 | Chenchik et al. |
| 6,306,597 | B1 | 10/2001 | Macevicz |
| 7,170,050 | B2 | 1/2007 | Turner et al. |
| 7,211,390 | B2 | 5/2007 | Rothberg et al. |
| 7,244,559 | B2 | 7/2007 | Rothberg et al. |
| 7,244,567 | B2 | 7/2007 | Chen et al. |
| 7,264,929 | B2 | 9/2007 | Rothberg et al. |
| 7,276,720 | B2 | 10/2007 | Ulmer |
| 7,302,146 | B2 | 11/2007 | Turner et al. |
| 7,313,308 | B2 | 12/2007 | Turner et al. |
| 7,315,019 | B2 | 1/2008 | Turner et al. |
| 7,323,305 | B2 | 1/2008 | Leamon et al. |
| 7,335,762 | B2 | 2/2008 | Rothberg et al. |
| 7,405,281 | B2 | 7/2008 | Xu et al. |
| 7,462,452 | B2 | 12/2008 | Williams et al. |
| 7,462,468 | B1 | 12/2008 | Williams et al. |
| 7,476,503 | B2 | 1/2009 | Turner et al. |
| 7,476,504 | B2 | 1/2009 | Turner |
| 7,491,498 | B2 | 2/2009 | Lapidus et al. |
| 7,501,245 | B2 | 3/2009 | Quake et al. |
| 7,785,783 | B2 | 8/2010 | Morley et al. |
| 8,236,503 | B2 | 8/2012 | Faham et al. |
| 8,507,205 | B2 | 8/2013 | Faham et al. |
| 8,628,927 | B2 | 1/2014 | Faham et al. |
| 8,691,510 | B2 | 4/2014 | Faham et al. |
| 8,748,103 | B2 | 6/2014 | Faham et al. |
| 8,795,970 | B2 | 8/2014 | Faham et al. |
| 9,909,180 | B2 | 3/2018 | Quake et al. |
| 2006/0024678 | A1 | 2/2006 | Buzby |
| 2006/0024711 | A1 | 2/2006 | Lapidus et al. |
| 2006/0046258 | A1 | 3/2006 | Lapidus et al. |
| 2006/0259248 | A1 | 11/2006 | Collette et al. |
| 2006/0286566 | A1 | 12/2006 | Lapidus et al. |
| 2007/0072240 | A1 | 3/2007 | Brekke et al. |
| 2007/0161001 | A1 | 7/2007 | Leshkowitz |
| 2008/0087826 | A1 | 4/2008 | Harris et al. |
| 2008/0103058 | A1 | 5/2008 | Siddiqi |
| 2008/0166718 | A1 | 7/2008 | Lim et al. |
| 2008/0206764 | A1 | 8/2008 | Williams et al. |
| 2008/0213770 | A1 | 9/2008 | Williams et al. |
| 2009/0024331 | A1 | 1/2009 | Tomaney et al. |
| 2009/0029385 | A1 | 1/2009 | Christians et al. |
| 2009/0068655 | A1 | 3/2009 | Williams |
| 2011/0207134 | A1 | 8/2011 | Faham et al. |
| 2011/0207135 | A1 | 8/2011 | Faham et al. |
| 2011/0207617 | A1 | 8/2011 | Faham et al. |
| 2012/0058902 | A1 | 3/2012 | Livingston et al. |
| 2012/0183969 | A1 | 7/2012 | Han |
| 2013/0065768 | A1 | 3/2013 | Zheng et al. |
| 2013/0150252 | A1 | 6/2013 | Faham et al. |
| 2013/0196328 | A1 | 8/2013 | Pepin et al. |
| 2013/0202718 | A1 | 8/2013 | Pepin et al. |
| 2013/0236895 | A1 | 9/2013 | Faham et al. |
| 2013/0324422 | A1 | 12/2013 | Faham et al. |
| 2014/0255929 | A1 | 9/2014 | Zheng |
| 2014/0255944 | A1 | 9/2014 | Carlton et al. |
| 2014/0315725 | A1 | 10/2014 | Faham et al. |

FOREIGN PATENT DOCUMENTS

| | | |
|---|---|---|
| WO | 2003/044225 A2 | 5/2003 |
| WO | 2008/147879 A1 | 12/2008 |
| WO | 2009/137255 A2 | 11/2009 |
| WO | 2010/053587 A2 | 5/2010 |
| WO | 2011/140433 A2 | 11/2011 |

OTHER PUBLICATIONS

White et al., "Digital PCR provides sensitive and absolute calibration for high throughput sequencing." BMC Genomics, Mar. 19, 2009, pp. pp. 1-12, 10:116, BioMed Central, London, United Kingdom.

Delassus et al. "PCR-based analysis of the murine immunoglobulin heavy-chain repertoire," Journal of Immunological Methods, Aug. 18, 1995, pp. 219-229, vol. 184, No. 2, Elsevier, Amsterdam, Netherlands.

Holtmeier et al. "IgA and IgM V(H) repertoires in human colon: evidence for clonally expanded B cells that are widely disseminated," Gastroenterology, Nov. 2000, pp. 1253-1266, vol. 119, No. 5, American Gastroenterological Association, Bethesda, MD.

White, "Restriction-PCR fingerprinting of the immunoglobulin VH repertoire: direct detection of an immune response and global analysis of B cell clonality," European Journal of Immunology, Oct. 1998, pp. 3268-3279, vol. 28, No. 10, Wiley, Hoboken, NJ.

Wu et al., "High-throughput immunoglobulin repertoire analysis distinguishes between human IgM memory and switched memory B-cell populations," Blood, Aug. 19, 2010, pp. 1070-1078, vol. 116, No. 7, American Society of Hematology, Washington, D.C.

Altin et al., "The role of CD45 and CD-45 associated molecules in T cell activation," Immunol. Cell Bioi., Jun. 2, 1997, pp. 430-445, vol. 75, No. 5, Nature Publishing Group, New York, NY.

Arnaout, "Specificity and overlap in gene segment-defined antibody," BMC Genomics, Oct. 28, 2005, pp. 1-9, vol. 28, No. 6, BioMed Central, London, United Kingdom.

Campbell et al., "Subclonal phylogenetic structures in cancer revealed by ultra-deep sequencing," PNAS, Sep. 2, 2008, pp. 13081-13086. vol. 105 No. 35, PNAS, Washington, DC.

Curran et al., "Nucleotide Sequencing of Psoriatic Arthritis Tissue before and during Methotrexate Administration Reveals a Complex Inflammatory T Cell Infiltrate with Very Few Clones Exhibiting Features That Suggest They Drive the Inflammatory Process by Recognizing Autoantigens," The Journal of Immunology, (2004), pp. pp. 1935-1944, vol. 172, No. 3, American Association of immunologists, Inc., Rockville, Maryland.

Damle et al., "B-cell chronic lymphocytic leukemia cells express a surface membrane phenotype of activated, antigen-experienced Blymphocytes," Blood, (2002), pp. 4087-4093, vol. 99, No. 11, American Society of Hematology, Washington, D.C.

Diluvio et al., "Identical TCR beta-chain rearrangements in streptococcal angina and skin lesions of patients with psoriasis vulgaris" J. Immunol. (2006), pp. 7104-11, vol. 176, No. 11, American Association of Immunologists, Inc., Rockville, Maryland.

Dressman et al., "Transforming single DNA molecules into fluorescent magnetic particles for detection and enumeration of genetic variations," PNAS, (2003), pp. 8817-8822, vol. 100. No. 15, PNAS, Washington, DC.

Freeman et al., "Profiling the Tcell receptor beta-chain repertoire by massively parallel sequencing," Genome Research, (2009, published online Jun. 18, 2009), pp. 1817-1824, vol. 19, Cold Spring Harbor Lab Press, Woodbury, NY.

(56) References Cited

OTHER PUBLICATIONS

Furmanski et al., "Public T cell receptor beta-chains are not advantaged during positive selection," J Immunol., (Jan. 2008), pp. 1029-1039, vol. 180, American Association of Immunologists, Inc., Rockville, Maryland.
Glanville et al., "Precise determination of the diversity of a combinatorial antibody library gives insight into the human immunoglobulin repertoire," Dec. 1, 2009, published online Oct. 29, 2009, PNAS, pp. 20216-20221, vol. 106, No. 48, PNAS, Washington, DC.
Han et al., "Immunorepertoire analysis by multiplex PCR amplification and high throughput sequencing," (Abstract) J. Immunol., 2009, Meeting Abstract Supplement, pp. 1-2, 42.6, American Association of Immunologists, Inc., Rockville, Maryland.
Heyer et al., "Exploring Expression Data: Identification and Analysis of Coexpressed Genes" Genome Res. (1999), pp. 1106-1115, vol. 9, Cold Spring Harbor Lab Press, Woodbury, NY.
Kita et al., "T Cell Receptor Clonotypes in Skin Lesions from Patients with Systemic Lupus Erythematosus," The Journal of Investigative Dermatology, Sep. 12, 1997, p. 41-46.vol. 110, Society for Investigative Dermatology, Cleveland, OH.
Mardis, "Next-generation DNA sequencing methods," Annu. Rev. Genomics Hum. Genet., Sep. 2008, published online Jun. 2008, pp. 387-402, vol. 9, Annual Reviews, Palo Alto, CA.
Miceli et al., "The roles of CD4 and CD8 in T cell activation," Semin. Immunol., May 3, 1991, pp. 133-141 (abstract only),pp. 1-2, vol. 3, No. 3, PubMed—NCBI, Bethesda, MD.
Robins et al., "Comprehensive assessment of T-cell receptor beta-chain diversity in a-beta T cells," Blood, Nov. 5, 2009, published online Aug. 2009,pp. 4099-4107, vol. 114, No. 19, American Society of Hematology, Washington, D.C.
Shendure et al., "Next-generation DNA sequencing," Nature Biotechnology, Oct. 9, 2008, pp. 1135-1145, vol. 26, Nature Biotechnology, New York, NY.
Shendure et al., "Advanced Sequencing Technologies: Methods and Goals," Nat. Rev. Genet., May 2004, pp. 335-344, vol. 5, No. 5, Nature Publishing Group, New York, NY.
Skulina et al.,"Multiple sclerosis: Brain-infiltrating CD8+ T cells persist as clonal expansions in the cerebrospinal fluid and blood," PNAS, 2004, published online Feb. 24, 2004, pp. pp. 2428-2433, vol. 100, No. 8, PNAS, Washington, DC.
Stanley, "Chapter 7, T Cells," Essentials of Immunology & Serology, Delmar, Thomson Learning, (2002), p. 95., Cengage Learning, Inc., Boston, MA.
Striebich et al., "Selective Accumulation of Related CD4+ T Cell Clones in the Synovial Fluid of Patients with Rheumatoid Arthritis," J. Imm., Oct. 15, 1998, pp. 4428-4436, vol. 161, American Association of Immunologists, Inc., Rockville, Maryland.
Universite De Liege, "Roche 454 FLX Technology: how it works," located at http://www.giga.ulg.ac.be/jcms/cdu_15721/fr/roche-454-flx-technology-how-it-works, Oct. 10, 2014, 2 pages.
Vanderborght et al., "Dynamic T cell receptor clonotype changes in synovial tissue of patients with early rheumatoid arthritis: effects of treatment with cyclosporin A (Neoral)," J. Rheumatol., (2002) pp. 416-426, vol. 29, No. 3, Journal of Rheumatology, Toronto, ON, Canada.
Wang et al., "HIV integration site selection: Analysis by massively parallel pyrosequencing reveals association with epigenetic modifications," Genome Res., Jun. 1, 2007, pp. 1186-1194, vol. 17, No. 8, Cold Spring Harbor Lab Press, Woodbury, NY.
Wang et al., "Immunorepertoire analysis by multiplex PCR amplification and high throughput sequencing," (Poster-Program 42.6), The 96th Annual Meeting of the American Association of Immunologists, Seattle, Washington, May 8-12, 2009.
Wang et al., (Jan. 26, 2010). "High throughput sequencing reveals a complex pattern of dynamic interrelationships among human T cell subsets," PNAS, pp. 1518-1523.vol. 107, No. 4, PNAS, Washington, DC.
Warren et al., "Profiling model T-cell metagenomes with short reads," Bioinformatics, Jan. 1, 2009, pp. 458-464, vol. 25, No. 4, Oxford University Press, Oxford, United Kingdom.
Warren et al., "Exhaustive Tcell repertoire sequencing of human peripheral blood samples reveals signatures of antigen selection and a directly measured repertoire size of at least 1 million clonotyptes," Genome Research, (2011, published online Feb. 24, 2011 ), pp. 790-797, vol. 27, Cold Spring Harbor Lab Press, Woodbury, NY.
Weinstein et al. "Supporting Online Material for 'High-throughput sequencing of the zebrafish antibody repertoire'," Science, May 8, 2009, pp. 1-20, vol. 324, available at www.sciencemag.org/cgi/content/fuii/324/5928/807/DC1.
Ademokun et al., "Vaccination-introduced changes in human B-cell repertoire and pneumococcalIgM and IgA antibody at different ages", Aging Cell, Jun. 29, 2011, pp. 922-930, 10(6), Blackwell Publishing, Hoboken, NJ.
Michaeli et al., "Automated cleaning and pre-processing of immunoglobulin gene sequences from high-throughput sequencing", Frontiers in Immunology, Dec. 2012, pp. 1-16, vol. 3, Article 386, Frontiers in Immunology. Lausanne Switzerland.
Boyd et al., Measurement of Human Lymphocyte Clonality by Massively Parallel VDJ Pyrosequencing, Science Translational Medicine, Dec. 23, 2009, pp. 1-30, vol. 1, No. 12., NIH, Bethesda, Maryland.
Weinstein et al. "High-throughput sequencing of the zebrafish antibody repertoire", Science, May 2009, pp. 807-810, vol. 324, Science, Cambridge, UK.
Lim et al., "The IgE repertoire in PBMCs of atopic patients is characterized by individual rearrangements without variable region of the heavy immunoglobulin chain bias", J Allergy Clin Immunol, Jul. 15, 2007,pp. 696-706, 120(3),. American Academy of Allergy, Asthma & Immunology, Milwaukee, WI.
ATCC, "Jurkat, Clone E6-1(ATCC TIB-152)," located at http://www.atcc.org/Products/All/TIB-152.aspx#characteristics, Jun. 5, 2015, 1 page, American Type Culture Collection (ATCC), Manassas, VA.
Boxall IPM Ltd., Opposition of EP Patent No. 2364368B filed on Oct. 14, 2014, 24 pages.
Muller, Opposition of EP Patent No. 2364368B filed on Oct. 14, 2014 44 pages.
U.S. Appl. No. 61/045,586, filed Apr. 16, 2008 by Jian Han, 39 pages.
Boudinot et al., "New perspectives for large-scale repertoire analysis of immune receptors," Mol. Immunol., May 2008, pp. 2437-2445, 45, Elsevier, Amsterdam, Netherlands.
Bunge et al., "Estimating the Number of Species: A Review," J. Am. Stat. Assoc., Mar. 1993, pp. 364-373, vol. 38, No. 421, American Statistical Association, Alexandria, VA.
Danilova et al., "Immunoglobulin variable-region diversity in the zebrafish," Immunogenetics, Nov. 2000, pp. 81-91, 52, Springer, New York City, NY.
Danilova et al., "The immunoglobulin heavy-chain locus in zebrafish: identification and expression of a previously unknown isotype, immunoglobulin Z.," Nat. Immunol., Mar. 2005, pp. 295-302, vol. 6, No. 3, Nature Immunology, New York, NY.
Golub, "Somatic mutation: diversity and regulation of the immune repertoire," Cell, Mar. 13, 1987, pp. 723-724, 48, Cell Press, Cambridge, MA.
Huising et al., "Increased efficacy of immersion vaccination in fish with hyperosmotic pretreatment," Vaccine, Jun. 2003, pp. 4178-4193,21, Elsevier, Amsterdam, Netherlands.
Jones et al., "The taming of a transposon: V(D)J recombination and the immune system," Immunol. Rev., Jul. 9, 2004, pp. 233-248, 200, Blackwell Munksgaard, Oxford, United Kingdom.
Krovel el al., "Sexual dimorphic expression pattern of a splice variant of zebrafish vasa during gonadal development," Dev Bioi., 2004, pp. 190-197, 271(1), Elsevier, Amsterdam, Netherlands.
Langenau et al., "Myc-Induced T Cell Leukemia in Transgenic Zebrafish," Science, Feb. 7, 2003, pp. 887-890, vol. 299, Science, Washington, DC.
Litman et al., "Reconstructing immune phylogeny: new perspectives," Nat. Rev. Immunol., Nov. 2005, 866-879, vol. 5, Nature Publishing Group, London, United Kingdom.
Maizels, "Immunoglobulin Gene Diversification," Annu. Revu., Genet. Jun. 21, 2005, pp. 23-46, 39, Annual Reviews, Palo Alto, CA.

(56) References Cited

OTHER PUBLICATIONS

Margulies et al., "Genome sequencing in microfabricated high-density picolitre reactors," Nature, Sep. 15, 2005, pp. 376-380, 437, Nature Publishing Group, London, United Kingdom.

Murtha et al., "Hematologic and serum biochemical values for zebrafish (*Dania rerio*)," Camp Med, Feb. 2003, pp. 37-41, vol. 53, No. 1, American Association for Laboratory Animal Science, Memphis, TN.

Peet, "The Measurement of Species Diversity," Annu Rev. Ecol. Syst. 1974, pp. 285-307, vol. 5, Annual Reviews, Palo Alto, CA.

Rock et al., "CDR3 Length in Antigen-specific Immune Receptors," J. Exp. Med., Jan. 1, 1994, pp. 323-328, vol. 179, Rockefeller University Press, New York, NY.

Ronaghi et al., "Real-Time DNA Sequencing Using Detection of Pyrophosphate Release," Analytical Biochemistry, May 6, 1996, pp. 84-89, 242, Academic Press, Inc., Cambridge, MA.

Ronaghi et al., "A Sequencing Method Based on Real-Time Pyrophosphate," Science, Jul. 17, 1998, pp. 363-365, 281, Science, Washington, DC.

Smith et al., "Identification of common molecular subsequences," J Mol Biol., Mar. 1981, pp. 195-197, 147(1), Elsevier, Amsterdam, Netherlands.

Talmage, "Unique combinations of selected natural globulins provide an alternative to the classical concept," Science, Jun. 19, 1959, pp. 1643-1648, vol. 129, No. 3364, American Association for the Advancement of Science, Washington, D.C.

Tibshirani et al., "Diagnosis of multiple cancer types by shrunken centroids of gene expression," PNAS, May 14, 2002, pp. 6567-6572, vol. 99, No. 10, PNAS, Washington, DC.

Traver et al., "Transplantation and in vivo imaging of multilineage engraftment in zebrafish bloodless mutants," Nat Immunol, Nov. 9, 2003. pp. 1238-1246, vol. 4, No. 12, Nature Immunology, New York NY.

Trede et al., "The Use of Zebrafish to Understand Immunity," Immunity, Apr. 2004, pp. 367-379, vol. 20, Cell Press,Cambridge, MA.

Tusher et al., "Significance analysis of microarrays applied to the ionizing radiation response," PNAS, Apr. 24, 2001, pp. 5118-5121, 98, PNAS, Washington, DC.

Winter et al., "Dual enigma of somatic hypermutation of immunoglobulin variable genes: targeting and mechanism," Immunol. Rev., Apr. 1998, pp. 89-96, 162, Wiley, Hoboken, NJ.

Xu et al., "Diversity in the CDR3 Region of VH Is Sufficient for Most Antibody Specificities," Immunity, Jul. 2000, pp. 37-45, vol. 13, Cell Press, Cambridge, MA.

Yoder et al., "Zebrafish as an immunological model system," Microbes Infect., Nov. 2002, 1469-1478, 4, Elsevier, Amsterdam, Netherlands.

Jiang et al., "Determinism and stochasticity during maturation of the zebrafish antibody repertoire," PNAS, Mar. 29, 2011, pp. 5348-5353, vol. 108, No. 3, PNAS, Washington, DC.

\* cited by examiner

Fig. 1A
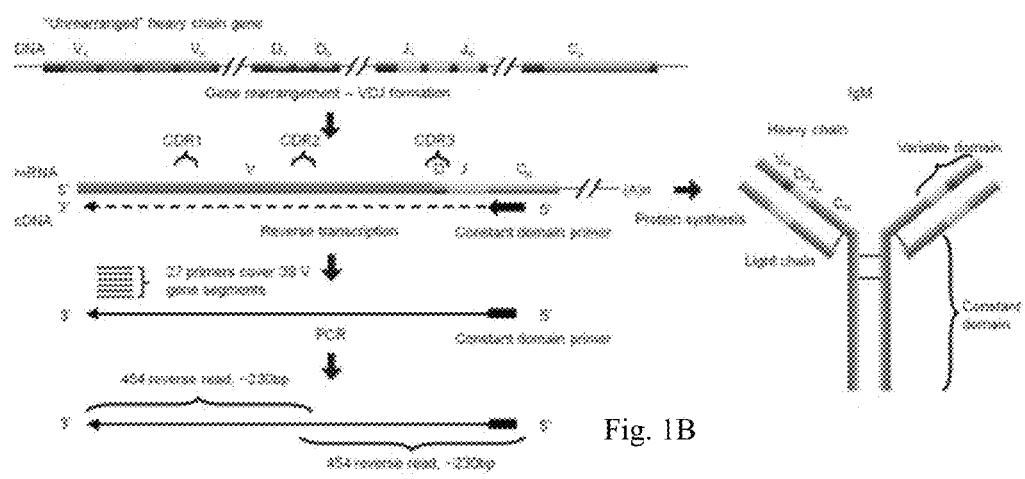
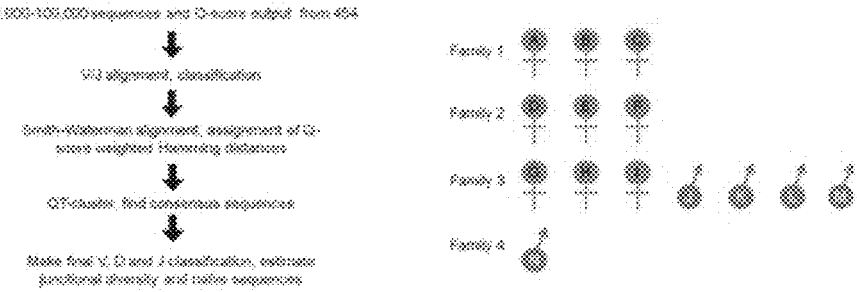
Fig. 1B

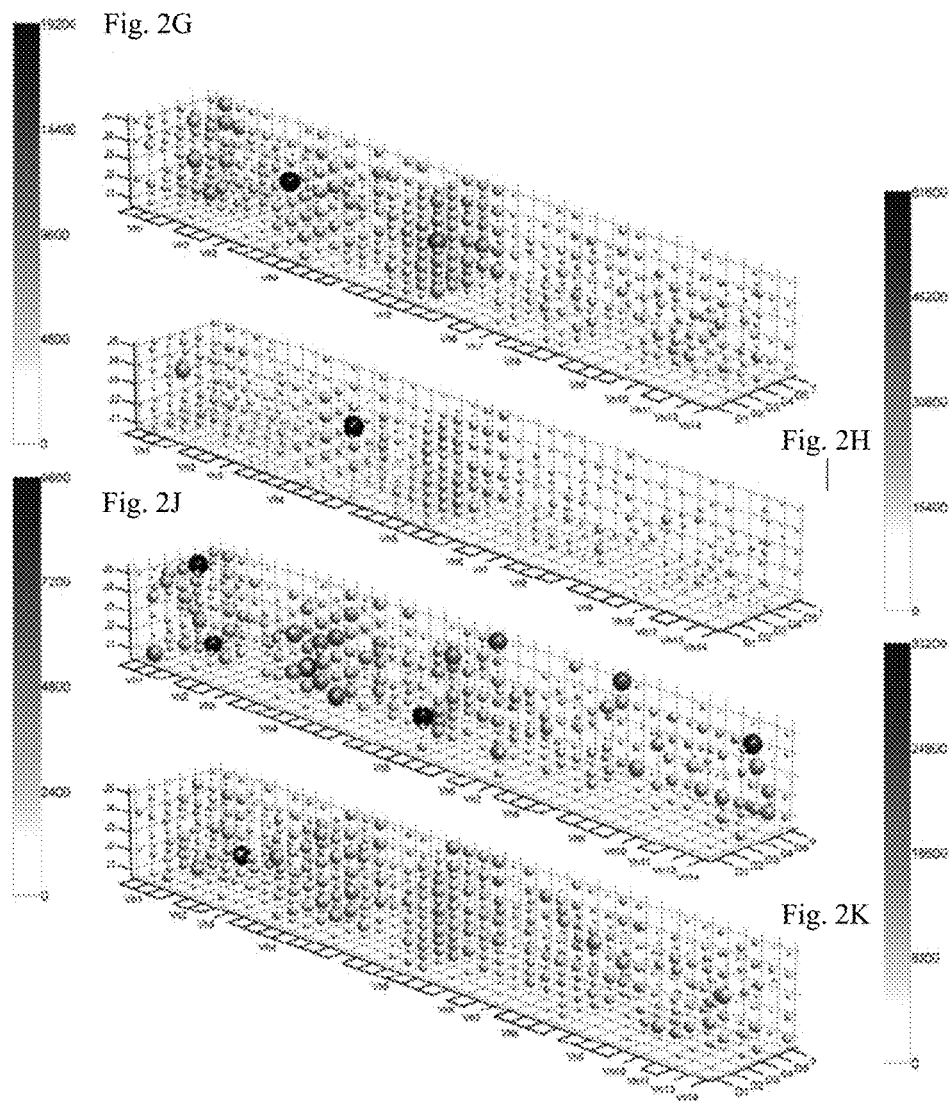

Fig. 3A
Fig. 3B
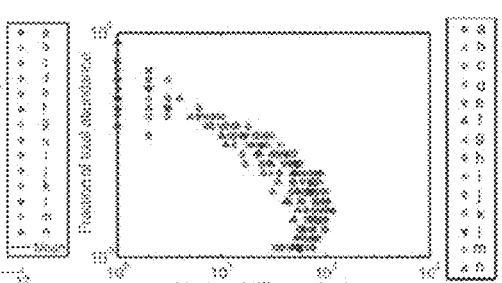
Fig. 3C
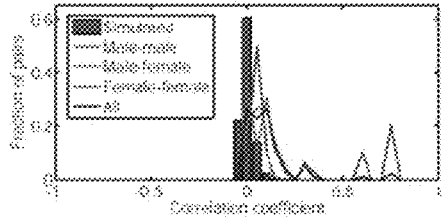
Fig. 3D
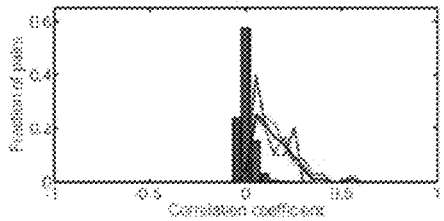
Fig. 4A
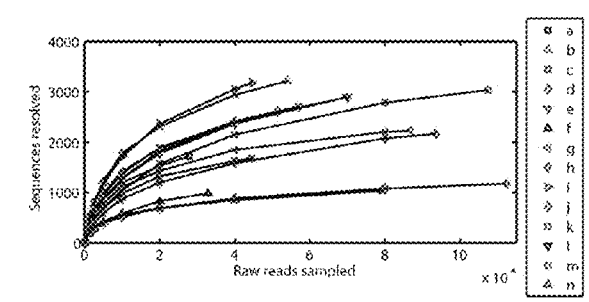
Fig. 4B
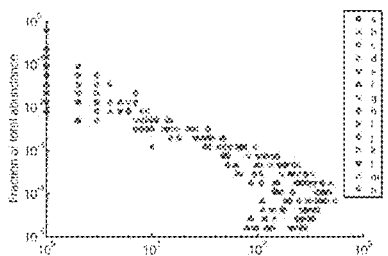
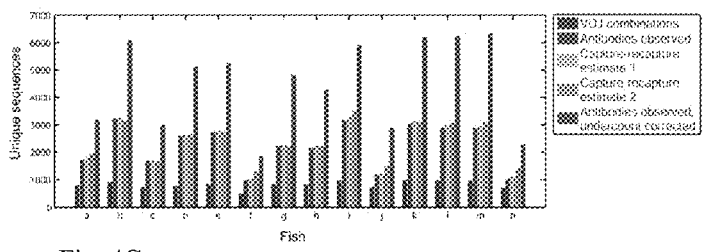
Fig. 4C
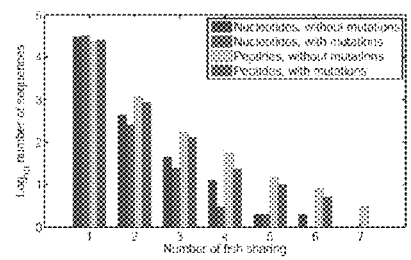
Fig. 4D Fig. 15A
Fig. 15B
Fig. 15C
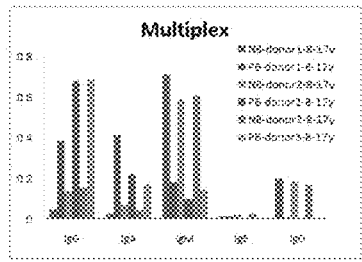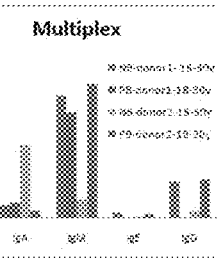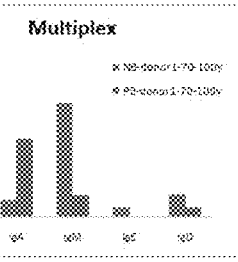
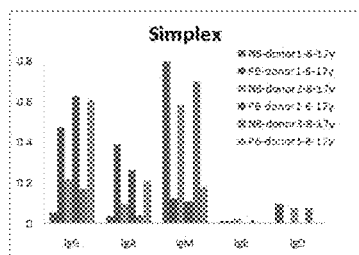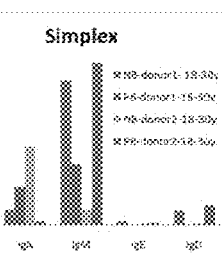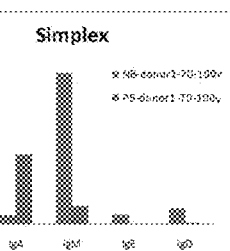
Fig. 15D
Fig. 15E
Fig. 15F
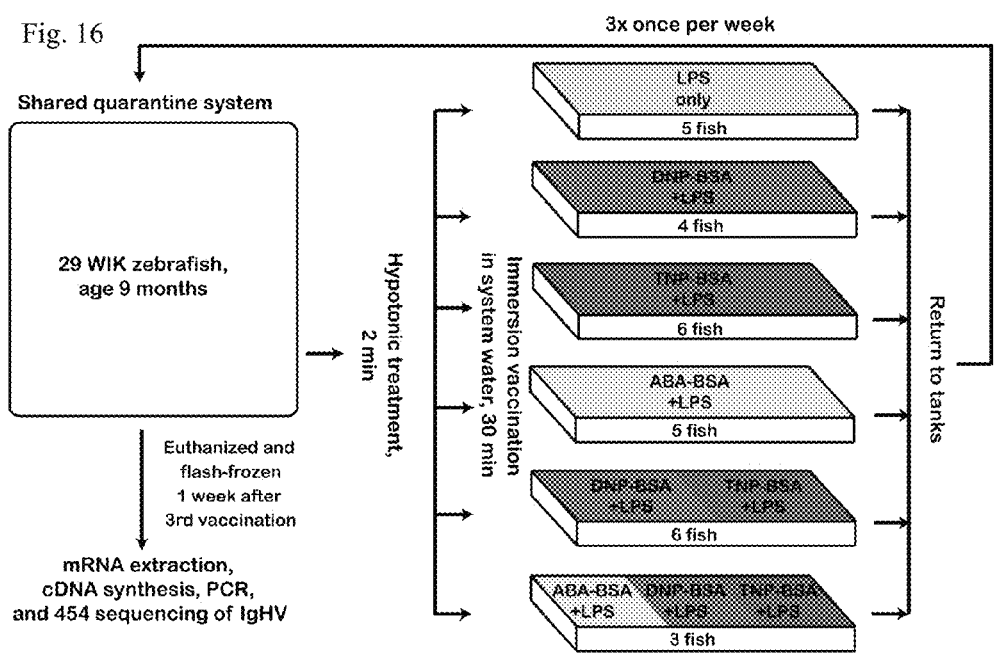

Fig. 23

| | Female | Male | Family 1 | Family 2 | Family 3 | Family 4 |
|---|---|---|---|---|---|---|

| Fish | | | | | | | | | | | | | | |
|---|---|---|---|---|---|---|---|---|---|---|---|---|---|---|
| Total IgM reads | 27851 | 54148 | 44591 | 51471 | 57252 | 33863 | 87255 | 94238 | 45156 | 112833 | 108053 | 70133 | 70228 | 79781 |
| Identifiable VJm | 27829 | 54041 | 44480 | 51391 | 57187 | 32803 | 86639 | 93563 | 44638 | 112450 | 107540 | 68964 | 70103 | 79118 |
| Identifiable VDmJm | 18059 | 40241 | 38351 | 36012 | 33887 | 29138 | 64675 | 84228 | 30148 | 67943 | 42444 | 36062 | 41150 | 63621 |
| VJm coverage | 0.9333 | 0.9438 | 0.3528 | 0.9333 | 0.5231 | 0.7538 | 0.9385 | 0.9333 | 0.9897 | 0.969 | 1 | 0.9795 | 0.9697 | 0.9841 |
| VDmJm coverage | 0.678 | 0.7239 | 0.6174 | 0.7008 | 0.7458 | 0.5905 | 0.758 | 0.7487 | 0.8215 | 0.6584 | 0.9628 | 0.84 | 0.8133 | 0.8194 |
| 0-bp reads/cluster | 2.5078 | 2.4945 | 2.7577 | 2.2923 | 3.0693 | 3.1285 | 3.3735 | 4.2242 | 2.3069 | 4.988 | 3.4463 | 2.7593 | 2.46 | 4.7944 |
| 3-bp reads/cluster | 9.0786 | 6.6853 | 14.896 | 8.3870 | 10.627 | 14.441 | 15.594 | 20.286 | 7.5954 | 35.304 | 19.277 | 13.541 | 10.51 | 32.354 |
| Total IgZ reads | 722 | 490 | 767 | 562 | 1527 | 647 | 6729 | 3622 | 5351 | 2061 | 13123 | 6612 | 9678 | 4179 |
| Identifiable VJz | 718 | 480 | 723 | 497 | 1495 | 609 | 6427 | 3188 | 5035 | 1938 | 12768 | 6368 | 9613 | 3975 |
| Identifiable VDzJz | 540 | 272 | 338 | 319 | 717 | 618 | 4709 | 1968 | 2790 | 891 | 9354 | 5022 | 4819 | 3621 |
| VJz coverage | 0.7951 | 0.7982 | 0.7821 | 0.6735 | 0.6103 | 0.2949 | 0.9358 | 0.8856 | 0.9744 | 0.9231 | 0.9615 | 0.9744 | 0.9615 | 0.8846 |
| VDzJz coverage | 0.3654 | 0.5064 | 0.4615 | 0.391 | 0.7951 | 0.141 | 0.8387 | 0.7628 | 0.6187 | 0.6719 | 0.8187 | 0.8846 | 0.891 | 0.8795 |
| 0-bp reads/cluster | 3.0112 | 1.3783 | 1.8166 | 1.5032 | 1.4515 | 3.657 | 1.9595 | 1.7536 | 1.4542 | 1.9495 | 2.7323 | 1.8509 | 1.9554 | 3.3431 |
| 3-bp reads/cluster | 4.8494 | 2.1718 | 3.2422 | 2.605 | 2.6637 | 14.285 | 5.314 | 4.4094 | 3.6143 | 4.3549 | 8.7836 | 4.3413 | 5.4824 | 10.135 |
| IgM:IgZ ratio | 51.535 | 198.88 | 131.0 | 181.1 | 78.759 | 53.261 | 18.282 | 47.837 | 15.999 | 162.74 | 11.467 | 21.714 | 15.178 | 48.808 |

| | Female | Male | Family 1 | Family 2 | Family 3 | Family 4 |
|---|---|---|---|---|---|---|

| | | | | | | | | | | | |
|---|---|---|---|---|---|---|---|---|---|---|---|
| | 0 | | | | | | | | | | |
| | 0.003 | 0 | | | | | | | | | |
| | 0 | 0.003 | | | | | | | | | |
| | 0 | 0.003 | 0 | 0.007 | | | | | | | |
| | 0 | 0 | 0 | 0.1 | 0 | | | | | | |
| | 0 | 0.013 | 0 | 0 | 0.033 | 0 | | | | | |
| | 0 | 0.037 | 0 | 0 | 0.017 | 0 | 0.02 | | | | |
| | 0 | 0.003 | 0.097 | 0 | 0.098 | 0 | 0.017 | 0.007 | | | |
| | 0 | 0.01 | 0 | 0 | 0.04 | 0 | 0.007 | 0.01 | 0.007 | | |
| | 0 | 0.04 | 0 | 0 | 0.954 | 0 | 0.026 | 0.003 | 1.669 | 0.01 | |
| | 0 | 0 | 0 | 0.003 | 0 | 0 | 0 | 0 | 0 | 0.003 | |
| | 0 | 0 | 0 | 0.003 | 0.003 | 0 | 0 | 0 | 0 | 0.003 | 4.415 |
| | 0 | 0.017 | 0 | 0 | 0.003 | 0 | 0.003 | 0.01 | 0.003 | 0 | 0.007 | 0 | 0 |

Fig. 25B

| | | | | | | | | | | | |
|---|---|---|---|---|---|---|---|---|---|---|---|
| | 0 | | | | | | | | | | |
| | 0 | 0 | | | | | | | | | |
| | 0 | 0 | 1 | | | | | | | | |
| | 0 | 1 | 0 | 0 | | | | | | | |
| | 0 | 0 | 0 | 10 | 0 | | | | | | |
| | 0 | 2 | 0 | 0 | 7 | 0 | | | | | |
| | 0 | 1 | 0 | 0 | 4 | 0 | 0 | | | | |
| | 0 | 0 | 0 | 0 | 1 | 0 | 4 | 1 | | | |
| | 0 | 2 | 0 | 0 | 3 | 0 | 2 | 3 | 2 | | |
| | 0 | 3 | 0 | 0 | 0 | 0 | 2 | 0 | 1 | 1 | |
| | 0 | 0 | 0 | 0 | 0 | 0 | 0 | 0 | 0 | 0 | |
| | 0 | 0 | 0 | 0 | 0 | 0 | 0 | 0 | 0 | 0 | 0 |
| | 0 | 3 | 0 | 0 | 0 | 0 | 2 | 1 | 0 | 0 | 0 | 0 |

Fig. 25C

| | | | | | | | | | | | |
|---|---|---|---|---|---|---|---|---|---|---|---|
| | 0 | | | | | | | | | | |
| | 0 | 0 | | | | | | | | | |
| | 0 | 0 | 2.478 | | | | | | | | |
| | 0 | 2.478 | 0 | 0 | | | | | | | |
| | 0 | 0 | 0 | 15.81 | 0 | | | | | | |
| | 0 | 4.055 | 0 | 0 | 14.06 | 0 | | | | | |
| | 0 | 1.444 | 0 | 0 | 8.499 | 0 | 0 | | | | |
| | 0 | 0 | 0 | 0 | 1.031 | 0 | 8.499 | 2.178 | | | |
| | 0 | 4.304 | 0 | 0 | 3.109 | 0 | 4.655 | 4.304 | 4.655 | | |
| | 0 | 4.985 | 0 | 0 | 0 | 0 | 3.484 | 0 | 0.069 | 2.082 | |
| | 0 | 0 | 0 | 0 | 0 | 0 | 0 | 0 | 0 | 0 | |
| | 0 | 0 | 0 | 0 | 0 | 0 | 0 | 0 | 0 | 0 | 0 |
| | 0 | 6.118 | 0 | 0 | 0 | 0 | 4.304 | 2.478 | 0 | 0 | 0 | 0 |

# MEASUREMENT AND COMPARISON OF IMMUNE DIVERSITY BY HIGH-THROUGHPUT SEQUENCING

CROSS-REFERENCE TO RELATED APPLICATIONS

This application is a continuation of application Ser. No. 14/735,066 filed (Jun. 9, 2015), now U.S. Pat. No. 9,290,811 (issued Mar. 22, 2016), which is a continuation of application Ser. No. 13/696,375, filed (Feb. 22, 2013), now U.S. Pat. No. 9,234,240 (issued Jan. 12, 2016), which was the national stage entry of international application PCT/US2011/035507 (filed May 6, 2011), which claims priority from provisional application No. 61/395,116 (filed May 7, 2010). The contents of the aforementioned applications are incorporated herein by reference.

BACKGROUND OF THE INVENTION

A feature of the adaptive immune response is the ability to generate a wide diversity of binding molecules, e.g. T cell antigen receptors and antibodies. A variety of molecular mechanisms exist to generate initial diversity, including genetic recombination at multiple sites. Armed with this initial repertoire of binding moieties, naïve B and T cells circulate where they can come in contact with antigen. Upon exposure to antigen there can be a positive selection process, where cells expressing immunological receptors having desired binding properties are expanded, and may undergo further sequence modification, for example somatic hypermutation, and additional recombination. There can also be a negative selection process, where cells expressing immunological receptors having undesirable binding properties, such as self-reactivity, are deleted. As a result of these selective processes, the repertoire of binding specificities in an individual sample can provide a history of past antigenic exposures, as well as being informative of inherent repertoire capabilities and limitations.

Adaptive immunological receptors of interest include immunoglobulins, or antibodies. This repertoire is highly plastic and can be directed to create antibodies with broad chemical diversity and high selectivity. There is also a good understanding of the potential diversity available and the mechanistic aspects of how this diversity is generated. Antibodies are composed of two types of chains (heavy and light), each containing a highly diversified antigen-binding domain (variable). The V, D, and J gene segments of the antibody heavy-chain variable genes go through a series of recombination events to generate a new heavy-chain gene. Antibodies are formed by a mixture of recombination among gene segments, sequence diversification at the junctions of these segments, and point mutations throughout the gene. The mechanisms are reviewed, for example in Maizels (2005) Annu. Revu. Genet. 39:23-46; Jones and Gellert (2004) Immunol. Rev. 200:233-248; Winter and Gearhart (1998) Immunol. Rev. 162:89-96.

Another adaptive immunological receptor of interest is the T cell antigen receptor (TCR), which is a heterodimer of two chains, each of which is a member of the immunoglobulin superfamily, possessing an N-terminal variable (V) domain, and a C terminal constant domain. The variable domain of the TCR α-chain and β-chain has three hypervariable or complementarity determining regions (CDRs). The β-chain has an additional area of hypervariability (HV4) that does not normally contact antigen. Processes for generating diversity of the TCR are similar to those described for immunoglobulins. The TCR alpha chain is generated by VJ recombination, while the beta chain is generated by V(D)J recombination. Similarly, generation of the TCR gamma chain involves VJ recombination, while generation of the TCR delta chain occurs by V(D)J recombination. The intersection of these specific regions (V and J for the alpha or gamma chain, V D and J for the beta or delta chain) corresponds to the CDR3 region that is important for antigen-MHC recognition. It is the unique combination of the segments at this region, along with palindromic and random N- and P-nucleotide additions, which accounts for the TCR binding repertoire.

While reference is made to binding specificities, and indeed a good deal of serological analysis is based on the physical interactions between antigen and receptor, the underlying cause of the diversity lies in the genetic sequences expressed by lymphocytes, which sequences reflect the myriad processes of recombination, mutation and selection that have acted on the cell. Estimates of immune diversity for antibodies or the related T cell receptors either have attempted to extrapolate from small samples to entire systems or have been limited by coarse resolution of immune receptor genes. However, certain very elementary questions have remained open more than a half-century after being posed: It is still unclear what fraction of the potential repertoire is expressed in an individual at any point in time and how similar repertoires are between individuals who have lived in similar environments. Moreover, because each individual's immune system is an independent experiment in evolution by natural selection, these questions about repertoire similarity also inform our understanding of evolutionary diversity and convergence.

Methods of precisely determining the immune receptor repertoire of an individual, or a sample of interest from an individual, are of great interest for prognosis, diagnosis, and characterization. The present invention addresses that issue.

SUMMARY OF THE INVENTION

Methods and compositions are provided for using nucleic acid sequence analysis to measure characteristics and function of the immune system. A principal application of the invention is in measuring the immunological diversity present in a biological sample. By determining the underlying genetics of the immune repertoire, one can better characterize immune response, immune history, and immune competency. Those characterizations, in turn, lead to improved diagnostic, prognostic, and therapeutic outcomes. Finally, methods of the invention allow personalized immune profiling.

The samples from which immunological-receptor encoding nucleic acids are obtained are typically complex and include, among others, blood, lymph, and biopsy samples. Such samples typically comprise greater than $10^3$ or more different sequences for a receptor of interest. The biological sample may be chosen based upon a particular organ or system, condition or disease of interest. In some embodiments the sample comprises immune-related cells, such as lymphocytes, e.g. T cells, B cells, natural killer cells, etc. Immunological receptor molecules of interest include immunoglobulins, T cell antigen receptors, and major histocompatibility receptors, or fragments thereof. The nature of sequence variations in the sample can be recorded and displayed in an informative manner, e.g. represented in a tree, represented in a three dimensional plot, etc. The analysis of sequence variation is useful for predictive and diagnostic methods relating to the immune capabilities and history of an individual. Such predictions and diagnoses can be used to guide clinical decisions.

Any appropriate sequencing method may be used in the context of the invention. Common methods include sequencing-by-synthesis, Sanger or gel-based sequencing, sequencing-by-hybridization, sequencing-by-ligation, or any other available method. Particularly preferred are high throughput sequencing methods, preferably without the need for cloning or functional expression of the targeted immune molecules. In some embodiments, all the cells in the sample are treated as a single sample, i.e. without segregation or sorting, and used as a source of nucleic acids for sequencing. In other embodiments, cells of interest, including cells of the adaptive immune system, e.g. B cells expressing a marker of interest, plasmablasts, T cells expressing a marker of interest, and the like, are sorted from the starting sample population and used as a source of nucleic acids for sequencing. In some embodiments the sorting is by positive selection, while in others, the sorting is performed by negative selection.

The sequencing data are statistically analyzed to compute correlations in the repertoire (or sets of immunological receptors) of different samples, where samples may be obtained from different individuals or from a single individual at different times, different sites of the body, synthetic libraries, etc. Time points may be taken, for example, following exposure to an antigenic challenge, such as a vaccine, in response to a candidate therapy, during a transplantation process, and the like.

The information obtained from the immune repertoire analysis may be used to diagnose a condition, to monitor treatment, to select or modify therapeutic regimens, and to optimize therapy. With this approach, therapeutic and/or diagnostic regimens can be individualized and tailored according to the specificity data obtained at different times over the course of treatment, thereby providing a regimen that is individually appropriate. In addition, patient samples can be obtained at any point during the treatment process for analysis.

Methods of statistical analysis include the use of algorithms to correct for bias introduced in sample preparation and sequencing of immune repertoires. An algorithm, for example using clustering and PCR filter, may be used to correct for sequence errors (or amplification bias) introduced during sample preparation and sequencing of immune repertoires. Algorithms are provided for the assignment of immune repertoire sequences into V, D, J, and C classes. Algorithms are provided for the assignment of immune repertoire sequences to individual heavy chains, light chains, CDR3, T-cell receptor alpha, beta, delta or gamma chains, etc.

The total corrected repertoire (or set of immunological receptors) can be used to determine the heterogeneity of an immune repertoire (or set of immunological receptors) by computing the entropy. The total corrected repertoire can be characterized by computing the frequency distributions of VDJC/antibody heavy chains.

The invention includes suitable sets of primers for obtaining high throughput sequence information for immunological molecules of interest, e.g. immunoglobulin sequence information, T cell receptor sequence information, MHC sequence information, etc. Sequencing can be performed on sets of nucleic acids across many individuals or on multiple loci in a sample obtained from one individual. Sequence analysis is performed on nucleic acid obtained from cells present in the sample of interest, which may be genomic DNA or a portion thereof, cDNA, or portion thereof; or may be mRNA or cDNA obtained therefrom. In some embodiments cDNA is preferred. Where cDNA is analyzed, the methods may include the use of gene specific primers for reverse transcription of the immunological receptor sequences of interest.

Analysis may include amplifying cDNA using a set of primers designed to selectively bind immunological receptor gene sequences. For example, primers may be designed to amplify functional V gene segments of immunoglobulin loci, to amplify functional V gene segments of TCR loci, to amplify immunoglobulin or TCR constant region segments, to amplify consensus MHC gene segments, and the like. In some embodiments, an independent primer set is included to test PCR bias.

The present disclosure also provides a method for diagnosis or prognosis of a condition of interest, comprising: obtaining one or more reference samples comprising cells of interest; performing an immune repertoire analysis on the reference sample(s); using clustering analysis on the immune repertoire analysis results to identify features common to the condition of interest; performing immune repertoire analysis on a test sample obtained from an individual in need of diagnosis; comparing the repertoire analysis results obtained from the test sample to reference repertoire analysis results, wherein a pre-determined level of similarity to reference repertoire analysis results are indicative of the absence or presence of the condition.

Conditions of interest for diagnosis and prognosis include numerous aspects of immune competence and antigenic exposure, e.g. including the absence or presence of autoimmune disease or predisposition to autoimmune disease; the status of transplantation; the presence of cancers of the immune system, e.g. leukemias, lymphomas, myelomas, etc.; exposure to antigenic stimulus, e.g. exposure to cancer antigens; exposure to viral, bacterial, parasitic antigens; exposure to vaccines; exposure to allergens; exposure to foodstuffs, e.g. gluten proteins, etc.; the innate repertoire of an individual indicating an inherent ability to respond to an antigen of interest; and the like.

Yet another method provided herein is a method for screening for a therapeutic agent comprising: exposing a first subject to one or more test agents; obtaining a suitable cell sample from the subject, e.g. a blood sample, etc.; performing immune repertoire analysis on said cell sample; and comparing the immune repertoire analysis results to a immune repertoire analysis result derived from either: (i) a second reference sample with a known response profile; or (ii) the first subject prior to said exposing step; and identifying an agent that affects immune repertoire in a desirable manner, e.g. deletion of self-reactive receptors; enhancement of pathogen-specific receptors; etc. The subject may be, for example, suffering or susceptible to an autoimmune disease, a chronic infection, following transplantation of a tissue, suffering from a cancer, etc. A therapeutic agent can be an antibody or antibody fragment, a drug or other small molecule, nucleic acid (for example an siRNA), RNA, DNA, RNA-DNA chimera, protein, peptide, and the like.

Further provided herein is a method of determining likelihood of a response by a subject to an agent, which may include a therapeutic agent, an infectious agent, a vaccine, an autoantigen, and the like, comprising; obtaining a suitable cell sample from the subject, e.g. a blood sample, etc.; performing immune repertoire analysis on said cell sample; and comparing the immune repertoire analysis results to a immune repertoire analysis result derived from a reference sample with a known response profile to said agent; and determining likelihood of a response by a subject based on immune repertoire.

Also provided herein is a method of collecting data regarding an immune repertoire, comprising the steps of: collecting data regarding a immune repertoire using any of the methods described herein and sending said data to a computer. A computer can be connected to a sequencing apparatus. Data corresponding to an immune repertoire can further be stored after sending, for example the data can be stored on a computer-readable medium which can be extracted from the computer. Data can be transmitted from the computer to a remote location, for example, via the internet.

The present disclosure also provides methods of characterizing a set of immunological receptors, or fragments thereof, comprising: a) sequencing a population of nucleic acids encoding at least $10^3$, $10^4$, $10^5$, $10^6$, $10^7$, $10^8$, $10^9$, $10^{10}$, $10^{11}$, $10^{12}$ or more immunological receptors, or fragments thereof, or obtaining at least $10^3$, $10^4$, $10^5$, $10^6$, $10^7$, $10^8$, $10^9$, $10^{10}$, $10^{11}$, $10^{12}$ or more sequencing reads from a cellular sample; and b) using sequencing data from step a) to characterize said set of immunological receptors. Some embodiments also comprise applying a statistical metric that characterizes diversity or a clustering analysis to the sequencing data from step a) in order to characterize said set of immunological receptors or fragments thereof. In some cases, sequence variation is represented as a function of sequence frequency. In some cases, the statistical metric used is an entropy metric, an ecology metric, a variation of abundance metric, a species richness metric, or a species heterogeneity metric.

Also provided herein are methods of comparing a set of immunological receptors from an organism with a set of immunological receptors from another organism or from a reference sample. In some cases, (1) immunological receptors from an organism are compared to a reference sample; (2) immunological receptors from a second organism are compared to a reference sample; and the results of (1) are compare to those from (2).

Further provided herein are methods of selecting a treatment for a person afflicted with a condition comprising: a) sequencing a population of nucleic acids encoding immunological receptors or fragments thereof of said person; b) using sequence data from step a to characterize said person's immunological response; and c) selecting a treatment based on said characterization. In some embodiments, the method comprises a method of diagnosing a person suspected of having a condition comprising: a) sequencing a population of nucleic acids encoding immunological receptors, or fragments thereof, of said person; b) using sequence data from step a to characterize said person's immunological response; and c) selecting a treatment or diagnosis based on said characterization.

Also provided herein are software products tangibly embodied in a machine-readable medium, the software product comprising instructions operable to cause one or more data processing apparatus to perform operations comprising: a) clustering sequence data from a plurality of immunological receptors or fragments thereof; and b) providing a statistical analysis output on said sequence data. Also provided herein are software products tangibly embodied in a machine-readable medium, the software product comprising instructions operable to cause one or more data processing apparatus to perform operations comprising: storing sequence data for more than $10^3$, $10^4$, $10^5$, $10^6$, $10^7$, $10^8$, $10^9$, $10^{10}$, $10^{11}$, $10^{12}$ immunological receptors or more than $10^3$, $10^4$, $10^5$, $10^6$, $10^7$, $10^8$, $10^9$, $10^{10}$, $10^{11}$, $10^{12}$ sequence reads.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 1A-1B Schematic drawing of the VDJ recombination of an antibody heavy-chain gene, the cDNA amplicon library construction, and the informatics pipeline. The heavy-chain VDJ segment of an antibody is created by recombination, junctional diversity, and hypermutation. We designed primer sets to amplify the expressed heavy-chain mRNA, which were then sequenced and analyzed as outlined. High-throughput sequencing allows determination of the identity of nearly all heavy-chain sequences. (FIG. 1B) Gender and family information for the 14 sequenced zebrafish.

FIG. 2G-2K. The entire expressed VDJ repertoires for individual fish FIGS. 2G, 2H, 2J, and 2K (top to bottom). The three axes enumerate all possible V, D, and J values, so each point in three-space is a unique VDJ combination. Both the size of the sphere at each point and the intensity correspond to the number of reads matching that particular VDJ combination. Gray scale is plotted on a linear scale, and the dot size is plotted on a log scale. The upper limits of the scales are set to the most populated VDJ combination for each fish, with PCR bias factored out.

FIG. 3A-3D. VDJ repertoire analysis for all 14 fish. (FIG. 3A) Abundance distribution for each VDJ combination. A small number of VDJ combinations are highly represented in each fish, and most VDJ combinations are represented only at low abundance. The shape of the distribution is common among all of the fish sampled. This histogram is oriented sideways (from left to right) to emphasize that a small number of VDJ combinations are highly abundant, with a distribution that falls off rapidly. (FIG. 3B) Rarefaction analysis of VDJ diversity demonstrates that as one sequences more deeply into a fish, the number of new VDJ classes discovered saturates. (FIG. 3C) Histogram of correlations between VDJ repertoires. The data are collected as histograms and compared to simulated fish which have random VDJ repertoires. The simulated fish have no significant correlations, whereas some of the real fish have high correlations, representing 5 SD outliers of the random model. The highest correlations are from males in the same family (table S5A). (FIG. 3D) When the largest VDJ class in each fish is eliminated, the correlations are reduced and there is a larger proportion of moderate female correlations.

FIG. 4A-4D. Antibody heavy-chain repertoire diversity estimates of 200 bp reads for IgM in all 14 fish. (FIG. 4A) Rarefaction analysis of heavy-chain diversity demonstrates that as one sequences more deeply into a fish, the number of new antibodies discovered (while applying a PCR filter with fraction-of-reads per VJ class set to 95%) saturates at a few thousand. (FIG. 4B) Antibody abundance distributions for each fish for clusters with >2 reads. This histogram is oriented sideways (from left to right) to emphasize that a small number of antibodies (clusters) are highly abundant, with a distribution that falls off rapidly as a power law. The shape of the distribution is universal among all of the fish sampled. The bend at small abundance is caused by variability in the total reads sampled per fish bias-normalization and is not significant. (FIG. 4C) Total antibody diversity estimates for IgM using different criteria. VDJ diversity is the number of VDJ classes per fish, as described in FIG. 3A. Antibodies observed (PCR filter, fraction-of-reads set to 95%; VDJ classes composed only of antibody clusters with two or fewer reads are counted as one) is the number of unique antibodies per fish described in FIG. 4A. Capture-recapture estimate 1 refers to an estimate based on observed antibody abundances. Capture-recapture estimate 2 refers to an estimate using equal probability of all antibodies. Antibodies observed, undercount corrected refers to the upper bound. (FIG. 4D) Histogram of number of fish with shared IgM sequences (corresponding to all clusters of size >2 reads). Hundreds of sequences are shared between pairs of fish, while a few tens of sequences are shared between three fish. Five sequences are shared between four or more fish, and none are shared among all fourteen fish. Sequence comparisons without mutations incorporate differences at the V/D and D/J junctions alone. Convergence on the amino acid level is also plotted.

FIG. 5A, the total number of bases in the control run at a given position and quality score. FIG. 5B, the probability that given any pair of position/quality-score values, the base is incorrect. In the weighting scheme, all bases with quality score less than or equal to 8 were assumed incorrect.

FIG. 6A, fraction of total reads in the correct clusters, singlets and doublets group and in-between the correct clusters as a function of cluster radii. FIG. 6B, fraction of total clusters in the correct clusters, singlets and doublets group and in between the correct clusters as a function of cluster radii. Mean and standard deviation were calculate based on each of the 38 known templates.

FIG. 15A-15F. Comparison of antibody isotype frequency between multiplexed and simplexed PCR for each B cell samples taken from six subjects. FIG. 15A, FIG. 15B and FIG. 15C—multiplexed PCR; FIG. 15D, FIG. 15E and FIG. 15F—simplexed PCR. Three age groups, 8-17 years old, 18-30 years old and 70-100 years old.

FIG. 16. Zebrafish vaccination experiment. WIK zebrafish from a single cross were raised in a quarantine system from birth until 9 months of age. Fish were divided into tanks with shared circulating water and underwent immersion vaccination by 6 different combinations of 3 haptens, DNP(12)-BSA, TNP(11)-BSA, and ABA(10)-BSA. Immersions were performed three times at one-week intervals, after which fish were euthanized, flash-frozen, and processed for sequencing.

FIG. 17A. Read-weighted VDJ correlations (color bar in upper-right) of 40,000 read-subsampled and lineage-analyzed dataset in 29 fish. FIG. 17B. Read-weighted VJ correlations of those sequences belonging to lineages with at least 5 unique sequences. FIG. 17C. Read-weighted VJ correlations of the 50% of the data from panel (FIG. 17B) with the fewest mutations. FIG. 17D. Read-weighted VJ correlations of the 50% of the data from panel (FIG. 17B) with the most mutations.

FIG. 23. Fraction of reverse reads assigned for each V, D and J gene segment and VDJ combination coverage measured for both IgM and IgZ.

Figures 24A, 24B:
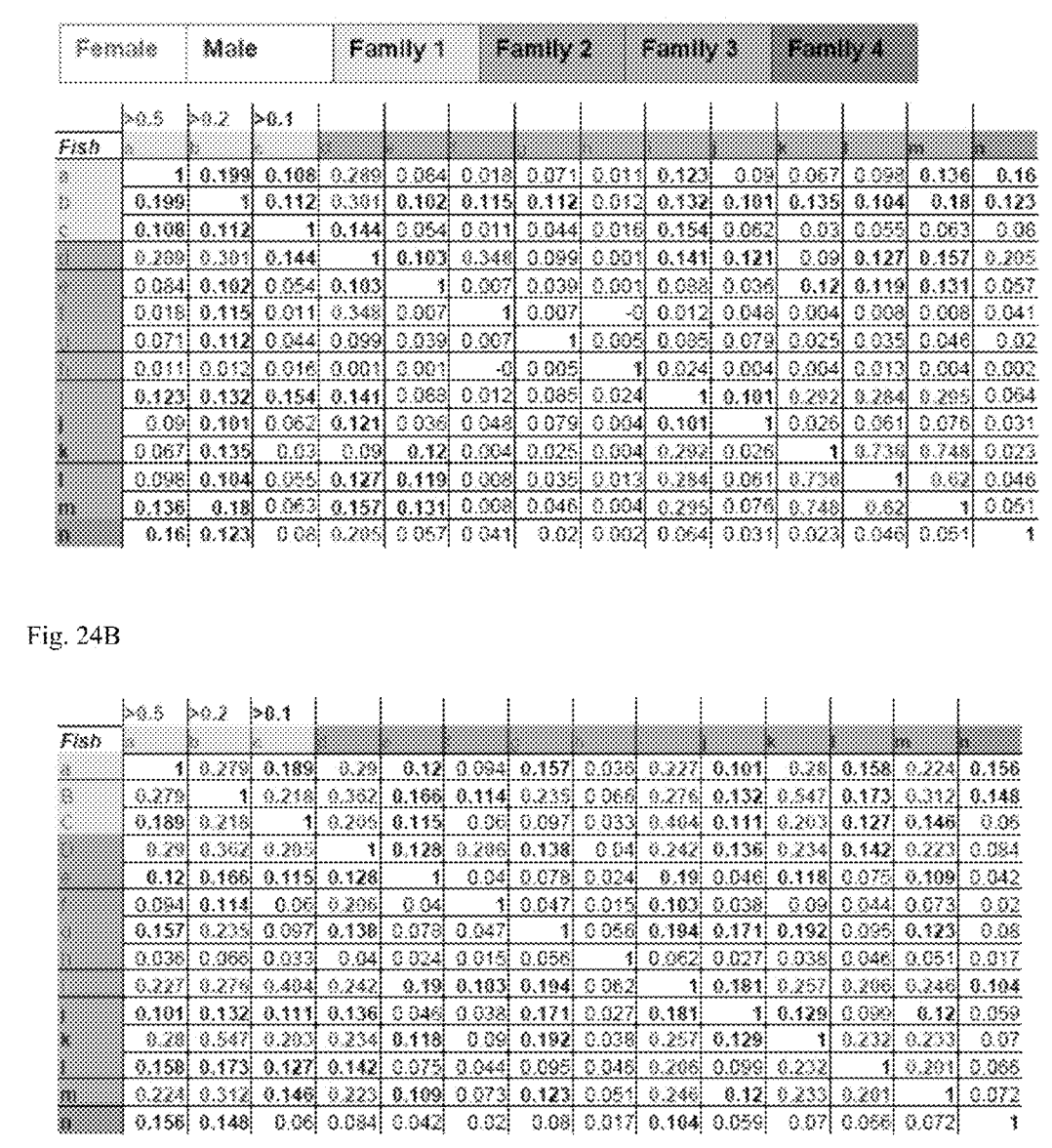

FIG. 24A-24B. VDJome correlations between all 14 fish, across all VDJ combinations (FIG. 24A) and excluding the most abundant from each fish (FIG. 24B). Families and genders are color coded according to the legend above. High correlations (>0.5) are shown in red, and moderate (>0.2) are shown in green.

FIG. 25A-25C. Convergence of mutated sequences. The average number of convergent events (FIG. 25A) is calculated by looking for matching naive sequences in different fish. Every pair of mutated sequences in different fish with common naive origin is then regarded as an independent trial, with a probability 1/3m of a match, where m is the number of mutable base-pairs. Of those sequences that are found to have mutations, the observed number (FIG. 25B) are counted. The probability that a frequency of convergence at or above the level observed becomes our p-value. The quantity −log 10 p is calculated and shown for every pair of fish (FIG. 25C). Any value is considered significant.

DETAILED DESCRIPTION

Figure 5A:
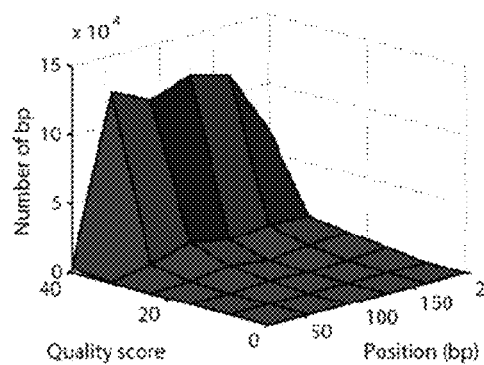
FIG. 5A-5B. Error distributions along read length of 200 bp for the control library run.

Methods and compositions are provided for sequence analysis of the immune repertoire. Analysis of sequence information underlying the immune repertoire provides a significant improvement in understanding the status and function of the immune system. For example, sequence information is useful to diagnose disease, immune status, prognosis, and response to therapy. Sequencing is also useful in therapeutic selection and monitoring and in the evaluation of therapeutic candidates.

The invention involves obtaining nucleic acid from a biological sample and sequencing DNA or RNA relating to immunological receptor molecules. Sequencing information obtained from an individual sample is then compared to known sequences (e.g., in a database), to sequences from other samples, or to sequences from the same source over time.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. In this specification and the appended claims, the singular forms "a," "an" and "the" include plural reference unless the context clearly dictates otherwise.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, illustrative methods, devices and materials are now described.

All publications mentioned herein are incorporated herein by reference for the purpose of describing and disclosing the subject components of the invention that are described in the publications, which components might be used in connection with the presently described invention.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Immune Repertoire Analysis or Analysis of Sets of Immunological Receptors

Methods of the invention allow characterization of the immune repertoire by sequencing all or a portion of the molecules that make up the immune system, including, but not limited to immunoglobulins, T cell receptors, and MHC receptors. Samples may represent all or a part of the immune repertoire of the individual from which the sample is obtained. As described above, any biological sample is complex in terms of the number of immune receptor sequences that are present. Methods of the invention contemplate high-throughput sequence of the complex array of immune-encoding nucleic acids present in a biological sample. Samples may also be processed to produce a library of nucleic acids (e.g., DNA, RNA, cDNA, mRNA, cRNA) encoding immunological receptors. The library may comprise genomic DNA or RNA or may be a synthetic library created by any method known in the art, including from in vitro random mutagenesis of nucleic acids.

The cells in a sample for analysis may have been separated or enriched prior to analysis, or a sample, e.g. a clinical sample, may be analyzed in the absence of any enrichment.

To obtain the sequence information, the cells present in the sample are lysed and nucleic acids of interest (e.g., genomic DNA, mRNA, cDNA, cRNA, etc.) are collected. Where mRNA is being analyzed, it will generally be converted to cDNA by reverse transcriptase. Primers for cDNA synthesis, as described above, may be selective for the immunological receptor of interest. The immune receptor sequences are then amplified with a set of primers selective for the immunological receptor of interest.

During PCR amplification there is a possibility of introducing a bias, and thus it may be desirable to include a control amplification, and an analysis step to normalize the data. The degree of PCR bias introduced in the sample preparation and sequencing process can be estimated by comparing the representation of the known clones before and after PCR, and determining the bias that is introduced. In the quantitative analyses that follow, these measured biases are used to normalize the data. The control data may also be used to measure sequencing errors. Other methods of controlling for amplification bias include one or more of the following methods (described in more detail herein and in the examples): PCR filter, clustering analysis, and using two or more primer sets.

The amplified pool (or, in some cases, a pool that has not been amplified) of nucleic acids is then subjected to high throughput sequencing (e.g., massively-parallel sequencing). In some embodiments of the invention, the analysis uses pyrosequencing (e.g., massively parallel pyrosequencing) relying on the detection of pyrophosphate release on nucleotide incorporation, rather than chain termination with dideoxynucleotides, and as described by, for example, Ronaghi et al. (1998) Science 281:363; and Ronaghi et al. (1996) Analytical Biochemistry 242:84, herein specifically incorporated by reference. The pyrosequencing method is based on detecting the activity of DNA polymerase with another chemiluminescent enzyme. Essentially, the method allows sequencing of a single strand of DNA by synthesizing the complementary strand along it, one base pair at a time, and detected which base was actually added at each step. The template DNA is immobile and solutions of selected nucleotides are sequentially added and removed. Light is produced only when the nucleotide solution complements the first unpaired base of the template.

Sequencing platforms that can be used in the present disclosure include but are not limited to: pyrosequencing, sequencing-by-synthesis, single-molecule sequencing, nanopore sequencing, sequencing-by-ligation, or sequencing-by-hybridization. Preferred sequencing platforms are those commercially available from Illumina (RNA-Seq) and Helicos (Digital Gene Expression or "DGE"). "Next generation" sequencing methods include, but are not limited to those commercialized by: 1) 454/Roche Lifesciences including but not limited to the methods and apparatus described in Margulies et al., Nature (2005) 437:376-380 (2005); and U.S. Pat. Nos. 7,244,559; 7,335,762; 7,211,390; 7,244,567; 7,264,929; 7,323,305; 2) Helicos BioSciences Corporation (Cambridge, Mass.) as described in U.S. application Ser. No. 11/167,046, and U.S. Pat. Nos. 7,501,245; 7,491,498; 7,276,720; and in U.S. Patent Application Publication Nos. US20090061439; US20080087826; US20060286566; US20060024711; US20060024678; US20080213770; and US20080103058; 3) Applied Biosystems (e.g. SOLiD sequencing); 4) Dover Systems (e.g., Polonator G.007 sequencing); 5) Illumina as described U.S. Pat. Nos. 5,750,341; 6,306,597; and 5,969,119; and 6) Pacific Biosciences as described in U.S. Pat. Nos. 7,462,452; 7,476,504; 7,405,281; 7,170,050; 7,462,468; 7,476,503; 7,315,019; 7,302,146; 7,313,308; and US Application Publication Nos. US20090029385; US20090068655; US20090024331; and US20080206764. All references are herein incorporated by reference. Such methods and apparatuses are provided here by way of example and are not intended to be limiting.

The effects of sequencing error or amplification error can be mitigated by the clustering process that allows one to determine a consensus sequence by grouping several reads together, and thus average out the error. The clustering algorithm may be tested on the control data in order to validate parameter choices.

Figure 12:
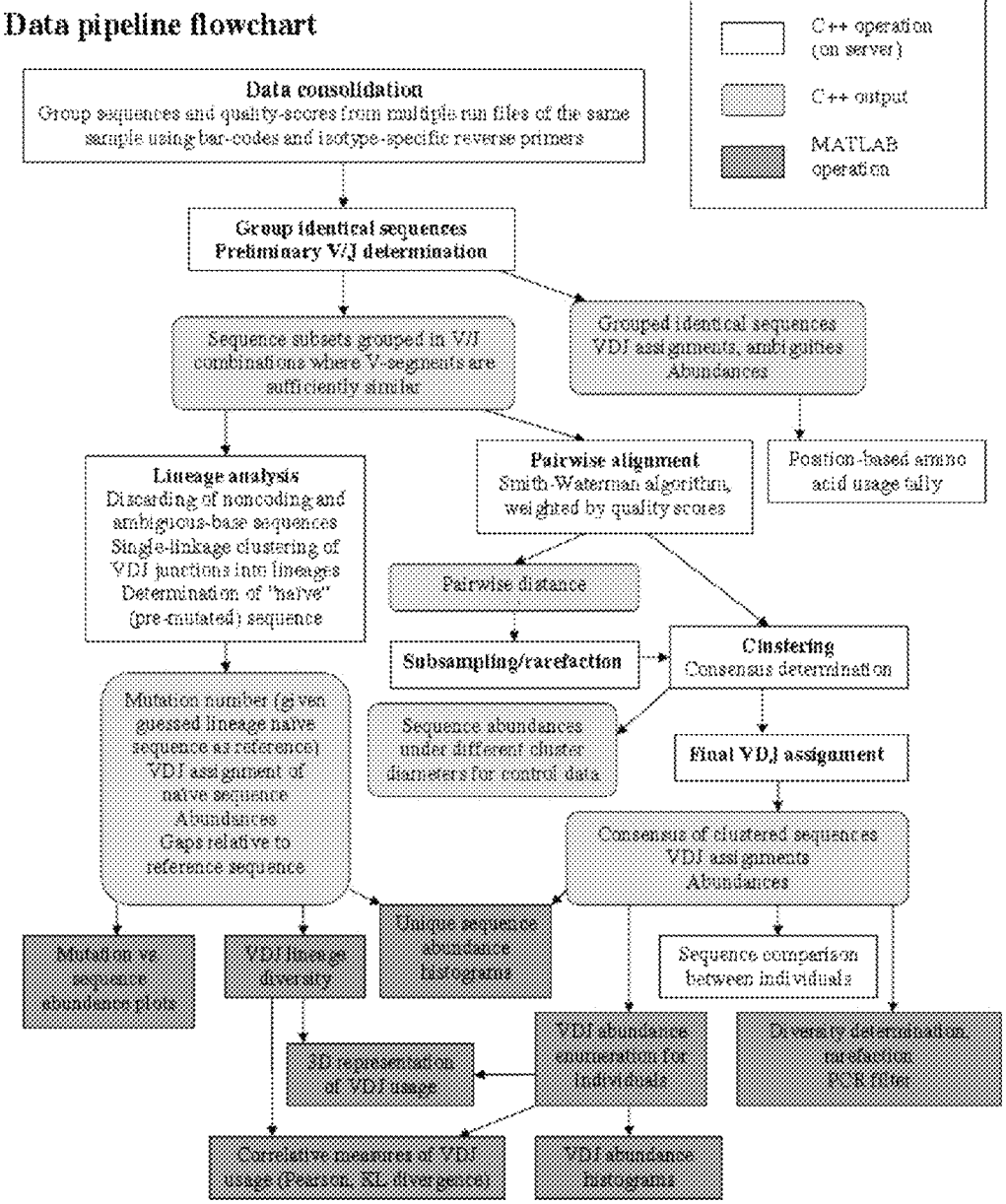
FIG. 12. Flow chart depicting a data pipeline.

The high throughput sequencing provides a very large dataset, which is then analyzed in order to establish the repertoire. Non-limiting examples of data analysis steps are summarized in the flow chart of FIG. 12.

Grouping Identical Sequences and Preliminary V/J Determination:

Initially sequences may be matched based on perfect identity, and the number of identical reads stored. Quality scores of identical reads are then averaged. V- and J-reference genome sequences (or synthetic reference sequences) are Smith-Waterman aligned to each sequence. (Other reference sequences that could be used are any combination of V-, D-, J- and C-). To avoid edge effects (due to enzymatic trimming) the reference-genome alignment five base-pairs away from the edges of the alignment are given higher weight. Those sequences failing to match minimally to any reference gene segment are discarded. Those that are ambiguous (matching equally to more than one reference genome segment) are retained but are recorded in an output file for being ambiguous (their provisional V-assignment is given to the first enumerated V-segment in the ambiguous subset).

Sequence Subsets Grouped in V/J Combinations where V-Segments are Sufficiently Similar:

After preliminary V/J assignments, genomic-V sequences are aligned to one another, and genomic clusters are formed based on single-linkage clustering with a threshold (e.g., 6 bp-distance threshold). Sequences grouped under V/J combinations with V's belonging to the same cluster are grouped for pairwise alignment.

Pairwise Alignment:

Pair-wise alignment of sequences can be achieved with a specific algorithm, e.g., a quality-score-weighted Smith-Waterman algorithm. With the start positions of the alignment fixed (due to common reverse primers), the alignment grid is confined to the area less than or equal to a specific number of base pairs (e.g., 9 bp) off the diagonal (effectively limiting the number of admissible gap-errors or deletion-errors to 9 on a single read length).

Pairwise Distance Matrices:

Matrices such as Smith-Waterman distance matrices for each V/J grouping can be outputted to text files for later reference.

Subsampling/Rarefaction:

Pre-determined sampling depths can be used to randomly select reads across all V/J combinations. Using printed distance matrices, sub-matrices are assembled and used for clustering.

Clustering and Consensus Determination:

Seeded quality-threshold clustering is performed by seeding clusters with the sequence i that maximizes the centrality measure $c_i = \Sigma_j \exp(-d_{ij})$ where $d_{ij}$ is the alignment distance between i and all sequences j. Clustering then proceeds by adding to the cluster whichever sequence minimally increases the diameter of the cluster (ie the maximum distance between any two members). Once no sequence can be added without increasing the diameter above a defined threshold, cluster-formation terminates. Consensus sequences for each cluster are determined by sequence-vote: if there is a sequence with the most identical reads corresponding to it, that sequence is made the consensus. Otherwise the consensus is assigned the sequence that maximizes the centrality measure, above, relative to all other members of the same cluster.

Lineage Analysis:

After identical sequences have been grouped (with read-number/abundance stored), sequences containing stop-codons, ambiguous bases, or gaps relative to the reference genome are discarded. Junctional regions (the end of the V-encoded region to the beginning of the J-encoded region) are determined by using a moving window, whose size is equal to its distance from the end of the genomic exon, to find the furthest location from the end of each junction at which sequence-identity dropped below 50%. The junctional boundary is then defined as the furthest occurrence of a mismatch/insertion/deletion within the window (see Example 1)

Any two sequences with junction boundaries varying by at most one nucleotide and having greater than or equal to 80% identity at the VDJ junction are allowed to form single-linkage clusters. These clusters allow sequences to "chain", so that multiple sequences that differ in increments from one another can be traced back to the original un-mutated sequence. Sequences retain their identity, but the clusters they form defined hypothetical lineages. Whichever member sequence has the fewest differences relative to the reference genome (away from the junction as illustrated above) is defined as the naïve sequence of the lineage. Mutations are determined by direct comparison to this sequence. Similar methods can be used to determine V, D, J, C, VJ, VDJ, VJC, VDJC lineage usage or diversity.

Final VDJ Assignment:

For clustered sequences, the consensus is aligned to V and J segments as in the preliminary assignments (or C-, D-segments as appropriate). The junctions derived using the same algorithm as above are then aligned to all possible D-segments, with a high gap-open penalty (to prevent the alignment from being significantly affected by non-templated nucleotides). Similar methods can be applied to determine final V, D, J, C, VJ, VDJ, VJC, VDJC assignments.

Diversity Determination, Rarefaction, PCR Filter:

Control measurements show clustered 250 bp read-length sequences having 90% of their reads correctly clustered, roughly what is expected for PCR error rates of 5e−5 per base pair per cycle for an effective number of cycles numbering between 20 and 30. Rarefaction controls show clustering correctly accounting for all sequences without PCR, suggesting that "orphan" sequences can be treated as PCR errors alone. This is corroborated by the fact that for PCR-amplified controls, applying the PCR filter with a 90%-of-reads criterion is exactly the point at which diversity counts are allowed to saturate as a function of sequencing depth. Clusters are added to the correct-cluster pool, starting with the most abundant, and adding clusters in decreasing abundance until the top 90% of reads are included, at which point the algorithm terminates. This is done for each V/J (or any other V/J/D/C, etc.) combination independently to avoid bias.

A rough estimate for total diversity, T, can be derived from knowing the distribution of unique sequences, Prob(x), over all abundance x $$r_i = \frac{\Sigma_{x_j=x}(1-(1-x(T\Sigma_j x_j Prob(x_j))^{-1})^M)^2 Prob(x)}{\Sigma_{x_j=x}(1-(1-x(T\Sigma_j x_j Prob(x_j))^{-1})^M) Prob(x)}$$

VDJ Lineage Diversity:

VDJ usage is enumerated by the number of observed lineages falling into each VJ, VDJ, VJC, or VDJC (e.g., VDJ) combination at a given read-depth.

VDJ and Unique Sequence Abundance Histograms:

Histograms are plotted by binning VDJ and unique sequence abundances (the latter which is either clustered or has undergone lineage-analysis filtering and grouping) into log-spaced bins.

3D Representation of VJ, VDJ, VJC, or VDJC (e.g., VDJ) Usage:

Repertoires are represented by applying V-, D-, J-, and/or C-segments to different axes on a three-dimensional plot. Using either abundance (generally read number, which can be bias-normalized) or observed lineage diversity, bubbles of varying sizes are used at each V/D/J/C coordinate to represent the total usage of that combination.

Mutation Vs. Sequence Abundance Plots:

After undergoing lineage analysis, unique sequences are binned by read-number (or bias-normalized abundance) into log-spaced bins. For a given abundance-bin, the number of mutations per unique sequence is averaged, giving a mutation vs. abundance curve.

Correlative Measures of V, D, J, C, VJ, VDJ, VJC, VDJC, Antibody Heavy Chain, Antibody Light Chain, CDR3, or T-Cell Receptor) Usage (Pearson, KL Divergence):

VJ, VDJ, VJC, or VDJC (e.g., VDJ) combinations are treated as vectors with indexed components weighted by either lineage-diversity or abundance for that VDJ combination. Pearson correlations and KL-divergences between each pair of individuals are then calculated over the indices i.

The results of the analysis may be referred to herein as an immune repertoire analysis result, which may be represented as a dataset that includes sequence information, representation of V, D, J, C, VJ, VDJ, VJC, VDJC, antibody heavy chain, antibody light chain, CDR3, or T-cell receptor usage, representation for abundance of V, D, J, C, VJ, VDJ, VJC, VDJC, antibody heavy chain, antibody light chain, CDR3, or T-cell receptor and unique sequences; representation of mutation frequency, correlative measures of VJ V, D, J, C, VJ, VDJ, VJC, VDJC, antibody heavy chain, antibody light chain, CDR3, or T-cell receptor usage, etc. Such results may then be output or stored, e.g. in a database of repertoire analyses, and may be used in comparisons with test results, reference results, and the like.

After obtaining an immune repertoire analysis result from the sample being assayed, the repertoire can be compared with a reference or control repertoire to make a diagnosis, prognosis, analysis of drug effectiveness, or other desired analysis. A reference or control repertoire may be obtained by the methods of the invention, and will be selected to be relevant for the sample of interest. A test repertoire result can be compared to a single reference/control repertoire result to obtain information regarding the immune capability and/or history of the individual from which the sample was obtained. Alternately, the obtained repertoire result can be compared to two or more different reference/control repertoire results to obtain more in-depth information regarding the characteristics of the test sample. For example, the obtained repertoire result may be compared to a positive and negative reference repertoire result to obtain confirmed information regarding whether the phenotype of interest. In another example, two "test" repertoires can also be compared with each other. In some cases, a test repertoire is compared to a reference sample and the result is then compared with a result derived from a comparison between a second test repertoire and the same reference sample.

Determination or analysis of the difference values, i.e., the difference between two repertoires can be performed using any conventional methodology, where a variety of methodologies are known to those of skill in the array art, e.g., by comparing digital images of the repertoire output, by comparing databases of usage data, etc.

A statistical analysis step can then be performed to obtain the weighted contribution of the sequence prevalence, e.g. V, D, J, C, VJ, VDJ, VJC, VDJC, antibody heavy chain, antibody light chain, CDR3, or T-cell receptor usage, mutation analysis, etc. For example, nearest shrunken centroids analysis may be applied as described in Tibshirani et al. (2002) P.N.A.S. 99:6567-6572 to compute the centroid for each class, then compute the average squared distance between a given repertoire and each centroid, normalized by the within-class standard deviation.

A statistical analysis may comprise use of a statistical metric (e.g., an entropy metric, an ecology metric, a variation of abundance metric, a species richness metric, or a species heterogeneity metric.) in order to characterize diversity of a set of immunological receptors. Methods used to characterize ecological species diversity can also be used in the present invention. See, e.g., Peet, *Annu Rev. Ecol. Syst.* 5:285 (1974). A statistical metric may also be used to characterize variation of abundance or heterogeneity. An example of an approach to characterize heterogeneity is based on information theory, specifically the Shannon-Weaver entropy, which summarizes the frequency distribution in a single number. See, e.g., Peet, *Annu Rev. Ecol. Syst.* 5:285 (1974).

The classification can be probabilistically defined, where the cut-off may be empirically derived. In one embodiment of the invention, a probability of about 0.4 can be used to distinguish between individuals exposed and not-exposed to an antigen of interest, more usually a probability of about 0.5, and can utilize a probability of about 0.6 or higher. A "high" probability can be at least about 0.75, at least about 0.7, at least about 0.6, or at least about 0.5. A "low" probability may be not more than about 0.25, not more than 0.3, or not more than 0.4. In many embodiments, the above-obtained information is employed to predict whether a host, subject or patient should be treated with a therapy of interest and to optimize the dose therein.

As described herein, a rarefaction analysis of sequence data obtained by any methods described herein may be employed to estimate the completeness of the measurement of immunological repertoire (or of the set of immunological receptors).

Diagnostics and Prognostics

The invention finds use in the prevention, treatment, detection, diagnosis, prognosis, or research into any condition or symptom of any condition, including cancer, inflammatory diseases, autoimmune diseases, allergies and infections of an organism. The organism is preferably a human subject but can also be derived from non-human subjects, e.g., non-human mammals. Examples of non-human mammals include, but are not limited to, non-human primates (e.g., apes, monkeys, gorillas), rodents (e.g., mice, rats), cows, pigs, sheep, horses, dogs, cats, or rabbits.

Examples of cancer include prostrate, pancreas, colon, brain, lung, breast, bone, and skin cancers. Examples of inflammatory conditions include irritable bowel syndrome, ulcerative colitis, appendicitis, tonsilitis, dermatitis. Examples of atopic conditions include allergy, asthma, etc. Examples of autoimmune diseases include IDDM, RA, MS, SLE, Crohn's disease, Graves' disease, etc. Autoimmune diseases also include Celiac disease, and dermatitis herpetiformis. For example, determination of an immune response to cancer antigens, autoantigens, pathogenic antigens, vaccine antigens, and the like is of interest.

In some cases, nucleic acids (e.g., genomic DNA, mRNA, etc.) are obtained from an organism after the organism has been challenged with an antigen (e.g., vaccinated). In other cases, the nucleic acids are obtained from an organism before the organism has been challenged with an antigen (e.g., vaccinated). Comparing the diversity of the immunological receptors present before and after challenge, may assist the analysis of the organism's response to the challenge.

Methods are also provided for optimizing therapy, by analyzing the immune repertoire in a sample, and based on that information, selecting the appropriate therapy, dose, treatment modality, etc. that is optimal for stimulating or suppressing a targeted immune response, while minimizing undesirable toxicity. The treatment is optimized by selection for a treatment that minimizes undesirable toxicity, while providing for effective activity. For example, a patient may be assessed for the immune repertoire relevant to an autoimmune disease, and a systemic or targeted immunosuppressive regimen may be selected based on that information.

A signature repertoire for a condition can refer to an immune repertoire result that indicates the presence of a condition of interest. For example a history of cancer (or a specific type of allergy) may be reflected in the presence of immune receptor sequences that bind to one or more cancer antigens. The presence of autoimmune disease may be reflected in the presence of immune receptor sequences that bind to autoantigens. A signature can be obtained from all or a part of a dataset, usually a signature will comprise repertoire information from at least about 100 different immune receptor sequences, at least about $10^2$ different immune receptor sequences, at least about $10^3$ different immune receptor sequences, at least about $10^4$ different immune receptor sequences, at least about $10^5$ different immune receptor sequences, or more. Where a subset of the dataset is used, the subset may comprise, for example, alpha TCR, beta TCR, MHC, IgH, IgL, or combinations thereof.

The classification methods described herein are of interest as a means of detecting the earliest changes along a disease pathway (e.g., a carcinogenesis pathway, inflammatory pathway, etc.), and/or to monitor the efficacy of various therapies and preventive interventions.

The methods disclosed herein can also be utilized to analyze the effects of agents on cells of the immune system. For example, analysis of changes in immune repertoire following exposure to one or more test compounds can performed to analyze the effect(s) of the test compounds on an individual. Such analyses can be useful for multiple purposes, for example in the development of immunosuppressive or immune enhancing therapies.

Agents to be analyzed for potential therapeutic value can be any compound, small molecule, protein, lipid, carbohydrate, nucleic acid or other agent appropriate for therapeutic use. Preferably tests are performed in vivo, e.g. using an animal model, to determine effects on the immune repertoire.

Agents of interest for screening include known and unknown compounds that encompass numerous chemical classes, primarily organic molecules, which may include organometallic molecules, genetic sequences, etc. An important aspect of the invention is to evaluate candidate drugs, including toxicity testing; and the like.

In addition to complex biological agents candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents can comprise cyclical carbon or heterocyclic structures and/or aromatic or polyaromatic structures substituted with one or more of the above functional groups. Candidate agents can also be found among biomolecules, including peptides, polynucleotides, saccharides, fatty acids, steroids, purines, pyrimidines, derivatives, structural analogs or combinations thereof. In some instances, test compounds may have known functions (e.g., relief of oxidative stress), but may act through an unknown mechanism or act on an unknown target.

Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

Test compounds include all of the classes of molecules described above, and can further comprise samples of unknown content. Of interest are complex mixtures of naturally occurring compounds derived from natural sources such as plants, fungi, bacteria, protists or animals. While many samples will comprise compounds in solution, solid samples that can be dissolved in a suitable solvent may also be assayed. Samples of interest include environmental samples, e.g., ground water, sea water, mining waste, etc., biological samples, e.g. lysates prepared from crops, tissue samples, etc.; manufacturing samples, e.g. time course during preparation of pharmaceuticals; as well as libraries of compounds prepared for analysis; and the like (e.g., compounds being assessed for potential therapeutic value, i.e., drug candidates).

Samples or compounds can also include additional components, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, for example from about 0.1 ml to 1 ml of a biological sample can be sufficient.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Some agent formulations do not include additional components, such as preservatives, that may have a significant effect on the overall formulation. Thus, such formulations consist essentially of a biologically active compound and a physiologically acceptable carrier, e.g. water, ethanol, DMSO, etc. However, if a compound is liquid without a solvent, the formulation may consist essentially of the compound itself.

Databases of Expression Repertoires and Data Analysis

Also provided are databases of immune repertoires or of sets of immunological receptors. Such databases can typically comprise repertoires results derived from various individual conditions, such as individuals having exposure to a vaccine, to a cancer, having an autoimmune disease of interest, infection with a pathogen, and the like. Such databases can also include sequences of immunological receptors derived from synthetic libraries, or from other artificial methods. The repertoire results and databases thereof may be provided in a variety of media to facilitate their use. "Media" refers to a manufacture that contains the expression repertoire information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure may be chosen, based on the means used to access the stored information. A variety of data processor programs and formats can be used for storage, e.g. word processing text file, database format, etc.

As used herein, "a computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

A variety of structural formats for the input and output means can be used to input and output the information in the computer-based systems of the present invention. Such presentation provides a skilled artisan with a ranking of similarities and identifies the degree of similarity contained in the test expression repertoire.

A scaled approach may also be taken to the data analysis. For example, Pearson correlation of the repertoire results can provide a quantitative score reflecting the signature for each sample. The higher the correlation value, the more the sample resembles a reference repertoire. A negative correlation value indicates the opposite behavior. The threshold for the classification can be moved up or down from zero depending on the clinical goal.

To provide significance ordering, the false discovery rate (FDR) may be determined. First, a set of null distributions of dissimilarity values is generated. In one embodiment, the values of observed repertoires are permuted to create a sequence of distributions of correlation coefficients obtained out of chance, thereby creating an appropriate set of null distributions of correlation coefficients (see Tusher et al. (2001) PNAS 98, 5118-21, herein incorporated by reference). The set of null distribution is obtained by: permuting the values of each repertoire for all available repertoires; calculating the pairwise correlation coefficients for all repertoire results; calculating the probability density function of the correlation coefficients for this permutation; and repeating the procedure for N times, where N is a large number, usually 300. Using the N distributions, one calculates an appropriate measure (mean, median, etc.) of the count of correlation coefficient values that their values exceed the value (of similarity) that is obtained from the distribution of experimentally observed similarity values at given significance level.

The FDR is the ratio of the number of the expected falsely significant correlations (estimated from the correlations greater than this selected Pearson correlation in the set of randomized data) to the number of correlations greater than this selected Pearson correlation in the empirical data (significant correlations). This cut-off correlation value may be applied to the correlations between experimental repertoires.

Using the aforementioned distribution, a level of confidence is chosen for significance. This is used to determine the lowest value of the correlation coefficient that exceeds the result that would have obtained by chance. Using this method, one obtains thresholds for positive correlation, negative correlation or both. Using this threshold(s), the user can filter the observed values of the pairwise correlation coefficients and eliminate those that do not exceed the threshold(s). Furthermore, an estimate of the false positive rate can be obtained for a given threshold. For each of the individual "random correlation" distributions, one can find how many observations fall outside the threshold range. This procedure provides a sequence of counts. The mean and the standard deviation of the sequence provide the average number of potential false positives and its standard deviation.

The data can be subjected to non-supervised hierarchical clustering to reveal relationships among repertoires. For example, hierarchical clustering may be performed, where the Pearson correlation is employed as the clustering metric. Clustering of the correlation matrix, e.g. using multidimensional scaling, enhances the visualization of functional homology similarities and dissimilarities. Multidimensional scaling (MDS) can be applied in one, two or three dimensions.

The analysis may be implemented in hardware or software, or a combination of both. In one embodiment of the invention, a machine-readable storage medium is provided, the medium comprising a data storage material encoded with machine readable data which, when using a machine programmed with instructions for using said data, is capable of displaying a any of the datasets and data comparisons of this invention. Such data may be used for a variety of purposes, such as drug discovery, analysis of interactions between cellular components, and the like. In some embodiments, the invention is implemented in computer programs executing on programmable computers, comprising a processor, a data storage system (including volatile and non-volatile memory and/or storage elements), at least one input device, and at least one output device. Program code is applied to input data to perform the functions described above and generate output information. The output information is applied to one or more output devices, in known fashion. The computer may be, for example, a personal computer, microcomputer, or workstation of conventional design.

Each program can be implemented in a high level procedural or object oriented programming language to communicate with a computer system. However, the programs can be implemented in assembly or machine language, if desired. In any case, the language may be a compiled or interpreted language. Each such computer program can be stored on a storage media or device (e.g., ROM or magnetic diskette) readable by a general or special purpose programmable computer, for configuring and operating the computer when the storage media or device is read by the computer to perform the procedures described herein. The system may also be considered to be implemented as a computer-readable storage medium, configured with a computer program, where the storage medium so configured causes a computer to operate in a specific and predefined manner to perform the functions described herein.

A variety of structural formats for the input and output means can be used to input and output the information in the computer-based systems of the present invention. One format for an output tests datasets possessing varying degrees of similarity to a trusted repertoire. Such presentation provides a skilled artisan with a ranking of similarities and identifies the degree of similarity contained in the test repertoire.

Storing and Transmission of Data

Further provided herein is a method of storing and/or transmitting, via computer, sequence, and other, data collected by the methods disclosed herein. Any computer or computer accessory including, but not limited to software and storage devices, can be utilized to practice the present invention. Sequence or other data (e.g., immune repertoire analysis results), can be input into a computer by a user either directly or indirectly. Additionally, any of the devices which can be used to sequence DNA or analyze DNA or analyze immune repertoire data can be linked to a computer, such that the data is transferred to a computer and/or computer-compatible storage device. Data can be stored on a computer or suitable storage device (e.g., CD). Data can also be sent from a computer to another computer or data collection point via methods well known in the art (e.g., the internet, ground mail, air mail). Thus, data collected by the methods described herein can be collected at any point or geographical location and sent to any other geographical location.

Reagents and Kits

Also provided are reagents and kits thereof for practicing one or more of the above-described methods. The subject reagents and kits thereof may vary greatly. Reagents of interest include reagents specifically designed for use in production of the above described immune repertoire analysis. For example, reagents can include primer sets for cDNA synthesis, for PCR amplification and/or for high throughput sequencing of a class or subtype of immunological receptors. Gene specific primers and methods for using the same are described in U.S. Pat. No. 5,994,076, the disclosure of which is herein incorporated by reference. Of particular interest are collections of gene specific primers that have at least 2, 5, 10, 15, 20, 30, 40, 50, 60, 70, 80, 90, 100, 200, 300, 400, 500, 600, 700, 800, 900, 1000 primer sets or more. The gene specific primer collections can include only primers for immunological receptors, or they may include primers for additional genes, e.g., housekeeping genes, controls, etc.

The kits of the subject invention can include the above described gene specific primer collections. The kits can further include a software package for statistical analysis, and may include a reference database for calculating the probability of a match between two repertoires. The kit may include reagents employed in the various methods, such as primers for generating target nucleic acids, dNTPs and/or rNTPs, which may be either premixed or separate, one or more uniquely labeled dNTPs and/or rNTPs, such as biotinylated or Cy3 or Cy5 tagged dNTPs, gold or silver particles with different scattering spectra, or other post synthesis labeling reagent, such as chemically active derivatives of fluorescent dyes, enzymes, such as reverse transcriptases, DNA polymerases, RNA polymerases, and the like, various buffer mediums, e.g. hybridization and washing buffers, prefabricated probe arrays, labeled probe purification reagents and components, like spin columns, etc., signal generation and detection reagents, e.g. streptavidin-alkaline phosphatase conjugate, chemifluorescent or chemiluminescent substrate, and the like.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed, site. Any convenient means may be present in the kits.

The above-described analytical methods may be embodied as a program of instructions executable by computer to perform the different aspects of the invention. Any of the techniques described above may be performed by means of software components loaded into a computer or other information appliance or digital device. When so enabled, the computer, appliance or device may then perform the above-described techniques to assist the analysis of sets of values associated with a plurality of genes in the manner described above, or for comparing such associated values. The software component may be loaded from a fixed media or accessed through a communication medium such as the internet or other type of computer network. The above features are embodied in one or more computer programs may be performed by one or more computers running such programs.

Software products (or components) may be tangibly embodied in a machine-readable medium, and comprise instructions operable to cause one or more data processing apparatus to perform operations comprising: a) clustering sequence data from a plurality of immunological receptors or fragments thereof; and b) providing a statistical analysis output on said sequence data. Also provided herein are software products (or components) tangibly embodied in a machine-readable medium, and that comprise instructions operable to cause one or more data processing apparatus to perform operations comprising: storing sequence data for more than $10^2$, $10^3$, $10^4$, $10^5$, $10^6$, $10^7$, $10^8$, $10^9$, $10^{10}$, $10^{11}$, or $10^{12}$ immunological receptors or more than $10^2$, $10^3$, $10^4$, $10^5$, $10^6$, $10^7$, $10^8$, $10^9$, $10^{10}$, $10^{11}$, or $10^{12}$ sequence reads.

In some examples, a software product (or component) includes instructions for assigning the sequence data into V, D, J, C, VJ, VDJ, VJC, VDJC, or VJ/VDJ lineage usage classes or instructions for displaying an analysis output in a multi-dimensional plot. In some cases, a multidimensional plot enumerates all possible values for one of the following: V, D, J, or C. (e.g., a three-dimensional plot that includes one axis that enumerates all possible V values, a second axis that enumerates all possible D values, and a third axis that enumerates all possible J values). In some cases, a software product (or component) includes instructions for identifying one or more unique patterns from a single sample correlated to a condition. The software product (or component0 may also include instructions for normalizing for amplification bias. In some examples, the software product (or component) may include instructions for using control data to normalize for sequencing errors or for using a clustering process to reduce sequencing errors. A software product (or component) may also include instructions for using two separate primer sets or a PCR filter to reduce sequencing errors.

EXAMPLES

The following examples are offered by way of illustration and not by way of limitation.

Example 1: High-Throughput Sequencing of the Zebrafish Antibody Repertoire

High-throughput sequencing of the variable domain of the antibody heavy chain from 14 zebrafish was performed in order to analyze VDJ usage and antibody sequence. Zebrafish were found to use between 50 and 86% of all possible VDJ combinations and shared a similar frequency distribution, with some correlation of VDJ patterns between individuals. Zebrafish antibodies retained a few thousand unique heavy chains that also exhibited a shared frequency distribution. There was evidence of convergence, in which different individuals made the same antibody. This approach provides insight into the breadth of the expressed antibody repertoire and immunological diversity at the level of an individual organism.

Zebrafish are an ideal model system for studying the adaptive immune system because in evolutionary terms they have the earliest recognizable adaptive immune system whose features match the essential human elements. Like humans, zebrafish have a recombination activating gene (RAG) and a combinatorial rearrangement of V, D, and J gene segments to create antibodies. They also have junctional diversity during recombination and somatic hypermutation of antibodies to improve specificity, and the organization of their immunoglobulin (Ig) gene loci approximates that of human. In addition, the zebrafish immune system has only ~300,000 antibody-producing B cells, making it three orders of magnitude simpler than mouse and five orders simpler than human in this regard.

The antibody repertoire of zebrafish was characterized by analyzing complementarity-determining region 3 (CDR3) of the heavy chain, which contains the vast majority of immunoglobulin diversity and can be captured in a single sequencing read (FIG. 1). The 454 GS FLX high-throughput pyrosequencing technology allowed sequencing of 640 million bases of zebrafish antibody cDNA from 14 zebrafish in four families (FIG. 1B). Zebrafish were raised in separate aquaria for each family and were allowed to have normal interactions with the environment, including the development of natural internal flora. Analysis was performed on the quiescent state of the immune system, a state where the zebrafish had sampled a complex but fairly innocuous environment and had established an equilibrium of normal immune function. mRNA was prepared from whole fish, and we synthesized cDNA using primers designed to capture the entire variable region.

Between 28,000 and 112,000 useful sequencing reads were obtained per fish, and analysis was focused on CDR3 sequences. Each read was assigned V and J by alignment to a reference with a 99.6% success rate (table S3); failures were due to similarity in some of the V gene segments. D was determined for each read by applying a clustering algorithm to all of the reads within a given VJ and then aligning the consensus sequence from each cluster to a reference. D was assigned to 69.6% of reads; many of the unassignable cases had D regions mostly deleted. Both the isotypes that are known to exist in zebrafish (IgM and IgZ) were found, and their relative abundance agrees with previous studies (12). Our analysis focused on IgM, which is the most abundant species; IgZ data are presented in figs. S3 and S4 (13).

There are 975 possible VDJ combinations in zebrafish (39 V×5 D×5 J=975 VDJ). In any given fish, the VDJ combination coverage was at least 50% and in some cases at least 86% (FIG. 2). By using subsets of the full data set to perform rarefaction studies, we demonstrated that our sampling of the VDJ repertoire was asymptoting toward saturation (FIG. 3A). Any VDJ classes that may be missing from the data are occurring at frequencies below $10^{-4}$ to $10^{-5}$. There was a commonality to the frequency distributions of VDJ usage that was independent of the specific VDJ repertoire for individual fish (FIG. 3B). Specifically, the majority of VDJ combinations in each fish were of low abundance, but a similarly small fraction—although different combinations for different fish—were found at high frequencies. This distribution could be used to constrain theoretical models of repertoire development.

The VDJ repertoire is a vector in which each element records the number of reads that map to a particular VDJ class. The dot product between VDJ repertoire vectors measures the degree of correlation between different fish (table 5 and FIG. 3C).

Most fish were uncorrelated in their VDJ repertoires; however, some fish were highly correlated, and three pairs of fish had correlation coefficients in the range 0.62 to 0.75. Some of these correlations appear to derive from the largest VDJ class in the repertoire (table 5A and FIG. 3C). When the fish-fish VDJ correlations were computed in the absence of the largest VDJ class, the largest correlations disappeared, but a new set of correlations appeared between a larger fraction of the fish (table 5B and FIG. 3D). These correlations were mostly weaker than the previous correlations but still well above the statistical noise.

A model for random VDJ repertoire assembly was then created using simulated VDJ distributions that replicated the actual measured distributions and coverage fractions. The correlations in these simulated VDJ repertoires are all near zero, and the probability of two fish having a highly correlated random repertoire is less than $10^{-6}$ (FIGS. 3, C and D). Thus, even though the VDJ repertoire is believed to be generated by a series of random molecular events within independent individual cells, in zebrafish the VDJ repertoire appears substantially structured and nonrandom on a global scale. It is possible that the source of this structure is simply convergent evolution, that the fish see a similar enough environment that selection in their quiescent immune systems converges to correlated VDJ usage. It is also possible that this distribution reflects bias in the VDJ recombination mechanisms, which would have important implications for antibody diversity space and would suggest that the number of solutions to a given antigen recognition problem, or at least the number that are readily evolvable, may be much smaller than previously assumed.

Summarizing the VDJ repertoire with a simple count of the number of different VDJ combinations neglects the variation in abundance of different VDJ species. Ecologists have the same problem in characterizing species diversity; they refer to the counting approach as species richness and have developed other methods to characterize variation of abundance, which they term "heterogeneity". The most popular approach to characterize heterogeneity is based on information theory, specifically the Shannon-Weaver entropy, which summarizes the frequency distribution in a single number. The VDJ repertoire entropies generally varied between 3.1 and 7.7 bits for individual fish. Exponentiating the entropy indicates the effective size of the VDJ repertoire, and this varied between 9 and 200 with an average of 105, or an average effective VDJ repertoire coverage of about 9%. This can be interpreted as the fraction of highly expressed VDJ classes.

Whereas the VDJ repertoire provides a coarse view of immunological diversity, each VDJ class can contain a large number of distinct individual antibodies that differ as a result of hypermutations and junctional changes. The antibody repertoire was characterized by using quality threshold clustering of Smith-Waterman alignments to group similar reads together; each cluster defining an antibody. Performing this analysis on control data with well-defined sequence clones allowed calibration of the clustering algorithm and separation of true hypermutation diversity from sequencing errors. Many VDJ combinations included a large number of distinct antibodies. The overall distribution of the abundances of the antibodies followed an apparent power law with scaling parameter 2.2, and this was consistent among all fish over two decades (FIG. 4B). This behavior may represent an important signature of the underlying dynamics of the adaptive immune system. It was not observed for either the control data or the VDJ distributions, and thus we ruled out the possibility that it is an artifact of polymerase chain reaction (PCR) bias.

There are several ways to use this data to estimate the number of unique antibodies per fish. The first is to perform rarefaction studies and determine whether the number of independent clusters tends to saturate. Results indicated that the saturation occurs at between ~1200 and 3500 unique antibodies per fish (FIG. 4A). Another way is by applying approaches used in ecology to estimate population sizes and diversity—sample and resample techniques. This yielded an estimate of between 1200 and 3700 unique antibodies per fish, whether applied blindly or using knowledge of the antibody abundance distributions (FIG. 4C). Both approaches are lower bounds on the true antibody diversity because antibodies that differ by only one or two mutations will be incorporated into the same cluster. This effect was corrected for by reanalyzing the data within each cluster with zero error tolerance, only matching exact reads. The largest clusters each had several subclusters with more than two reads each, and the control sequence data indicated that probably half of those clusters are real while the other half are artifacts due to sequencing error. By combining this stringent method of finding small differences in common sequences with the more permissive method of clustering rare sequences with less similarity together (thereby having tolerance to sequencing errors on rare transcripts), The upper limit of heavy-chain antibody diversity is within 50% of the lower bound estimates, or between 5000 and 6000 antibodies in an individual fish.

In order to determine how often repertoires converged to the same antibody, we searched for sequences that are shared between fish. Although there were no antibodies common to all fish, some antibodies were shared between smaller groups of fish (FIG. 4D). These cases of convergent evolution were more frequent than one would expect from a random usage model, with P values as low as $10^{-15}$. Unexpectedly, different individuals shared heavy chains that were identical in the region we sequenced, even up to hypermutation. Specifically, there were 254 unique sequences shared between two fish and 2 unique sequences shared between five fish. These data illustrate the powerful forces of selection and perhaps can be used to estimate evolutionary dynamics in this system.

The abundance distributions of both the VDJ repertoire and antibody heavy-chain diversity were similar between individuals, that VDJ usage is not uniform, that individuals can have highly correlated VDJ repertoires, and that convergent evolution of identical heavy-chain sequences is unexpectedly common.

Similar measurements are made on mice and humans. These organisms use the same molecular mechanisms for repertoire generation as fish, and thus can be similarly profiled.

Methods

Zebrafish.

14 six-month-old wild type WIK zebrafish were collected from 4 different families. Fish were euthanized according to an animal protocol approved by the Stanford University administrative panel on laboratory animal care and snap frozen in liquid nitrogen and stored in −80° C. Fish gender was determined by scoring the morphological traits and confirmed by quantifying the differential expression level of two splice variants of the vasa gene as previously described.

mRNA Preparation.

Each whole fish was homogenized in the presence of TRIzol® Reagent using a TissueLyzer (Qiagen, Valencia, Calif.). Total RNA from each fish was purified using TRIzol® Plus RNA Purification System (Invitrogen, Carlsbad, Calif.). The mRNA was further purified using Oligotex mRNA Kit (Qiagen, Valencia, Calif.). Manufacture's protocols were followed during these processes and the concentrations of the total RNA and the mRNA were determined using a Nanodrop spectrophotometer.

Primer Design.

The zebrafish heavy-chain locus was previously described by Danilova et al (Danilova, Hohman et al. 2000; Danilova, Bussmann et al. 2005). The consensus leader sequences for 39 functional V gene segments of the zebrafish heavy-chain were used to design the 27 forward primers (set number 2). The first 100 bp of the IgM and IgZ constant domain were used to design the reverse primers. A second, independent primer set, based on the consensus leader and frame region 1 sequences, was designed in order to test PCR bias. Gene specific primers were also designed for the reverse transcription step; these were located about 50 bp downstream from the PCR reverse primers.

cDNA Synthesis and PCR.

cDNA was synthesized using SuperScript™ III reverse transcriptase (Invitrogen, Carlsbad, Calif.). A quarter of the total mRNA purified from each fish was split into 8 cDNA synthesis reactions with both the primers for IgM and IgZ constant regions and SUPERase•In™ (Ambion, Austin, Tex.). RNase H (Invitrogen Carlsbad, Calif.) was added to each reaction to remove RNA at the end of the cDNA synthesis step. All enzyme concentrations, reaction volumes and the incubation temperature were based on the manufacturer's protocol for synthesis of cDNA from up to 500 ng of mRNA using gene specific primers.

Each cDNA synthesis reaction (20 µl) was split into two PCR reactions, and a total of 16 PCR reactions were set up for each fish. Each of the 27 forward primers was added so that each V segment was represented by a final concentration of 200 nM primer. Since some primers covered multiple V gene segments, their concentration was in proportion to the number of V segments. Both reverse primers were added at a concentration of 7.8 µM. The PCR program began with an initial denaturation at 94° C. for 2 minutes, followed by 28 cycles of denaturation at 94° C. for 30 s, annealing of primer to DNA at 60° C. for 30 s, and extension by Platinum® Taq DNA Polymerase High Fidelity (Invitrogen, Carlbad, Calif.) at 68° C. for 2 minutes. PCR products were cleaned using QIAquick PCR Purification Kit (Qiagen, Valencia, Calif.) and the concentration was measured using the nanodrop spectrophotometer.

TABLE 1

Sequencing primer set 2

| SEQ ID | Name | Sequence | V gene segment | V gene segment amplicon (bp) |
| --- | --- | --- | --- | --- |
| SEQ ID NO: 1 | ZVH 4-1 | TGGTCTCCTCTGCCTTTTGT | 5.3 | 362 |
| SEQ ID NO: 2 | ZVH 4-2 | AACCATGATCGCCTCATCTC | 5.4, 5.8 | 362, 359 |
| SEQ ID NO: 3 | ZVH 4-3 | GATGGCAACAACATCCTGTG | 7.1 | 314 |
| SEQ ID NO: 4 | ZVH 4-4 | TGCATTTCAGTTCTGCTGCT | 8.2, 8.3, 8.4 | 346, 343, 343 |
| SEQ ID NO: 5 | ZVH 4-5 | ACGAATGCAGGAGTCAGACA | 4.1 | 307 |
| SEQ ID NO: 6 | ZVH 4-6 | TGTTTCAACTGTTCGTGGTCA | 1.1, 1.2 | 310, 311 |
| SEQ ID NO: 7 | ZVH 4-7 | TGGAGTTGTGTTGATGATGATT | 1.3 | 326 |
| SEQ ID NO: 8 | ZVH 4-8 | TTCATATGCACATGGTCAGTCA | 1.4 | 302 |
| SEQ ID NO: 9 | ZVH 4-9 | TGTGGTGATTGTCTTTCAAGG | 2.1, 2.2 | 349, 332 |
| SEQ ID NO: 10 | ZVH 4-10 | TGGAAAAGGAGTCAAAAAGCAT | 2.3 | 386 |
| SEQ ID NO: 11 | ZVH 4-11 | GCTTTTGTCATGTTTGCTCTCA | 3.2 | 331 |
| SEQ ID NO: 12 | ZVH 4-12 | GCTTACTGCTGCTCTCATTCAG | 4.3, 4.8, 4.9 | 339, 339, 336 |
| SEQ ID NO: 13 | ZVH 4-13 | TTTCTGCTGCTGTGCTTTAC | 4.5, 4.7 | 343, 334 |
| SEQ ID NO: 14 | ZVH 4-14 | CTGCTGTTTTCATTGGCCTTA | 4.1 | 337 |
| SEQ ID NO: 15 | ZVH 4-15 | GGTTTATACTGTCAAGGCATGG | 4.2 | 307 |
| SEQ ID NO: 16 | ZVH 4-16 | CAGCCTCAAGATGAAGAATGC | 4.6 | 350 |
| SEQ ID NO: 17 | ZVH 4-17 | CTAGTGCTGTTTCTGGCAGT | 5.1, 5.7 | 328, 328 |
| SEQ ID NO: 18 | ZVH 4-18 | CATGATCACCTCATCTCTCTGC | 5.2, 5.5 | 356, 359 |
| SEQ ID NO: 19 | ZVH 4-19 | CATGATTCTGAGCATTTTATCATGT | 6.1 | 329 |
| SEQ ID NO: 20 | ZVH 4-20 | CAATAATCAACTCACTCCTGCTG | 6.2 | 345 |

TABLE 1-continued

Sequencing primer set 2

| SEQ ID | Name | Sequence | V gene segment | V gene segment amplicon (bp) |
|---|---|---|---|---|
| SEQ ID NO: 21 | ZVH 4-21 | CTGCGTCCAGTGTATATTCCA | 8.1 | 315 |
| SEQ ID NO: 22 | ZVH 4-22 | TGTATTGACTGTCAGGTTGTGC | 9.2, 9.4 | 304, 304 |
| SEQ ID NO: 23 | ZVH 4-23 | TCTTTCTGCAGTTGGCAG | 9.1, 9.3 | 330, 334 |
| SEQ ID NO: 24 | ZVH 4-24 | TCTCAAAGTTGTTGGTGTCAGA | 10.1 | 313 |
| SEQ ID NO: 25 | ZVH 4-25 | CTCTCTAAACAAGTGCAAAGGTC | 11.1 | 321 |
| SEQ ID NO: 26 | ZVH 4-26 | TGGACCTTAAACTTAACTGTCTG | 11.2 | 360 |
| SEQ ID NO: 27 | ZVH 4-27 | CCATATGTTTCTGGCATCTCCC | 13.2 | 308 |
| SEQ ID NO: 28 | C5 | TGCACTGAGACAAACCGAAG | C-μ | N/A |
| SEQ ID NO: 29 | C6 | TCAGAGGCCAGACATCCAAT | C-ζ | N/A |
| SEQ ID NO: 30 | VhuCc5 | TGATTGACCCATCAGAACCA | C-μ | N/A |
| SEQ ID NO: 31 | VhzCc6 | GAATGCTGGGTGACGTTTTT | C-ζ | N/A |

TABLE 2 sequencing primer set 1

| SEQ ID | Index | Sequence | V gene segment | V gene segment amplicon (bp) |
|---|---|---|---|---|
| SEQ ID NO: 1 | 1 | TGGTCTCCTCTGCCTTTTGT | 5.3 | 362 |
| SEQ ID NO: 32 | 2 | GTCTGGAGTCCATCCCTTCA | 4.5, 4.7 | 297, 297 |
| SEQ ID NO: 3 | 3 | GATGGCAACAACATCCTGTG | 7.1 | 314 |
| SEQ ID NO: 4 | 4 | TGCATTTCAGTTCTGCTGCT | 8.2, 8.3, 8.4 | 346, 343, 343 |
| SEQ ID NO: 33 | 5 | ATTGTCTTGAGGCCTGGTCA | 5.2, 5.4, 5.5, 5.8 | 271, 274, 274, 271 |
| SEQ ID NO: 34 | 6 | ACCTGTGCATGCAGTGGATT | 9.1, 9.3 | 229, 233 |
| SEQ ID NO: 35 | 7 | CTGTGCCTGCAGTGGATTTA | 9.2, 9.4 | 227, 227 |
| SEQ ID NO: 36 | 8 | TCATCAAACCAGGCAATGAA | 11.1, 11.2 | 271, 270 |
| SEQ ID NO: 37 | 9 | TGGAGTCGATTGAAAGCTCA | 4.3, 4.8, 4.9 | 291, 291, 288 |
| SEQ ID NO: 38 | 10 | CGTCCTGATGACTCTCTCACTATC | 5.1, 5.7 | 256, 256 |
| SEQ ID NO: 39 | 11 | TGTGACAAAGAGACCTGGAGAA | 2.1, 2.2, 2.3 | 289, 272, 286 |
| SEQ ID NO: 40 | 12 | GTTTCTGGACTCTCCCTTGC | 1.4 | 220 |
| SEQ ID NO: 41 | 13 | CAATCTCTGGATTCGGTGGT | 3.2 | 228 |
| SEQ ID NO: 42 | 14 | TTTCCTGTAGGGGATCAGGA | 4.1 | 240 |
| SEQ ID NO: 43 | 15 | GCCTGGAGAAACTCTGACTCTG | 4.2, 4.3, 4.6, 4.8 | 257, 260, 245, 260 |
| SEQ ID NO: 2 | 16 | AACCATGATCGCCTCATCTC | 5.4, 5.8 | 362, 359 |
| SEQ ID NO: 44 | 17 | AACCAGGAGAGTCCCATTCA | 6.1 | 261 |
| SEQ ID NO: 45 | 18 | CTGGTATGTACCGCCTCTGG | 6.2 | 241 |
| SEQ ID NO: 46 | 19 | CTGTGGTGAAAAGACCAGGAG | 1.1, 1.2, 1.3 | 269, 270, 267 |

TABLE 2-continued sequencing primer set 1

| SEQ ID | Index | Sequence | V gene segment | V gene segment amplicon (bp) |
|---|---|---|---|---|
| SEQ ID NO: 47 | 20 | CTGAGGCAGTGACCATCAAA | 10.1 | 279, |
| SEQ ID NO: 48 | 21 | TCCCCTGCACAGATTAAAGC | 13.2 | 278 |
| SEQ ID NO: 49 | 22 | TGCAGGAGTCAGACACTGGT | 14.1 | 302 |

454 library preparation and sequencing. About 2 μg of QIAquick cleaned PCR product for each fish was used to start the 454 library preparation process. AMPure SPRI beads (Agencourt, Beverly, Mass.) were used to concentrate PCR product and remove the remaining primers. 454 FLX DNA library construction protocol was followed for all samples. Briefly, double stranded DNA was end polished and ligated to sequencing adaptors which contained a molecular identifier (MID, a nucleotide based barcode system). This allowed us to multiplex the sequencing plate and also served as an internal control. The rest of the Roche 454 protocol was followed which includes library immobilization, fill-in reaction and single stranded template DNA (sstDNA) library isolation. The sstDNA was quantified using a digital-PCR method developed in our lab (White R. A. 2009), which gave the absolute count of DNA molecules in the library. This allowed us to eliminate the manufacturer's suggested titration run. 16 emulsion PCR reactions were prepared for each fish with a ratio of 0.3 molecules per DNA capture bead. Two-region masks were used on the sequencing plate.

Control Library Construction.

Figure 5B:
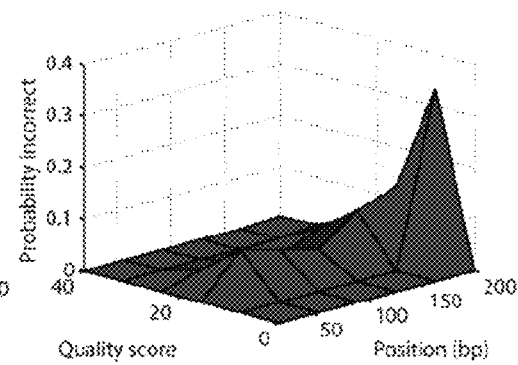
Figure 6A:
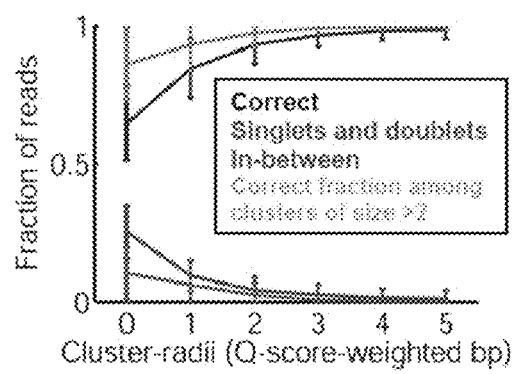
FIG. 6A-6B. Effect of Cluster radii on the control library of 35 PCR cycles. We examine the "correct" cluster's representation among the "incorrect" clusters formed by orphan reads aligning to the same template sequence as a function of the cluster radii.
Figure 6B:
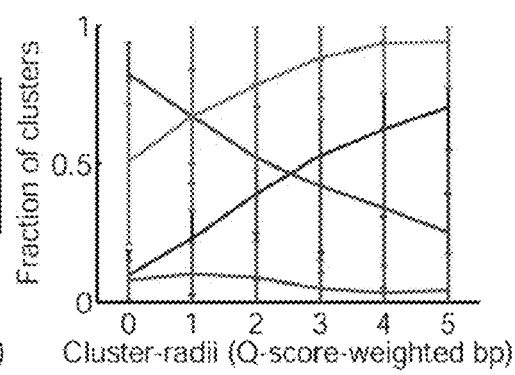
Figure 7A:
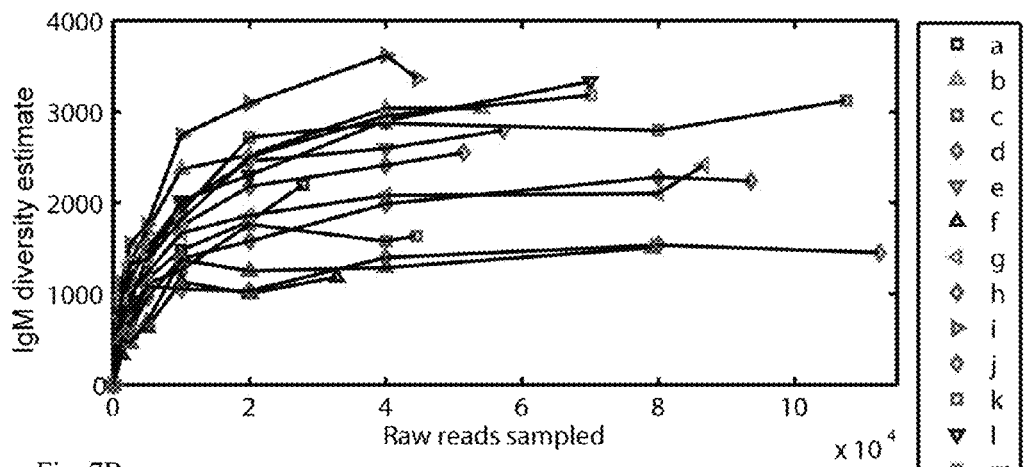
FIG. 7A-7B. Rarefaction of diversity estimates (estimate 2 from FIG. 4C) for both IgM and IgZ in all 14 fish.
Figure 7B:
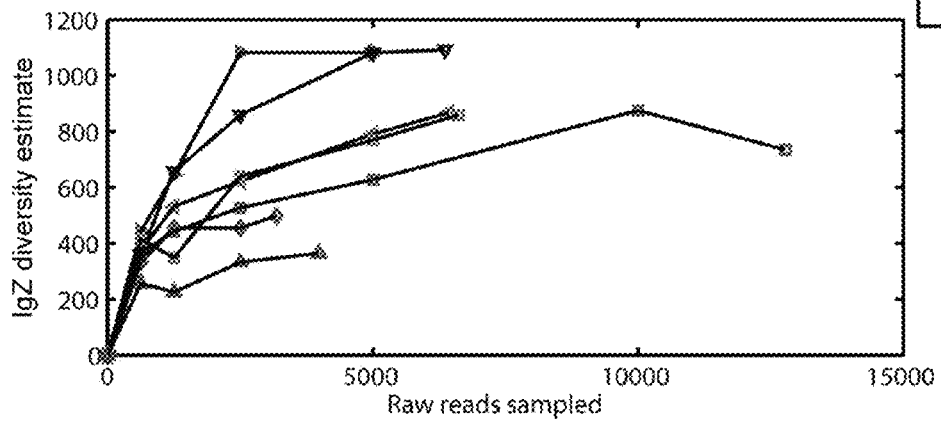
Figure 8:
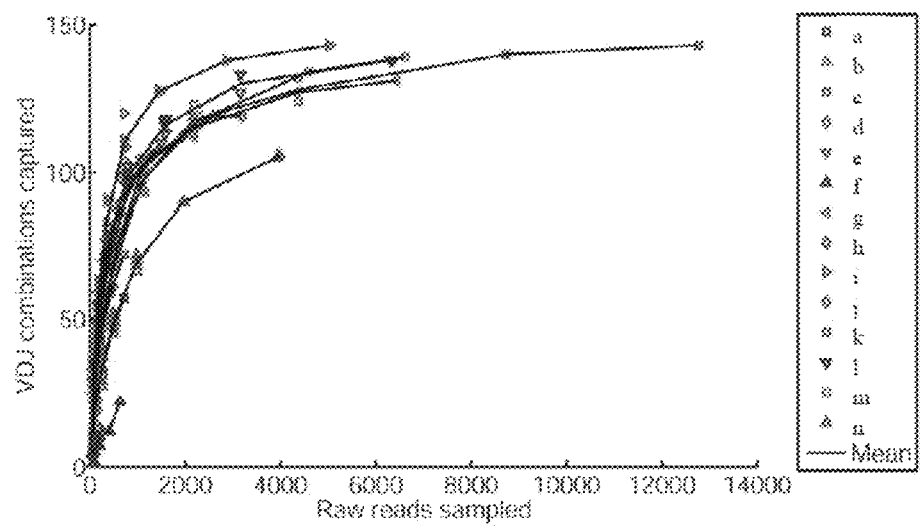
FIG. 8. VDzJz combinations captured as a function of reads sampled for IgZ in all 14 fish.

We performed control experiments using a mixture of cloned immunoglobulin genes that covered all possible V gene segments. The degree of PCR bias introduced in the sample preparation and sequencing process was estimated by comparing the representation of the known clones before and after PCR, and the bias introduced is about 3-fold up or down from the mean, depending on the specific primer. In the quantitative analyses that follow, these measured biases were used to normalize the data. We also used the control data to measure sequencing errors; the overall per base error rate is about 0.25% without PCR and 0.4% after 35 rounds of PCR. (FIG. 5) The effects of sequencing error are mitigated by the clustering process which allows one to determine a consensus sequence by grouping several reads together, and thus average out the error. The clustering algorithm was tested on the control data in order to validate parameter choices, and we found parameters that resulted in 97% of the reads being put into the correct clusters while allowing at most 3 deviations from the consensus sequence per read (FIG. 6).

PCR product from a zebrafish was cloned using TOPO® TA Cloning Kit for Sequencing (Invitrogen, Carlbad, Calif.). 38 clones for IgM and 35 clones for IgZ containing different V gene segments were picked and plasmids were purified and sequenced using the Applied Biosystems 3730xl DNA Analyzer (Sequetech, Mountain View, Calif.). 73 plasmids were pooled in equal amount to generate a master mix. This master mix was used as the template to generate PCR product, with samples taken at 0, 15, 25, and 35 cycles. For 0 cycle (unamplified) product, a restriction endonuclease (EcoRI, New England Biolabs, Ipswich, Mass.), was used to digest the plasmid. EcoRI sites only exist on the vector, which is 11 bp away from both sides of the insertion, and do not exist in any of the templates. The insertion was separated from the rest of the vector by running on a 2% agarose gel and excising a band corresponding to 200 to 600 bp, and purified using QIAquick Gel Extraction Kit (Qiagen, Valencia, Calif.). These four libraries went through the same 454 library preparation procedures described above using MIDs and were pooled and sequenced.

Informatics Pipeline.

For rapid analysis of sequenced reads, we developed a core algorithm to align, cluster, find consensus sequences, and measure distributions of important parameters. For tasks such as visual representation, the core algorithm's output worked together with short MATLAB subroutines (both the compiled core algorithm, and all subroutines used in this paper are available upon request). Sequenced reads were filtered for those encompassing the CDR3 and truncated by size to 200 bp. The first 10 bp, corresponding the 454 barcode, were removed. Reads were then aligned to V- and J-exons using the Smith-Waterman algorithm (Smith and Waterman 1981). After partitioning each V/J combinatorial match into its own subset, weighted pairwise Hamming distances (see Control run and its analysis) were assigned again by the Smith-Waterman algorithm. Identical sequences were grouped, and clusters of nonzero radius were formed using an implementation of the quality threshold (QT) method described by Heyer et al (Heyer, Kruglyak et al. 1999). Our implementation, applied to control data in FIG. 6, chose read i as a cluster seed if it held the maximum "adjacency" (defined by the sum $\Sigma j \exp(-dij)$, with dij being the distances between all sequences j≠i) among all as-yet unclustered sequences. On each iteration of cluster growth, a read entered the cluster if and only if it minimally increased the cluster's diameter (ie the maximum distance between any two cluster members). Once a further read addition required increasing the cluster diameter beyond the pre-set diameter threshold (twice the radius plotted in FIG. 6), cluster formation terminated.

Consensus sequences were assigned to a cluster using the most represented sequence within that cluster. D-segments and junctions were finally assigned and somatic mutations were counted (see VDJ and somatic mutation determination, below). In order to account for cases in which D-segments had insertions, deletions, or mutations beyond recognition, a sixth class of "ambiguous-D" segment was added to the VDJ diversity (see FIG. 2) for an "extended" repertoire of 39×6× 5=1170 combinations.

Control Run and its Analysis.

Sequencing error and sequence-specific bias constituted the largest obstacles in the way of characterizing the system accurately. To quantify these, we constructed two control libraries. We used each of the two primer sets to generate amplicons using different numbers of PCR cycles (0, 15, 25 and 35) and sequenced the products of each using the 454

FLX. We generated 4,500 to 5,000 reads from each PCR cycle sample. By aligning with Sanger-sequenced template sequences, we gauged error rates as functions of both quality scores and position relative to our sequencing primers (FIG. 5). We weighted sequence alignments accordingly for clustering.

We also used our control libraries to calibrate our measurements of VDJ abundance to what we could expect from PCR bias alone. By counting the number of occurrences of a given template at 0 cycles, and the same template at 35 cycles, we achieved a set of normalization coefficients that we used to renormalize the abundances of over- and under-represented VDJ combinations (see Bias parameter optimization and technical replicates). The vast majority of PCR bias occurred in the first 15 cycles, and the bias remained stable up to 35 cycles.

Various thresholds were applied to test the sensitivity of the clustering algorithm. We examined the fraction of reads being correctly assigned to a template (correct clusters), fraction of reads forming clusters that had only one or two reads (singlets and doublets), and fraction of reads in between clusters correctly assigned to a template (in-between clusters) as function of cluster radii. We found at cluster radius 3 that 96.6% of the reads were correctly assigned with 2.8% in singlet and doublet clusters and a further 0.6% in incorrectly assigned larger clusters. Thus, we consistently used three as the radius for other analyses and we required that each cluster have at least three reads to be included as an antibody; VDJ assignments are less ambiguous and we allowed individual reads for those analyses.

The power law observed in zebrafish antibody abundance data was not evident for either the control data or for the VDJ distributions, and thus we ruled out the possibility that it was an artifact of PCR bias.

Bias Parameter Optimization and Technical Replicates.

We designed a second, largely independent PCR primer set that allowed us to perform technical replicates on the same fish samples; in other words the same fish sample was amplified and sequenced with two different primer sets, and then the correlation between the two measurements was calculated. These technical replicates show a high degree of correlation for a given fish (average R2=0.91), and very low correlation between fish (table 4), validating the quantitative analysis.

Un-normalized. 38 V-exons

|    | a2     | b2     | c2     | d2     | e2     | f2     |
|----|--------|--------|--------|--------|--------|--------|
| a1 | 0.9361 | 0.2116 | 0.0209 | 0.3017 | 0.0447 | 0.0144 |
| b1 | 0.0498 | 0.699  | 0.0012 | 0.0549 | 0.0091 | 0.0047 |
| c1 | 0.1195 | 0.1114 | 0.8405 | 0.1262 | 0.0373 | 0.013  |
| d1 | 0.2422 | 0.2416 | 0.0108 | 0.8223 | 0.0335 | 0.3091 |
| e1 | 0.0353 | 0.0537 | 0.0014 | 0.0411 | 0.8167 | 0.0012 |
| f1 | 0.0123 | 0.0247 | −2E−04 | 0.3409 | 4E−05  | 0.984  |

Normalized. 38 V-exons

|    | a2     | b2     | c2     | d2     | e2     | f2     |
|----|--------|--------|--------|--------|--------|--------|
| a1 | 0.9932 | 0.2037 | 0.1123 | 0.3952 | 0.0769 | 0.0185 |
| b1 | 0.1556 | 0.9403 | 0.0741 | 0.2816 | 0.0646 | 0.0247 |
| c1 | 0.1457 | 0.1382 | 0.9745 | 0.2216 | 0.1922 | 0.0204 |
| d1 | 0.3084 | 0.2953 | 0.1208 | 0.8808 | 0.099  | 0.3536 |
| e1 | 0.0924 | 0.1405 | 0.1195 | 0.1821 | 0.926  | 0.0104 |
| f1 | 0.0177 | 0.034  | 0.0163 | 0.3995 | 0.007  | 0.9981 |

Regression residuals for linear fits on all normalized VDJ data

|       | a      | b      | c      | d      | e      | f      |
|-------|--------|--------|--------|--------|--------|--------|
| $R^2$ | 0.9864 | 0.8842 | 0.9497 | 0.7759 | 0.8574 | 0.9961 |

Replicate correlations of VDJ combinations with <25% counting error

|              | a      | b      | c      | d      | e      | f      |
|--------------|--------|--------|--------|--------|--------|--------|
| Un-normalized| 0.9419 | 0.7151 | 0.9484 | 0.8258 | 0.9155 | 0.9881 |
| Normalized   | 0.9938 | 0.941  | 0.9807 | 0.9532 | 0.9333 | 0.9989 |

Regression residuals for linear fits on normalized VDJ data with <25% counting error

|    | a      | b      | c      | d      | e      | f      |
|----|--------|--------|--------|--------|--------|--------|
| R2 | 0.9876 | 0.8865 | 0.9618 | 0.9086 | 0.871  | 0.9978 |

Table 4, Correlations and $R_2$ values on VDJ families for the two primer sets after the PCR bias normalization. Samples were prepared independently using two primer sets on the same 6 fish mRNA. 1—sequencing primer set 1, 2—sequencing primer set 2. Counting error for the ith VDJ combination with fractional representation $p_i$ is given by the binomial error $\sigma_i/(Np_i)=\sqrt{(1-p_i)/(Np_i)}$ where N is the total sample size.

Bias parameters were optimized using fish a through f, sequenced separately with two primer sets and control libraries generated from both of these primer sets. Since these six pairs of VDJ representations were independent trials with only the original cDNA library in common, bias normalization coefficients took account of all sequence-specific effects in sample preparation, from amplification and elsewhere (equal loading of the 0 cycle library showed this latter effect to cause no ore than 2-fold differences, well within what might be expected from either pipetting error or pectroscopic measurement of sample concentration).

Figure 9:
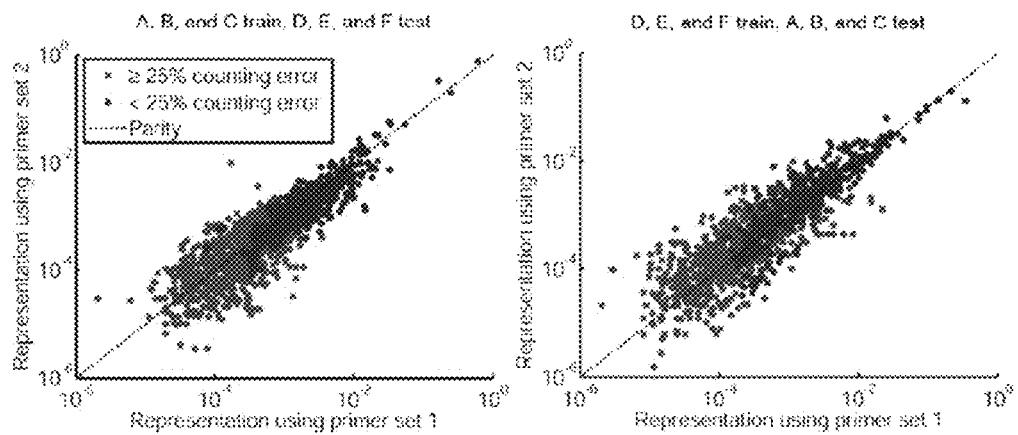
FIG. 9. Universal convergence of optimized bias parameters between different sets of training and test data. Each data point represents a single VDJ combination from one of the test fish.
Figure 10:
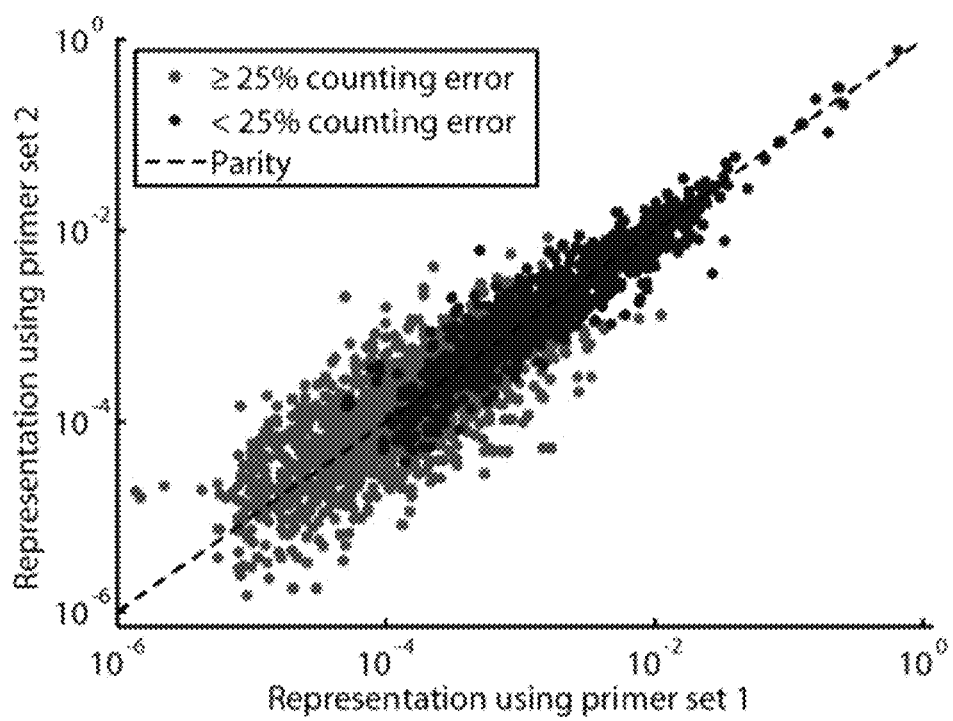
FIG. 10. VDJ representation obtained from two primer sets across six fish using optimized V-exon bias correction parameters.

Data was weighted by read count to minimize the effects of counting error. To illustrate the convergence of bias parameters, we took subsets of the fish data being used to constrain these estimates. As illustrated in FIG. 9, two independent fish subsets of three fish each provide sufficient information about the other subset's bias. Taking all six fish together, optimized bias parameters give the VDJ distribution illustrated in Supplementary FIG. 6, with strong statistical correlations and $R^2$ values (averaging 0.91) provided in Table 4.

VDJ and Somatic Mutation Determination.

Take the following raw sequence from fish c:

SEQ ID NO: 50:
agagactcttcaagcagcagcgtgactctgagtggacagaatatgcagac tgaggacacagctgtgtattattgcgccagagagaatagcgggggccagt actttgactactgggggaaaggaaccaaagtgacagtttcctcagctcaa ccatctgcgccccagtcagtcttcggtttgtctcagtgca It is aligned first to each V-exon to determine the optimal alignment. In this case Vh5.8 has nearly perfect alignment

```
                                               (SEQ ID NO: 50)
Observed   --------------agagactcttcaagcagcagcgtgactctga
                         |||||||||||||||||||||||||||||||

(SEQ ID NO: 51)
Vh5.8      gattcacagttagcagagactcttcaagcagcagcgtgactctga
Observed   gtggacagaatatgcagactgaggacacagctgtgtattattgcg
           |||||||||||||||||||||||||||||||||||||||||||||
Vh5.8      gtggacagaatatgcagactgaggacacagctgtgtattattgcg
Observed   ccagagaatagcggggccagtactttgactactgggggaaag
           ||||||||~.................................
Vh5.8      ccagagagt------------------------------------
Observed   gaaccaaagtgacagtttcctcagctcaaccatctgcgcccagt
           ............................................
Vh5.8      ---------------------------------------------
Observed   cagtcttcggtttgtctcagtgca
           ........................
Vh5.8      ------------------------
``` where the '.' character indicates a gap, the '~' character indicates a mismatch, and the '|' character indicates a match.

The segment starting at the first tail-mismatch is then aligned to all J segments and this gives:

```
                                               (SEQ ID NO: 52)
Observed   aatagcggggccagtactttgactactgggggaaaggaaccaaa
           ..........~|~|~|||||||||||||||||||||||||||||

(SEQ ID NO: 53)
Jh1        ----------actactactttgactactgggggaaaggaaccaaa
Observed   gtgacagtttcctcagctcaaccatctgcgcccagtcagtcttc
           |||||||||||||||.............................
Jh1        gtgacagtttcctcag----------------------------

Observed   ggtttgtctcagtgca
           ................
Jh1        ----------------
```

The final tail is assigned identity as the constant region, the last 20 bp being the Cm primer. The program then uses the J segment mismatches to determine the full D-segment. Given the options, this gives us the best alignment of:

```
                       (SEQ ID NO: 54)
       Observed   aatagcggggccag
                  ~|||||||||....
                       (SEQ ID NO: 55)
       Dh4        tatagcggggg----
``` with exon Dh4. The code then predicts the junctional regions such that none of the mismatches and gaps count as genuine mutations:

```
                                    (SEQ ID NO: 54)
       Adaptive   aatagcggggccag
                  x|||||||||xxxx
                                    (SEQ ID NO: 55)
       Naive      aatagcggggccag
``` where the 'x' character represents a junction. The predicted adaptive and naive sequences are then concatenated to the V's and J's to give a final "biological" alignment of

```
                                                                    (SEQ ID NO: 56)
Adaptive agagactcttcaagcagcagcgtgactctgagtggacagaatatgcagact
         |||||||||||||||||||||||||||||||||||||||||||||||||||
                                                                    (SEQ ID NO: 57)
Naive    agagactcttcaagcagcagcgtgactctgagtggacagaatatgcagact Adaptive gaggacacagctgtgtattattgcgccagagagaatagcggggccagtac
         ||||||||||||||||||||||||||||||||||x|||||||||xxxx|||
Naive    gaggacacagctgtgtattattgcgccagagagaatagcggggccagtac Adaptive tttgactactgggggaaaggaaccaaagtgacagtttcctcagctcaacca
         |||||||||||||||||||||||||||||||||||||||||||||||||||
Naive    tttgactactgggggaaaggaaccaaagtgacagtttcctcagctcaacca Adaptive tctgcgcccagtcagtcttcggtttgtctcagtgca
         ||||||||||||||||||||||||||||||||||||
Naive    tctgcgcccagtcagtcttcggtttgtctcagtgca
``` which has all transient mismatches and gaps removed.

The above sequence is taken to therefore be in its "naive" form with no mutations. Similar analysis applied to another such sequence from the same fish:

(SEQ ID NO: 50)
agagattcttccagcagcagcgtgactctgagtggacagaatatgcagag tgaggacacagctgtgtattattgcgccagagagagcatggagtggcgag cctttgattactggggaaagggaacaatggtcactgtcacatcagctcaa ccatctgcgcccagtcagtcttcggtttgtctcagtgca which we find corresponds well to genomic sequences Vh5.5, Dh3, and Jh2:

```
                                               (SEQ ID NO: 56)
Adaptive agagattcttccagcagcagcgtgactctgagtggacagaatatgcagagtg
         |||||~||||||||||||||||||||||||||||||||||||||||||~||
                                               (SEQ ID NO: 57)
Naive    agagactcttccagcagcagcgtgactctgagtggacagaatatgcagactg
Adaptive aggacacagctgtgtattattgcgccagagagagcatggagtggcgagcctt
         |||||||||||||||||||||||||||||||xx|||||||||||xx|||||
Naive    aggacacagctgtgtattattgcgccagagagagcatggagtggcgagcctt
Adaptive tgattactggggaaagggaacaatggtcactgtcacatcagctcaaccatct
         |||~|||||||||||||||||||||||||||||||||||||||||||||||
Naive    tgactactggggaaagggaacaatggtcactgtcacatcagctcaaccatct
Adaptive gcgcccagtcagtcttcggtttgtctcagtgca
         |||||||||||||||||||||||||||||||||
Naive    gcgcccagtcagtcttcggtttgtctcagtgca
``` where a total of 3 mutations have been counted.

Capture-Recapture.

The task of estimating total populations given limited sample sizes finds its origins in ecology. In a closed ecosystem, each animal "occurs" only once. Therefore, one can make use of the assumption that capturing M individuals out of a population T, setting them free, and then recapturing m occurs at the same rate at which that original M were captured out of the total T. Formally, $m/M=M/T$, and therefore $T=M^2/m$. The problem becomes more challenging when the abundances themselves have a distribution of which we have only partial knowledge.

In each re-sampling of a fish's antibody repertoire, we are positioned to compare individual subsets of antibodies, and ask how much they overlap. In FIG. 4, we plot several estimates of the total IgM antibody repertoire. In the first case, we plot the total number of unique VDJ combinations we observe (excluding the ambiguous-D case). In the second case, we plot a diversity estimate using the equal-representation assumption above. In the third case, we plot the diversity estimate using the observed distribution of abundances.

This last estimate requires some calculation. Let Prob(i in $S_2$|i in $S_1$) be the probability that we find sequence i in sample $S_2$ given we found that same sequence i in sample $S_1$. This is our definition of a recapture rate, which we write $r_i$. Let Prob($x_i$) be the probability that sequence I (without any prior information) occurs with an abundance proportional to $x_i$. Then, we can write the recapture rate in terms of this distribution of abundances:

$$r_i = Prob(i \in S_2 \mid i \in S_1)$$

$$= \sum_{x_i=x} Prob(i \in S_2 \mid x_i) Prob(x_i \mid i \in S_1)$$

$$= \sum_{x_i=x} Prob(i \in S_2 \mid x_i) \left( \frac{Prob(i \in S_1 \mid x_i) Prob(x_i)}{Prob(i \in S_1)} \right)$$

$$= \frac{\Sigma_{x_i=x} Prob(i \in S_2 \mid x_i) Prob(i \in S_1 \mid x_i) Prob(x_i)}{\Sigma_{x_i=x} Prob(i \in S_1 \mid x_i) Prob(x_i)}$$

Let M, as before, be the size of a single sample. Since the probabilities Prob(i in $S_2$|$x_i$) and Prob(i in $S_1$|$x_i$) are themselves functions of both the distribution of abundances and the total diversity of sequences, T:

$$r_i = \frac{\Sigma_{x_i=x}(1-(1-x(T\Sigma_j x_j Prob(x_j))^{-1})^M)^2 Prob(x)}{\Sigma_{x_i=x}(1-(1-x(T\Sigma_j x_j Prob(x_j))^{-1})^M) Prob(x)}$$

where the quantity $T\Sigma_j x_j Prob(x_j)$ is proportional to the total number of reads in the pool from which the samples are being taken. Therefore, the recapture rate $r_i$ and the distribution over abundances Prob($x_i$) can be used to uniquely determine the total diversity, T.

Convergence of Mutated Sequences in Different Fish.

Here we construct a simple null hypothesis allowing us to quantify the amount of antibody sequence convergence among our population of fish. Consider a particular naive sequence A shared by fish i and fish j. Looking at the repertoire of mutated sequences derived from this common ancestral sequence, there is a probability $$p(r) = \left(3^r \binom{m}{r}\right)^{-1}$$

that given m mutable base-pairs of which r are mutated on both, a unique sequence drawn randomly from both fish having A as a common ancestor will be identical.

Threshold analysis in FIG. 6 illustrates that of clusters of size greater than two reads, on average 10% are incorrect. We will conservatively place this at its upper bound of 20%. This allows us to make a simple estimate of the fraction of clusters originating in a given naïve sequence we expect to be truly mutated. Let the observed fraction of unmutated sequences be $g_0$. We then expect the fraction of truly mutated sequences, $f \geq 1$, to be $$f_{\geq 1} \approx (1-g_0)-g_0(20/80)=1-5g_0/4$$

which is made zero should it wind up being negative.

There is an additional technical caveat to making hypermutation estimates due both to genomic differences between the zebrafish in this study and the zebrafish reference genome, and the phenomenon of allelic exclusion, whereby the chromosome expressing the antibody heavy chain is determined independently during the development of each progenitor B-cell. This introduces up to two polymorphisms per V/D/J combination per fish.

In order to compensate for the potential overestimate in somatic mutation we developed a way to conservatively estimate of the number of mutated antibodies with minimal knowledge of fish genotypes. We did this by applying two "genomic baselines", one for each chromosome, to find the minimum possible number of differences between the sequence and the reference genome that could be due to somatic mutation.

For every V/J combination, the minimum detected somatic mutations was set as the first genomic baseline, a. The V/J combination's second genomic baseline, b, was then set to the number of polymorphic differences that would minimize the estimate 1 above (it can be shown easily that this is equal to the most frequent number of f≥ mutations greater than a). The number of sequences with mutations was then set to the total number of sequences with mutation count equal to neither a nor b. The fraction $g_0$, meanwhile, included all sequences with mutation count equal to either a or b.

Figure 11:
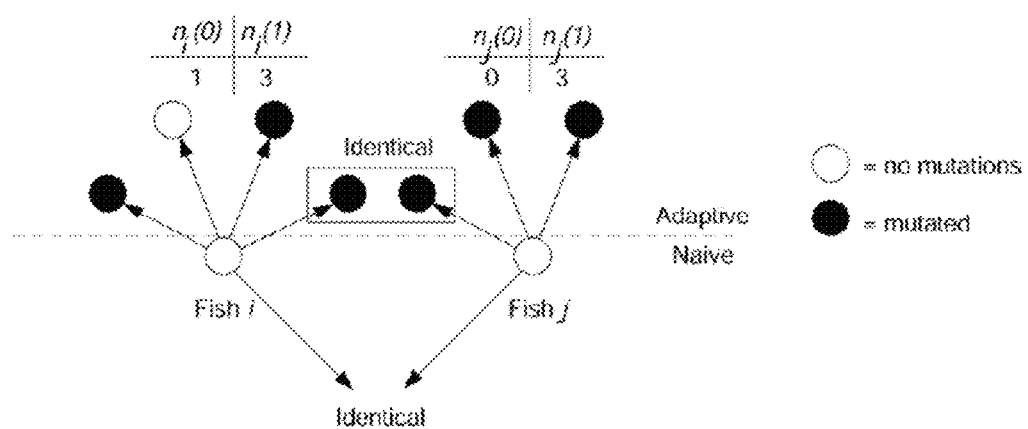
FIG. 11: An example where two lineages are compared to reveal convergence in mutated sequences. Here, (1)(1)/3 3 3/(3 100) 0.033 i j λ=n×n m=xx=and therefore, by the null hypothesis, an identically mutated sequence is considered highly improbable by random chance.

FIG. 11 illustrates the process by which instances of identically mutated sequences may be evaluated in relation to the null hypothesis wherein all convergence is due to random chance. Pairs of mutated sequences from different fish with the same naive sequence are compared to one another. If we conservatively assume that the dominating effect for convergence in mutated sequences from the same naive ancestor is among those with at most one mutation, then on average the $n_i \times n_j$ mutated pairs of sequences from fish i and j will give us approximately $$\lambda = \langle n_i n_j \rangle / 3m = \langle n_i \rangle \langle n_j \rangle + cov(n_i, n_j))/3\text{in}$$

unique convergent events (if we assume the number of unique mutated sequences on the two fish are independent variables, the covariance goes to zero).

If we view the generation of instances of convergence as a Poisson process, this gives us a straightforward way to generate p-values, shown in Table 6. Here we take m=100 (which is also conservative, in order to avoid counting the junctional region, where differences from genomic sequence are not counted as somatic mutations).

Taken together, we observe 55 instances of convergent mutated sequences, compared to ~8 that would be expected from this model, making the null hypothesis for convergence by random drift completely inadequate to explain the results.

B Cell Counts in Zebrafish.

Although B-cell counts in zebrafish have not been performed directly, in large part due to the difficulty developing seralogical probes for labeling, one can make an estimate based on the existence of lymphocyte counts (of both B-cells and T-cells) and T-cells alone. Zebrafish splenic cell counts range from $4.5 \times 10^4$ to $8 \times 10^4$ and given that T cells comprise approximately 3% (Langenau, Traver et al. 2003) of splenocytes, and lymphocytes comprise 11%, one would predict that B cells comprise approximately 8% of splenocytes, or between 3600 and 6400. Meanwhile, T cells comprise approximately 0.07% of blood cells, lymphocytes comprise 1% and erythrocytes comprise 98%. Since zebrafish have 10 μl of blood and $3 \times 10^6$ erythrocytes per microliter the total blood-borne B cell count should be approximately 0.93% of $3 \times 10^7$, or $3 \times 10^5$. This puts an order of magnitude upper limit on the total possible antibody diversity in a given individual at any point in time.

Example 2

Immunization of Zebrafish

In another study using this method, we investigated a simple model of infectious disease by immunizing zebrafish with hapten-conjugated proteins. Antigen-immersion experiments were performed on nine month-old zebrafish over a three-week period. Immersion solutions were prepared using either TNP(11)-BSA (T-5050, Biosearch Technologies), DNP(12)-BSA (D-5050, Biosearch Technologies), and ABA(10)-BSA (A-1200, Biosearch Technologies) dissolved at a total of 210 ug/ml in zebrafish system water. Controls were also set aside without antigen. LPS (lipopolysaccharide, Sigma-Aldrich L2143) was also added to antigen immersion solutions to a total concentration of 70 ug/ml. Zebrafish were first immersed in 4.5% NaCl in system water (see Huising et al. Increased efficacy of immersion vaccination in fish with hyperosmotic pretreatment. Vaccine. 2003 Oct. 1; 21(27-30):4178-93) for 2 minutes, and then placed in antigen/LPS solution for 30 minutes, before being returned to their tanks. This procedure was performed three times over one-week intervals. Fish were terminated one week after final exposure.

Figure 13:
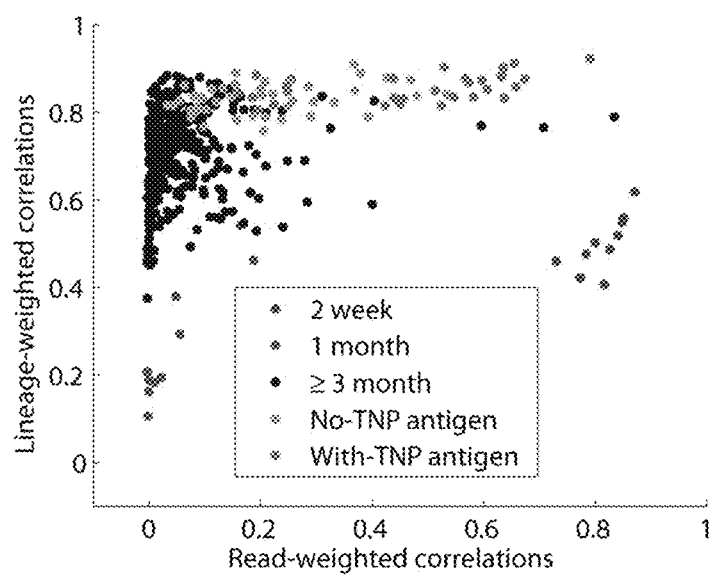
FIG. 13. Signature of a VDJ-specific antigen response. Read-weighted VDJ-vectors are correlated with lineage-weighted VDJ vectors from control sets of zebrafish. Strong age- and stimulation-dependence is observed among these subsets.
Figure 14:
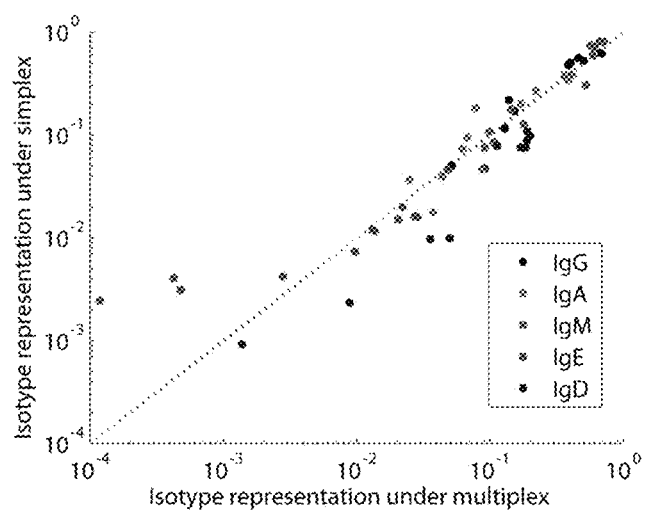
FIG. 14. Correlation of antibody isotype representation between multiplexed and simplexed PCR.

RNA was extracted and purified as described previously. cDNA was amplified and underwent 454 sequencing. VDJ profiles were taken from the IgM heavy chain sequences from each fish and fish repertoires were compared within control groups. While correlating lineage diversity-weighted VDJ repertoires produced similar values to what was observed in other zebrafish of the same age-group (see FIG. 13), TNP-stimulated individuals exhibited especially high read-weighted VDJ correlations. These data on VDJ abundance-stereotypy demonstrate diagnosis of an immune stimulus with the methods of the invention.

Example 3

Sequencing Human Antibody Repertoire

We applied the methods of the invention to study the human antibody repertoire in response to influenza vaccination. The first test consisted of B cell samples from subjects that were immunized with either the trivalent inactivated influenza vaccine (TIV) or the live attenuated influenza vaccine (LAIV). Both naïve and plasmablast B cells were sorted from each individual using Fluorescence Activated Cell Sorting (FACS). Naïve cells were sorted based on the surface expression of CD3− CD19+ CD27− CD38−, plasmablasts were sorted based on the surface expression of CD3− CD19+ CD27+ CD38+. The number of cells collected varied from a few thousand to hundreds of thousands. Samples went through RNA purification and cDNAs were synthesized using the reverse transcription primers listed in the table. Two amplification strategies were used to do the PCR, multiplexed and simplexed. In the multiplexed PCR, all 11 forward primers were mixed in the same tube at an equal ratio, along with reverse primers. For the simplexed PCR, cDNA was aliquoted into 11 different tubes with one forward primer, and all reverse primers, in each tube. For each B cell population from each subject, 11 simplexed PCR products were pooled before the 454 library preparation process.

In one 454 run, we sequenced 24 libraries that had been generated from these 6 subjects (2 different cell types from each subject, 2 ways of amplification for each cell type). For most of the antibody isotypes, good correlations existed between multiplexed and simplexed PCR, except for IgE from three samples. These three IgE samples were from plasmablast populations of three subjects. Since the difference appears to stem from different V-primer biases in multiplexed and simplexed PCR, these differences suggest IgE may have a different V gene segment usage from other isotypes. This might be explained by clonal expansion of a small number allergen-specific B cells in these subjects.

We also compared antibody isotype expression in two cell populations for all subjects. It is known that naïve B cells co-express IgM and IgD with IgM dominating the expression. Upon activation, naïve B cell transforms into plasmablast and switch IgM to IgG while down-regulating IgD expression. Using sequencing, we saw the trend of IgM dominating the naïve B cell population with minor IgD expression. However, in plasmablasts, the majority of the reads belong to IgG, except in donor 2 from the 18-30 year-old group. We also noticed surprisingly high amount of IgA expressing B cells (normally localized in mucous membrane) in the plasmablast population.

Reverse Transcription Primers.

Human reverse transcription primers were designed to cover all known antibody heavy chain isotypes, IgA, IgD, IgE, IgG and IgM, where each isotype is covered by one gene specific primer that anneals to the sequence between 35 to 110 bp into constant domain 1 of the heavy chain.

PCR Primers.

V gene leader region sequences were chosen to maximize the full length of the V gene segments when designing the forward PCR primers. Consensus regions were chosen to minimize the number of forward PCR primer while maximizing the coverage for each primer. Forward PCR primers were designed to cover all possible V gene segments listed in IMGT database. Current primer set covers 207 out of 244 (85%) functional V gene segments including polymorphisms. This number increased to 225 (92%) if one allows one mismatch between primers and target sequences.

Reverse PCR primers were designed to cover all known antibody heavy chain isotypes, IgA, IgD, IgE, IgG and IgM. Each isotype is covered by one gene specific primer that anneals upstream of where reverse transcription primer anneals.

PCR products were cleaned and ligated 454 shotgun genomic sequencing adaptor and the rest of the process for Roche 454 shotgun genomic library construction (Roche 454 protocol). The sequencing primer is embedded in the adaptor. Libraries were then quantified and sequenced following Roche 454 shotgun genomic library sequencing protocol.

TABLE 7

Primers for reverse transcription of human antibody sequence

| | | |
|---|---|---|
| hIgh071609CIgG-RT | SEQ ID NO: 58 | GGGAAGTAGTCCTTGACCAG |
| hIgh071609CIgA-RT | SEQ ID NO: 59 | GGGGAAGAAGCCCTGGAC |
| hIgh071609CIgM-RT | SEQ ID NO: 60 | GGCCACGCTGCTCGTATC |

TABLE 7-continued

Primers for reverse transcription of human antibody sequence

| | | |
|---|---|---|
| hIgh071609CIgE-RT | SEQ ID NO: 61 | AGGGAATGTTTTTGCAGCAG |
| hIgh071609CIgD-RT | SEQ ID NO: 62 | CCACAGGGCTGTTATCCTTT |

TABLE 8

Forward primers in PCR for human immunoglobulins:

| | | |
|---|---|---|
| hIgh062309LR1 | SEQ ID NO: 63 | cgcagaccctctcactcac |
| hIgh062309LR2 | SEQ ID NO: 64 | tggagctgaggtgaagaagc |
| hIgh062309LR3 | SEQ ID NO: 65 | tgcaatctgggtctgagttg |
| hIgh062309LR4 | SEQ ID NO: 66 | ggctcaggactggtgaagc |
| hIgh062309LR5 | SEQ ID NO: 67 | tggagcagaggtgaaaaagc |
| hIgh062309LR6 | SEQ ID NO: 68 | ggtgcagctgttggagtct |
| hIgh062309LR7 | SEQ ID NO: 69 | actgttgaagccttcggaga |
| hIgh062309LR8 | SEQ ID NO: 70 | aaacccacacagaccctcac |
| hIgh062309LR9 | SEQ ID NO: 71 | agtctggggctgaggtgaag |
| hIgh062309LR10 | SEQ ID NO: 72 | ggcccaggactggtgaag |
| hIgh062309LR11 | SEQ ID NO: 73 | ggtgcagctggtggagtc |

TABLE 9

Reverse primers in PCR for human immunoglobulins:

| | | |
|---|---|---|
| hIgh071609CIgG-PCR | SEQ ID NO: 74 | AAGACCGATGGGCCCTTG |
| hIgh071609CIgA-PCR | SEQ ID NO: 75 | GAAGACCTTGGGGCTGGT |
| hIgh071609CIgM-PCR | SEQ ID NO: 76 | GGGAATTCTCACAGGAGACG |
| hIgh071609CIgE-PCR | SEQ ID NO: 77 | GAAGACGGATGGGCTCTGT |
| hIgh071609CIgD-PCR | SEQ ID NO: 78 | GGGTGTCTGCACCCTGATA |

Example 4

Human T Cell Receptor

T cell receptor is composed of two chains, either α and β or γ and δ chains. Hence, T cells can be categorized into αβ and γδ T cells. All four chains have their own V gene segments and constant genes. The primer set designed here is intended to cover only α and β chains.

Human TCR Reverse Transcription Primers.

The human TCR reverse transcription primers were designed to cover α and β chains. Each chain is covered by one gene specific primer that anneals to the sequence between 400 to 460 bp into constant domain. The long cDNA gives flexibility in the PCR step to tailor the amplicon length according to different sequencing platforms. For example, 400 to 600 bp is preferred for Roche 454 and 200 to 300 bp is preferred for Illumina.

Human TCR PCR Primers.

Consensus region of about 60 bp toward the 3' of the V gene segments were chosen to design the PCR forward primers. This is constrained by the current read length of Illumina genome sequencer (100 bp). Because TCR does not have somatic hypermutation, therefore the only information that is needed to estimate the diversity is in the VD and DJ junctional region. PCR primers designed here will allow V gene segments identification as well as D and J gene segments to be identified in one Illumina sequencing read. Consensus region were chosen to minimize the number of forward PCR primer while maximize the coverage for each primer. Forward PCR primers were designed to cover all possible V gene segments listed in IMGT database.

For α chain, current primer set covers 94 out of 104 (90%) functional V gene segments as well as α chain V gene segments that have an open reading frame (ORF) with perfect match. Genes with polymorphisms are also included. This number increased to 97 (93%) if one allows one mismatch between primers and target sequences. Part of the 7% uncovered gene segments are due to the fact that the genomic sequences are not documented to their full length.

For β chain, current primer set covers 118 out of 136 (87%) functional V gene segments as well as α chain V gene segments that have an open reading frame (ORF) with perfect match. Genes with polymorphisms are also included. This number increased to 133 (98%) if one allows one mismatch between primers and target sequences. The three uncovered gene segments are due to the fact that those genomic sequences are not documented to their full length.

Reverse PCR primers were designed to cover both α and β chains, one primer for one chain. For Illumina genome sequencer, the gene specific primers anneal to regions that is 120 to 200 bp into constant gene. For Roche 454, the gene specific primers anneal to regions that is 360 to 420 bp into constant gene.

Sequencing Primers.

PCR products will be cleaned and ligated to either Illumina or 454 sequencing adaptor and the rest of the process for either Illumina or Roche 454 library construction (Illumina or Roche 454 protocol). The sequencing primer is embedded in the adaptor. Libraries were then quantified and sequenced following Illumina or Roche 454 sequencing protocol.

To obtain the sequence information, the cells present in the sample are lysed and nucleic acids of interest (e.g., genomic DNA, RNA, etc.) are collected. Where RNA is being analyzed, it will generally be converted to cDNA by reverse transcriptase. Primers for cDNA synthesis, as described above, may be selective for the immune receptor of interest. For example, where the immune receptor is Ig, primer sets of interest may comprise (see human antibody file). Where the immune receptor is the TCR, the primer set may comprise (see separate file for human TCR)

The immune receptor sequences are then amplified with a set of primers selective for the immune receptor of interest. Separate reactions can be performed for α and β chains, or they can be combined in a single tube. Alternatively, each individual cell is used as a PCR reactor, and the α and β chain are ligated within each cell using complementary sequences between α and β chain primers. Then PCR products generated within each cell are pooled and sequenced.)

TABLE 10

PCR forward PCR primer for a chain

| name | | sequences 5' to 3' |
|---|---|---|
| HuVa4-1 | SEQ ID NO: 79 | TTCACAACTGGGGGACTCA |
| HuVa4-2 | SEQ ID NO: 80 | CTCACAGCTGGGGGACACT |
| HuVa4-3 | SEQ ID NO: 81 | ACTCACAGCTGGGGGATG |
| HuVa4-4 | SEQ ID NO: 82 | GCCTCACAAGTCGTGGACTC |
| HuVa4-5 | SEQ ID NO: 83 | CAGCCTGCAGACTCAGCTAC |
| HuVa4-6 | SEQ ID NO: 84 | GGCAGCAGACACTGCTTCTT |
| HuVa4-7 | SEQ ID NO: 85 | GACCACAGACTCAGGCGTTT |
| HuVa4-8 | SEQ ID NO: 86 | GCTCAGTGATTCAGCCACCT |
| HuVa4-9 | SEQ ID NO: 87 | CCCAGTGATTCAGCCACCTA |
| HuVa4-10 | SEQ ID NO: 88 | CTCAGCGATTCAGCCTCCTA |
| HuVa4-11 | SEQ ID NO: 89 | TCCCAGCTCAGTTACTCAGGA |
| HuVa4-12 | SEQ ID NO: 90 | CAGCCATGCAGGCATCTA |
| HuVa4-13 | SEQ ID NO: 91 | GCCCAGCCTGGTGATACAG |
| HuVa4-14 | SEQ ID NO: 92 | CCATACCTAGTGATGTAGGCATCT |
| HuVa4-15 | SEQ ID NO: 93 | ACATCACAGCCACCCAGAC |
| HuVa4-16 | SEQ ID NO: 94 | CAACCTGAAGACTCGGCTGT |
| HuVa4-17 | SEQ ID NO: 95 | TTGCAGCTACTCAACCTGGA |
| HuVa4-18 | SEQ ID NO: 96 | CCAGACTGGGGACTCAGCTA |
| HuVa4-19 | SEQ ID NO: 97 | CCCAGCCTGGAGACTCTG |
| HuVa4-20 | SEQ ID NO: 98 | CCAGCCTGGAGACTCAGC |
| HuVa4-21 | SEQ ID NO: 99 | AGCCTCCCATCCCAGAGAC |
| HuVa4-22 | SEQ ID NO: 100 | CTGCCGTGCATGACCTCT |
| HuVa4-23 | SEQ ID NO: 101 | CAAAGGATCCCAGCCTGAA |
| HuVa4-24 | SEQ ID NO: 102 | CACAGCCCCTAAACCTGAAG |
| HuVa4-25 | SEQ ID NO: 103 | CCGTGCAGCCTGAAGATT |
| HuVa4-26 | SEQ ID NO: 104 | GCTTCTCAGCCTGGTGACTC |
| HuVa4-27 | SEQ ID NO: 105 | GCTCCAGATGAAAGACTCTGC |
| HuVa4-28 | SEQ ID NO: 106 | CTGCCCTTGTGAGCGACT |
| HuVa4-29 | SEQ ID NO: 107 | AGCGACGCGGCTGAGTA |
| HuVa4-30 | SEQ ID NO: 108 | ACCGACCCGGCTGAGTA |
| HuVa4-31 | SEQ ID NO: 109 | TCTGTGCATTGGAGTGATGC |
| HuVa4-32 | SEQ ID NO: 110 | GTGCAGTGGAGTGACACAGC |

TABLE 10-continued

PCR forward PCR primer for α chain

| name | | sequences 5' to 3' |
|---|---|---|
| HuVa4-33 | SEQ ID NO: 111 | TCAGTTCAAGTGTCAGACTCAGC |
| HuVa4-34 | SEQ ID NO: 112 | GAAAGACTCAGTTCAAGAGTCAGA |
| HuVa4-35 | SEQ ID NO: 113 | CAGTCCAGGTATCAGACTCAGC |
| HuVa4-36 | SEQ ID NO: 114 | GGTGCAGCTGTCGGACTC |
| HuVa4-37 | SEQ ID NO: 115 | TGCTCAAGAGGAAGACTCAGC |
| HuVa4-38 | SEQ ID NO: 116 | GGAGGCAGATGCTGCTGT |
| HuVa4-39 | SEQ ID NO: 117 | CCACGCTACGCTGAGAGAC |
| HuVa4-40 | SEQ ID NO: 118 | CGTGCTACCTTGAGAGATGCT |
| HuVa4-41 | SEQ ID NO: 119 | TCCCTGAGCGACACTGCT |
| HuVa4-42 | SEQ ID NO: 120 | caacccatgtgagtgatgct |

TABLE 11

Primers in the reverse transcription for α chain

| name | | sequences 5' to 3' |
|---|---|---|
| HuCa3'RT-4 | SEQ ID NO: 121 | cagatctcagctggaccaca |

TABLE 12

PCR reverse primers for α chain

| Sequencer | name | | sequences 5' to 3' |
|---|---|---|---|
| Illumina | HuCa3'illumina-4 | SEQ ID NO: 122 | GCACTGTTGCTCTTGAAGTCC |
| 454 | HuCa3'454-4 | SEQ ID NO: 123 | gattaaacccggccactttc |

TABLE 13

PCR forward PCR primer for β chain

| name | | sequences 5' to 3' |
|---|---|---|
| HuVb4-1 | SEQ ID NO: 124 | GGGGACTCGGCCATGTAT |
| HuVb4-2 | SEQ ID NO: 125 | GGGGGACTCAGCCGTGTAT |
| HuVb4-3 | SEQ ID NO: 126 | GGGGGACACAGCCATGTA |
| HuVb4-4 | SEQ ID NO: 127 | GAGGACTCCGCCGTGTATC |

TABLE 13-continued

PCR forward PCR primer for β chain

| name | | sequences 5' to 3' |
|---|---|---|
| HuVb4-5 | SEQ ID NO: 128 | GCGGGACTCAGCCATGTAT |
| HuVb4-6 | SEQ ID NO: 129 | GGACTCGGCCGTGTATCT |
| HuVb4-7 | SEQ ID NO: 130 | AGAACCCAGGGACTCAGC |
| HuVb4-8 | SEQ ID NO: 131 | CTGGAGGACTCAGCCATGT |
| HuVb4-9 | SEQ ID NO: 132 | CTGGAGGATTCTGGAGTTTATTTC |
| HuVb4-10 | SEQ ID NO: 133 | AGGAGATTCGGCAGCTTATTT |
| HuVb4-11 | SEQ ID NO: 134 | GCTTGAGGATTCAGCAGTGT |
| HuVb4-12 | SEQ ID NO: 135 | TTGGTGACTCTGCTGTGTATTTC |
| HuVb4-13 | SEQ ID NO: 136 | AGAAGACTCGGCCCTGTATC |
| HuVb4-14 | SEQ ID NO: 137 | GGGGACTCAGCCCTGTACT |
| HuVb4-15 | SEQ ID NO: 138 | GGGGGACTCAGCTTTGTATTT |
| HuVb4-16 | SEQ ID NO: 139 | GGGGACTCGGCCCTTT |
| HuVb4-17 | SEQ ID NO: 140 | GACGACTCGGCCCTGTATC |
| HuVb4-18 | SEQ ID NO: 141 | GGACTCGGCCCTGTATCTC |
| HuVb4-19 | SEQ ID NO: 142 | TCAGTGACTCTGGCTTCTATCTC |
| HuVb4-20 | SEQ ID NO: 143 | CCTCCTCCCAGACATCTGTA |
| HuVb4-21 | SEQ ID NO: 144 | CGCTCCCAGACATCTGTGTAT |
| HuVb4-22 | SEQ ID NO: 145 | GCTACCAGCTCCCAGACATC |
| HuVb4-23 | SEQ ID NO: 146 | CCCTCTCAGACATCTGTGTACTT |
| HuVb4-24 | SEQ ID NO: 147 | CCCTCCCAAACATCTGTGTA |
| HuVb4-25 | SEQ ID NO: 148 | CCTCCCAGACATCTGTGTACTT |
| HuVb4-26 | SEQ ID NO: 149 | CCCTCCCAGACATCTGTATACTT |
| HuVb4-27 | SEQ ID NO: 150 | CCCAACCAGACCTCTCTGT |
| HuVb4-28 | SEQ ID NO: 151 | CCAACCAGACATCTATGTACCTCT |
| HuVb4-29 | SEQ ID NO: 152 | CCCTCACATACCTCTCAGTACC |

TABLE 13-continued

PCR forward PCR primer for β chain

| name | | sequences 5' to 3' |
|---|---|---|
| HuVb4-30 | SEQ ID NO: 153 | CCCAACCAGACAGCTCTTTAC |
| HuVb3-31 | SEQ ID NO: 154 | GAACCCGACAGCTTTCTATCTC |
| HuVb4-32 | SEQ ID NO: 155 | TGCCCATCCTGAAGACAGC |
| HuVb4-33 | SEQ ID NO: 156 | CATGAGCCCTGAAGACAGC |
| HuVb4-34 | SEQ ID NO: 157 | CTCGGAACCGGGAGACAC |
| HuVb4-35 | SEQ ID NO: 158 | CAGAGCCGAGGGACTCAG |
| HuVb4-36 | SEQ ID NO: 159 | GGGGGACTTGGCTGTGTAT |
| HuVb4-37 | SEQ ID NO: 160 | CCAGACAGCTTCTAGGTTACTTCAG |
| HuVb4-38 | SEQ ID NO: 161 | GCTCCCTCTCAGACTTCTGTTT |
| HuVb4-39 | SEQ ID NO: 162 | CAGGAGACCTGAAGACAGCA |

TABLE 14

Primers in the reverse transcription for β chain

| name | | sequences 5' to 3' |
|---|---|---|
| HuCb3'RT-4 | SEQ ID NO: 163 | tcatagaggatggtggcaga |

TABLE 15

PCR reverse primers for β chain

| Sequencer | name | | sequences 5' to 3' |
|---|---|---|---|
| Illumina | HuCb3'illumina-4 | SEQ ID NO: 164 | cacctccttcccattc acc |
| 454 | HuCb3'454-4 | SEQ ID NO: 165 | agccacagtctgctct accc |

Example 5

Antigenic Stimulation in Zebrafish

Zebrafish were challenged with immersion vaccination using different combinations of antigens. Methods of the invention were used to analyze the effects of external stimulation on the immune repertoire.

Antigen-immersion experiments were performed on nine month-old WIK zebrafish over a three-week period. Immersion solutions were prepared using either TNP(11)-BSA (T-5050, Biosearch Technologies), DNP(12)-BSA (D-5050, Biosearch Technologies), and ABA(10)-BSA (A-1200, Biosearch Technologies) dissolved at a total of 210 ug/ml in zebrafish system water. Controls were also set aside without antigen. Lipopolysaccharide (Sigma-Aldrich L2143) was also added to antigen immersion solutions to a total concentration of 70 ug/ml. Zebrafish were first immersed in 4.5% NaCl in system water (Huising et al, 2003) for 2 minutes, and then placed in antigen/LPS solution for 30 minutes, before being returned to their tanks. This procedure was performed three times over one-week intervals. Fish were terminated one week after final exposure. The experiment is diagrammed in FIG. 16.

Fish were euthanized and snap frozen in liquid nitrogen and stored in −80 degrees C. RNA was extracted and purified and cDNA was amplified as described in Weinstein et al, May 8, 2009: 807-810, incorporated by reference herein. Standard Roche 454 GS Titanium shotgun library protocol was followed. Multiplex Identifier (MID)—containing oligonucleotides were synthesized by Integrated DNA Technologies, Inc. (Coralville, Iowa) and were annealed to form 454 adaptor according to Roche's protocol.

Figure 17A:
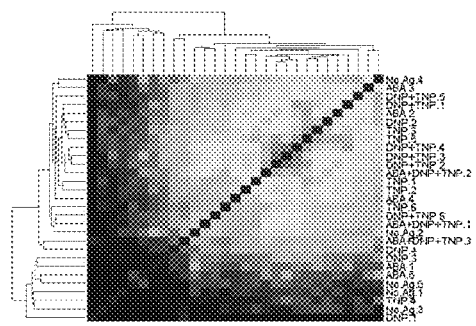
FIG. 17A-17D.

Lineage-analysis was performed as described above, with each individual subsampled (without replacement) to 40,000 reads. Sequences were filtered on having indels outside of their junctional regions as well as lacking any indels relative to the most abundant sequence in their respective lineage. VDJ correlations were initially performed on read-weighted repertoires, as described in Weinstein et al. 2009 and Jiang et al. 2011. By performing hierarchical clustering with the Euclidean distances measured between correlation vectors, the data was observed to partition into groups correlating well and others not correlating well (FIG. 17A). 4 out of the 5 no-antigen samples were found to cluster among the poorly correlated samples, whereas antigen-stimulated samples were found to cluster among the better-correlated samples.

Figure 17B:
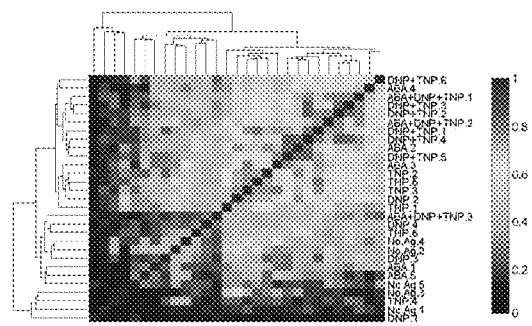
Figure 17C:
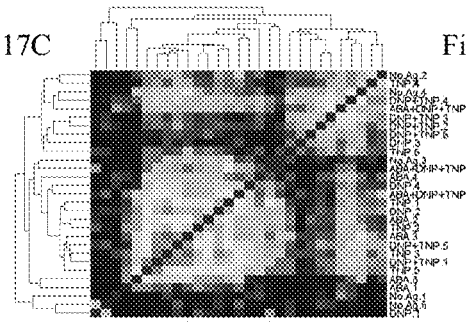
Figure 17D:
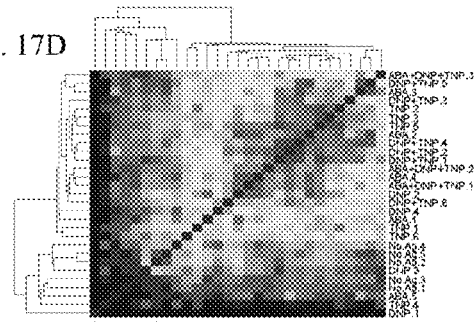

To better probe this partition and to reduce the noise in the analysis, only those sequences existing in lineages of diversity 5 or greater were considered. A similar examination on the hierarchically-clustered VJ-correlation matrix of this data showed a far better partition, with no-antigen samples clustering entirely among the poorly-correlated group (FIG. 17B). Furthermore, the specificity of the immune response to specific antigens began emerging, as zebrafish stimulated with single antigens clustered together (eg TNP-alone), and those stimulated with double antigens clustered together (DNP-TNP).

In order to probe the way in which sequence characteristics like somatic mutations played a role in the partition of groups of antigen-stimulated individuals, we sorted the sequences analyzed in FIG. 17 by the number of mutations found outside of their VDJ junctions. By dividing equal numbers of reads in each sample into "sub-repertoires" containing more than or less than the median number of mutations, each repertoire was effectively decomposed into lower- and higher-mutated halves. Low-mutation VJ correlations (FIG. 17C) showed a breakdown in the partition observed in FIGS. 17A and 17B. Meanwhile, the VJ correlations of the highly-mutated half (FIG. 17D) retained a very strong partition, with all 5 no-antigen samples clustering tightly into the uncorrelated group of individuals, and antigen-stimulated individuals clustering almost entirely outside of this region.

The data demonstrate the ability for VDJ and VJ correlations to provide information about the stimuli experienced by the immune system. By using measurements of known biological significance, such as somatic mutations, to decompose the repertoire into both minimally and maximally informative partitions, we at once validate our measurement as containing biological signal and uncover potentially powerful ways to filter out noise.

Example 6

Human subjects were immunized with seasonal influenza virus vaccine and methods of the invention were used to monitor dynamic changes in the subject's immune repertoire on the day of immunization (visit 1) and 7 days (visit 2) and 28 days (visit 3) subsequent to immunization.

Peripheral blood mononuclear cells were purified from blood drawn on visit 1 and visit 3. Naïve and plasmablast B cells were further sorted for samples acquired from visit 2 using fluorescence activated cell sorting (FACS). Naïve cells were sorted based on the surface expression of CD3− CD19+ CD27− CD38−. Plasmablasts were sorted based on the surface expression of CD3− CD19+ CD27+ CD38+. Samples went through RNA purification, cDNAs were synthesized using the reverse transcription primers listed in the tables of Example 4, and simplex PCR was performed. In this scheme, cDNA was aliquoted into 11 different tubes with one forward primer, and all reverse primers, in each tube. For each B cell population from each subject, 11 simplexed PCR products were pooled before the 454 library preparation process. The PCR condition was optimized to be initial denaturing at 94° C. for 2 min followed by 23 cycles of denaturing at 94° C. for 30 s, annealing at 60° C. for 30 s and extension at 68° C. for 2 min. This was followed by a final extension at 68° C. for 7 min.

Figure 18:
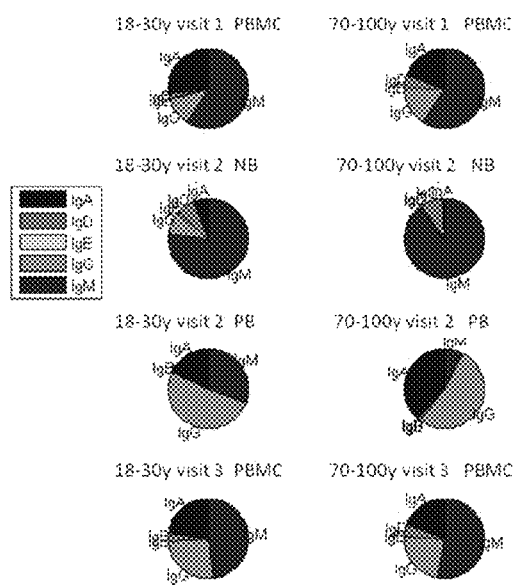
FIG. 18: isotype usage in PBMC, naïve B cells (NB) and plasma blasts (PB) acquired at different time points for two individuals received TIV vaccine.
Figure 19:
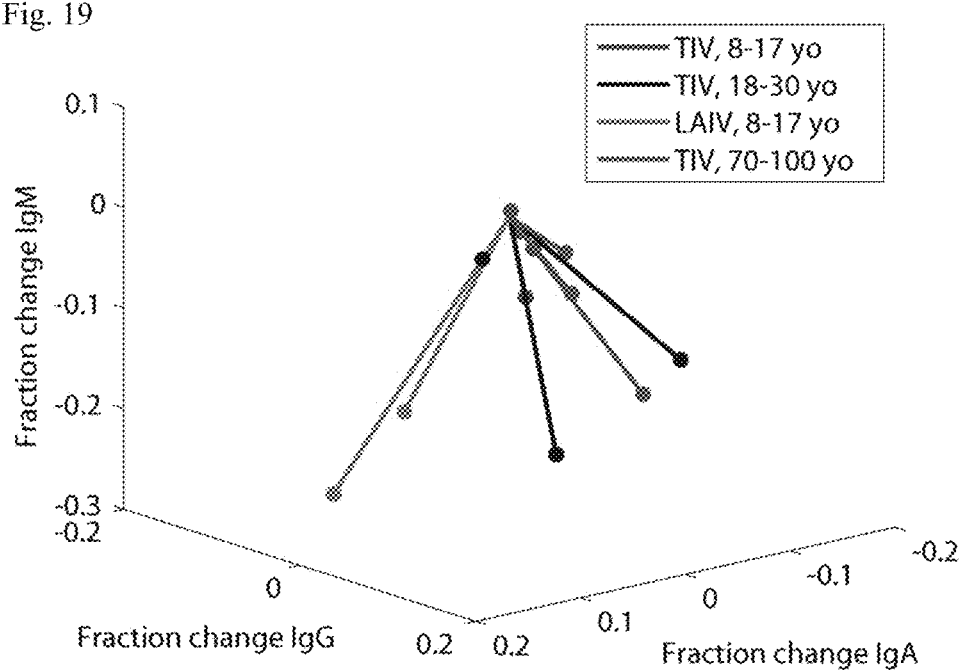
FIG. 19. Fractional composition of each isotype at visit 3 minus fractional composition at visit 1. Color-coded according to vaccine and age-group.

Isotype usage is visualized in the form of a pie chart (FIG. 18). There are isotype switchings for samples acquired at different time points, e.g. an increase of IgG content and decrease of IgM content in visit 3 compared with visit 1. The overall changes of isotype switch for the most important 3 isotypes (IgA, IgG and IgM) in all 12 subjects sequenced are summarized in FIG. 19, wherein the fractional composition of IgA, IgG, and IgM at visit 3 was subtracted from that at visit 1 (making each line into a "trajectory"). Subjects receiving a LAIV nasal flu vaccine showed an increase in IgA fraction. This is consistent with the fact that attenuated live viruses in LAIV vaccine proliferate in the nasal mucosal membrane, possibly causing strong IgA mediated mucosal immunity.

Figure 20:
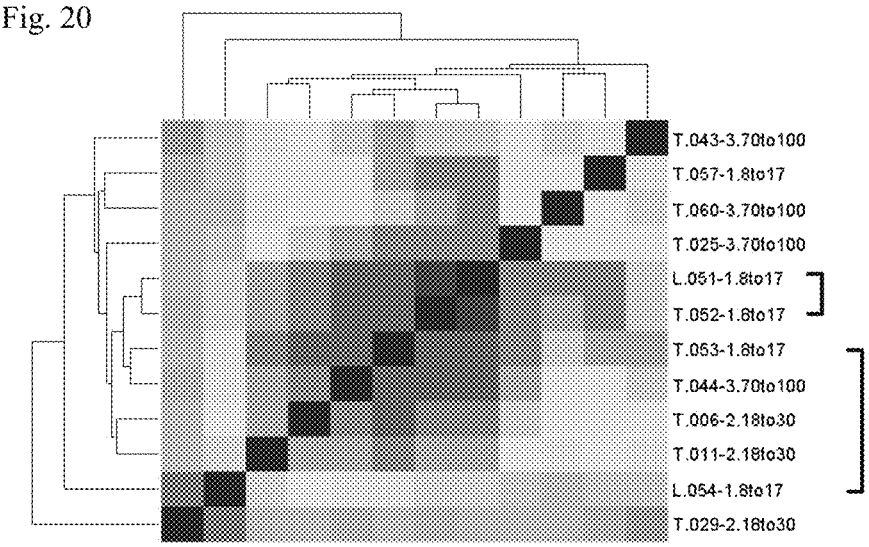
FIG. 20. VDJ correlations using visit 1 (pre-vaccination), with V's, D's, and J's grouped by gene sub-family. Patients to be vaccinated with LAIV are labeled with "L." and those to be vaccinated with TIV are labeled with "T." The final part of the name "XtoY" indicates age-range. Twins are indicated.
Figure 21:
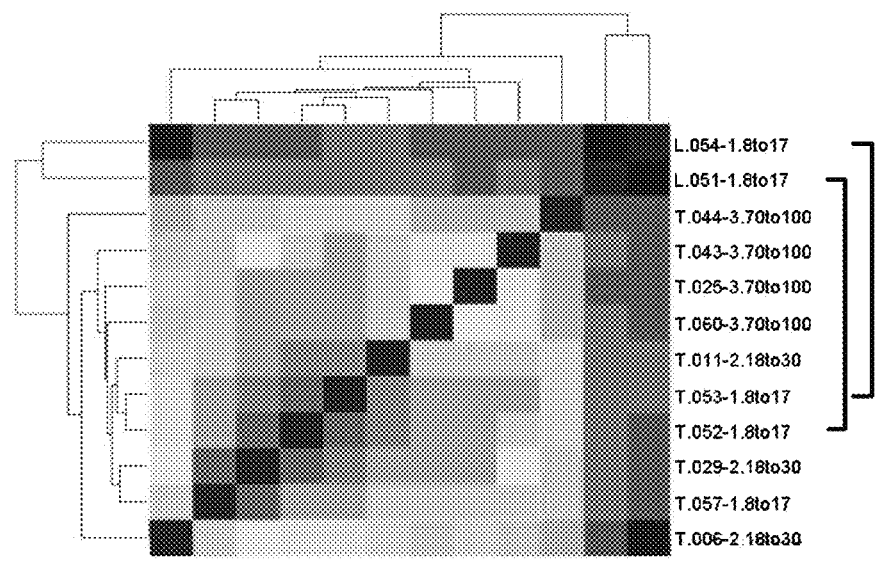
FIG. 21. VDJ correlations from the same individuals as in FIG. 3 at visit 3 (4 weeks post-vaccination), with V's, D's, and J's grouped by gene sub-family. Twins are indicated.
Figure 22:
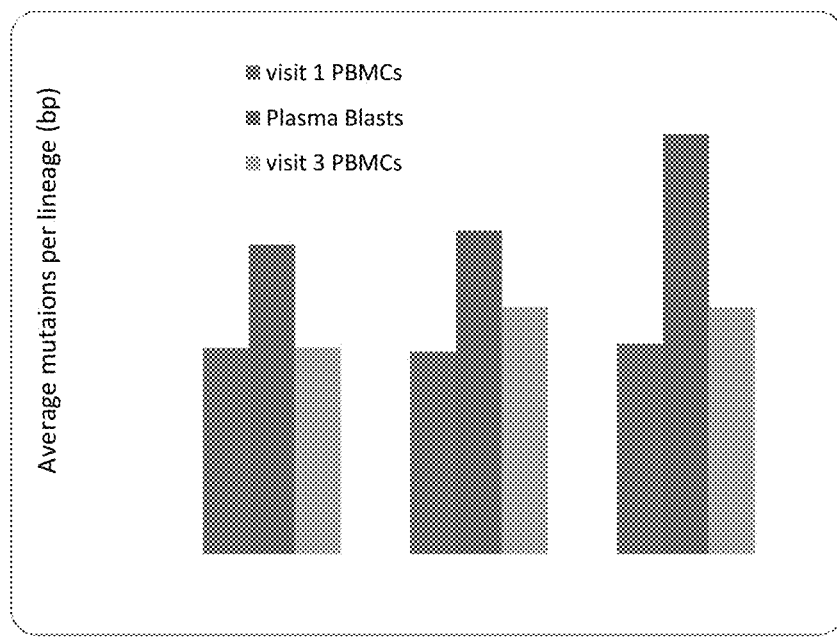
FIG. 22 is a bar graph showing average mutations per lineage.

Twins consistently had higher correlations in VDJ usage in all isotypes (0.54 for IgA, 0.83 for IgD, 0.35 for IgG and 0.97 for IgM) compared with non-twins for visit 1 sample (0.33 for IgA, 0.69 for IgD, 0.27 for IgG and 0.88 for IgM). IgM had the highest correlation in VDJ usage compared with other isotypes. This correlation analysis can also be used in conjunction with hierarchical clustering (using a Euclidean distance metric, as in the zebrafish data) to distinguish similar groups of patient antibody repertoires. For example, FIG. 20 shows that twins have higher VDJ correlations than non-twins for visit 1 samples and they are closer to each other in terms of hierarchical distance than non-twins. However, for visit 3, individuals received the same vaccines are clustered together in the analysis (FIG. 21) indicating that different vaccines may induce a difference signature in terms of VDJ usage. This may serve as a biomarker in disease diagnosis and vaccine efficacy evaluation.

---

What is claimed is:

1. A method of characterizing a set of immunoglobulin receptors, or fragments thereof, from a sample obtained from a subject, comprising a plurality of immunoglobulin heavy chain VDJ exon sequences, the method comprising:

(a) sequencing the VDJ exon sequences to obtain at least $10^4$ sequence reads of immunoglobulin heavy chain sequences, comprising sequences from a plurality of different genomic V segments, a plurality of different genomic D segments, and a plurality of different genomic J segments;

(b) comparing the immunoglobulin heavy chain sequences obtained in step (a) to reference immunoglobulin sequences comprising a plurality of genomic heavy chain V-segment sequences to identify regions of similarity and difference between the immunoglobulin heavy chain sequences obtained in step (a) and the reference immunoglobulin sequences;

(c) grouping identical immunoglobulin heavy chain sequences obtained in Step (a) based on the comparing step (b) to identify a plurality of groups of heavy chain VDJ sequences;

(d) clustering heavy chain VDJ sequences from individual groups from Step (c) to define a plurality of individual clusters;

(e) determining consensus sequences for the individual clusters, wherein the consensus sequences correspond to heavy chain VDJ segments of the subject's immune repertoire, and wherein the consensus sequences have reduced amplification bias and sequencing error compared to the sequence data of Step (a); and (f) identifying somatic mutations in the heavy-chain VDJ exon sequences by comparing consensus sequences to the reference immunoglobulin sequences; thereby characterizing the set of immunoglobulin receptors, or fragments thereof.

2. The method of claim 1, further comprising:
applying a statistical metric that characterizes diversity to the sequencing data from step (a) in order to further characterize the set of immunological receptors or fragments thereof.

3. The method of claim 1, further comprising:
performing a statistical analysis on the sequencing data from step La) to represent sequence variation as a function of sequence frequency.

4. A method of comparing immunoglobulin repertoires of two or more subjects, comprising:
characterizing a first subject's set of immunoglobulin receptors using the method of claim 1;
characterizing a second subject's set of immunoglobulin receptors using the method of claim 1; and
comparing the characterization of the first subject's set of immunoglobulin receptors with the characterization of the second subject's set of immunoglobulin receptors.

5. The method of claim 2, wherein the statistical metric is an entropy metric, an ecology metric, a variation of abundance metric, a species richness metric, or a species heterogeneity metric.

6. The method of claim 3, wherein the sequence variation is junctional diversity, somatic hypermutation, VDJ/VJ rearrangement, or VDJ/VJ recombination.

7. The method of claim 1, wherein the at least $10^4$ sequence reads comprises at least $10^5$, $10^6$, $10^7$, $10^8$, $10^{10}$, or $10^{12}$ sequence reads.

8. The method of claim 1, wherein the reference immunoglobulin sequences further comprises genomic J-segment sequences, and the sequences obtained in step (a) are compared to the reference immunoglobulin sequences to make V and J-segment assignments.

9. The method of claim 4, wherein the comparing comprises obtaining a statistical metric of correlation between the two subjects' sets of immunoglobulin receptors.

10. The method of claim 1, wherein the comparing comprises obtaining a first statistical metric of correlation between the sequence data obtained in step (a) and the reference immunoglobulin sequences.

11. The method of claim 9, wherein the statistical metric of correlation reflects antibody heavy chain, diversity or abundance.

12. The method of claim 1, further comprising performing a computational rarefaction analysis of the sequence data obtained in step (a) to estimate the completeness of the set of immunoglobulin receptors measurement.

13. The method of claim 1, wherein the nucleic acids encoding the set of immunological receptors are obtained from a subject having or suspected of having an autoimmune disorder, a symptom of allergy, asthma, an infection, or cancer.

* * * * *

SEQUENCE LISTING

<160> NUMBER OF SEQ ID NOS: 165

<210> SEQ ID NO 1
<211> LENGTH: 20
<212> TYPE: DNA
<213> ORGANISM: Artificial Sequence
<220> FEATURE:
<223> OTHER INFORMATION: Synthetic primer

<400> SEQUENCE: 1
tggtctcctc tgccttttgt                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
aaccatgatc gcctcatctc                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
gatggcaaca acatcctgtg                                              20

<210> SEQ ID NO 4
<211> LENGTH: 20
<212> TYPE: DNA
<213> ORGANISM: Artificial Sequence

```
<220> FEATURE:
<223> OTHER INFORMATION: Synthetic primer

<400> SEQUENCE: 4
tgcatttcag ttctgctgct                                          20

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
acgaatgcag gagtcagaca                                          20

<210> SEQ ID NO 6
<211> LENGTH: 21
<212> TYPE: DNA
<213> ORGANISM: Artificial Sequence
<220> FEATURE:
<223> OTHER INFORMATION: Synthetic primer

<400> SEQUENCE: 6
tgtttcaact gttcgtggtc a                                        21

<210> SEQ ID NO 7
<211> LENGTH: 22
<212> TYPE: DNA
<213> ORGANISM: Artificial Sequence
<220> FEATURE:
<223> OTHER INFORMATION: Synthetic primer

<400> SEQUENCE: 7
tggagttgtg ttgatgatga tt                                       22

<210> SEQ ID NO 8
<211> LENGTH: 22
<212> TYPE: DNA
<213> ORGANISM: Artificial Sequence
<220> FEATURE:
<223> OTHER INFORMATION: Synthetic primer

<400> SEQUENCE: 8
ttcatatgca catggtcagt ca                                       22

<210> SEQ ID NO 9
<211> LENGTH: 21
<212> TYPE: DNA
<213> ORGANISM: Artificial Sequence
<220> FEATURE:
<223> OTHER INFORMATION: Synthetic primer

<400> SEQUENCE: 9
tgtggtgatt gtctttcaag g                                        21

<210> SEQ ID NO 10
<211> LENGTH: 22
<212> TYPE: DNA
<213> ORGANISM: Artificial Sequence
<220> FEATURE:
<223> OTHER INFORMATION: Synthetic primer

<400> SEQUENCE: 10
tggaaaagga gtcaaaaagc at                                       22
```

```
<210> SEQ ID NO 11
<211> LENGTH: 22
<212> TYPE: DNA
<213> ORGANISM: Artificial Sequence
<220> FEATURE:
<223> OTHER INFORMATION: Synthetic primer

<400> SEQUENCE: 11
gcttttgtca tgtttgctct ca                                    22

<210> SEQ ID NO 12
<211> LENGTH: 22
<212> TYPE: DNA
<213> ORGANISM: Artificial Sequence
<220> FEATURE:
<223> OTHER INFORMATION: Synthetic primer

<400> SEQUENCE: 12
gcttactgct gctctcattc ag                                    22

<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
tttctgctgc tgtgctttac                                       20

<210> SEQ ID NO 14
<211> LENGTH: 21
<212> TYPE: DNA
<213> ORGANISM: Artificial Sequence
<220> FEATURE:
<223> OTHER INFORMATION: Synthetic primer

<400> SEQUENCE: 14
ctgctgtttt cattggcctt a                                     21

<210> SEQ ID NO 15
<211> LENGTH: 22
<212> TYPE: DNA
<213> ORGANISM: Artificial Sequence
<220> FEATURE:
<223> OTHER INFORMATION: Synthetic primer

<400> SEQUENCE: 15
ggtttatact gtcaaggcat gg                                    22

<210> SEQ ID NO 16
<211> LENGTH: 21
<212> TYPE: DNA
<213> ORGANISM: Artificial Sequence
<220> FEATURE:
<223> OTHER INFORMATION: Synthetic primer

<400> SEQUENCE: 16
cagcctcaag atgaagaatg c                                     21

<210> SEQ ID NO 17
<211> LENGTH: 20
<212> TYPE: DNA
<213> ORGANISM: Artificial Sequence
<220> FEATURE:
<223> OTHER INFORMATION: Synthetic primer
```

<400> SEQUENCE: 17
ctagtgctgt ttctggcagt                                          20

<210> SEQ ID NO 18
<211> LENGTH: 22
<212> TYPE: DNA
<213> ORGANISM: Artificial Sequence
<220> FEATURE:
<223> OTHER INFORMATION: Synthetic primer

<400> SEQUENCE: 18
catgatcacc tcatctctct gc                                       22

<210> SEQ ID NO 19
<211> LENGTH: 25
<212> TYPE: DNA
<213> ORGANISM: Artificial Sequence
<220> FEATURE:
<223> OTHER INFORMATION: Synthetic primer

<400> SEQUENCE: 19
catgattctg agcattttat catgt                                    25

<210> SEQ ID NO 20
<211> LENGTH: 23
<212> TYPE: DNA
<213> ORGANISM: Artificial Sequence
<220> FEATURE:
<223> OTHER INFORMATION: Synthetic primer

<400> SEQUENCE: 20
caataatcaa ctcactcctg ctg                                      23

<210> SEQ ID NO 21
<211> LENGTH: 21
<212> TYPE: DNA
<213> ORGANISM: Artificial Sequence
<220> FEATURE:
<223> OTHER INFORMATION: Synthetic primer

<400> SEQUENCE: 21
ctgcgtccag tgtatattcc a                                        21

<210> SEQ ID NO 22
<211> LENGTH: 22
<212> TYPE: DNA
<213> ORGANISM: Artificial Sequence
<220> FEATURE:
<223> OTHER INFORMATION: Synthetic primer

<400> SEQUENCE: 22
tgtattgact gtcaggttgt gc                                       22

<210> SEQ ID NO 23
<211> LENGTH: 18
<212> TYPE: DNA
<213> ORGANISM: Artificial Sequence
<220> FEATURE:
<223> OTHER INFORMATION: Synthetic primer

<400> SEQUENCE: 23
tctttctgca gttggcag                                            18

<210> SEQ ID NO 24
<211> LENGTH: 22
<212> TYPE: DNA
<213> ORGANISM: Artificial Sequence
<220> FEATURE:
<223> OTHER INFORMATION: Synthetic primer

<400> SEQUENCE: 24
tctcaaagtt gttggtgtca ga                                        22

<210> SEQ ID NO 25
<211> LENGTH: 23
<212> TYPE: DNA
<213> ORGANISM: Artificial Sequence
<220> FEATURE:
<223> OTHER INFORMATION: Synthetic primer

<400> SEQUENCE: 25
ctctctaaac aagtgcaaag gtc                                       23

<210> SEQ ID NO 26
<211> LENGTH: 23
<212> TYPE: DNA
<213> ORGANISM: Artificial Sequence
<220> FEATURE:
<223> OTHER INFORMATION: Synthetic primer

<400> SEQUENCE: 26
tggaccttaa acttaactgt ctg                                       23

<210> SEQ ID NO 27
<211> LENGTH: 22
<212> TYPE: DNA
<213> ORGANISM: Artificial Sequence
<220> FEATURE:
<223> OTHER INFORMATION: Synthetic primer

<400> SEQUENCE: 27
ccatatgttt ctggcatctc cc                                        22

<210> SEQ ID NO 28
<211> LENGTH: 20
<212> TYPE: DNA
<213> ORGANISM: Artificial Sequence
<220> FEATURE:
<223> OTHER INFORMATION: Synthetic primer

<400> SEQUENCE: 28
tgcactgaga caaaccgaag                                           20

<210> SEQ ID NO 29
<211> LENGTH: 20
<212> TYPE: DNA
<213> ORGANISM: Artificial Sequence
<220> FEATURE:
<223> OTHER INFORMATION: Synthetic primer

<400> SEQUENCE: 29
tcagaggcca gacatccaat                                           20

<210> SEQ ID NO 30
<211> LENGTH: 20
<212> TYPE: DNA
<213> ORGANISM: Artificial Sequence
<220> FEATURE:
<223> OTHER INFORMATION: Synthetic primer

```
<400> SEQUENCE: 30
tgattgaccc atcagaacca                                              20

<210> SEQ ID NO 31
<211> LENGTH: 20
<212> TYPE: DNA
<213> ORGANISM: Artificial Sequence
<220> FEATURE:
<223> OTHER INFORMATION: Synthetic primer

<400> SEQUENCE: 31
gaatgctggg tgacgttttt                                              20

<210> SEQ ID NO 32
<211> LENGTH: 20
<212> TYPE: DNA
<213> ORGANISM: Artificial Sequence
<220> FEATURE:
<223> OTHER INFORMATION: Synthetic primer

<400> SEQUENCE: 32
gtctggagtc catcccttca                                              20

<210> SEQ ID NO 33
<211> LENGTH: 20
<212> TYPE: DNA
<213> ORGANISM: Artificial Sequence
<220> FEATURE:
<223> OTHER INFORMATION: Synthetic primer

<400> SEQUENCE: 33
attgtcttga ggcctggtca                                              20

<210> SEQ ID NO 34
<211> LENGTH: 20
<212> TYPE: DNA
<213> ORGANISM: Artificial Sequence
<220> FEATURE:
<223> OTHER INFORMATION: Synthetic primer

<400> SEQUENCE: 34
acctgtgcat gcagtggatt                                              20

<210> SEQ ID NO 35
<211> LENGTH: 20
<212> TYPE: DNA
<213> ORGANISM: Artificial Sequence
<220> FEATURE:
<223> OTHER INFORMATION: Synthetic primer

<400> SEQUENCE: 35
ctgtgcctgc agtggattta                                              20

<210> SEQ ID NO 36
<211> LENGTH: 20
<212> TYPE: DNA
<213> ORGANISM: Artificial Sequence
<220> FEATURE:
<223> OTHER INFORMATION: Synthetic primer

<400> SEQUENCE: 36
tcatcaaacc aggcaatgaa                                              20
```

```
<210> SEQ ID NO 37
<211> LENGTH: 20
<212> TYPE: DNA
<213> ORGANISM: Artificial Sequence
<220> FEATURE:
<223> OTHER INFORMATION: Synthetic primer

<400> SEQUENCE: 37
tggagtcgat tgaaagctca                                               20

<210> SEQ ID NO 38
<211> LENGTH: 24
<212> TYPE: DNA
<213> ORGANISM: Artificial Sequence
<220> FEATURE:
<223> OTHER INFORMATION: Synthetic primer

<400> SEQUENCE: 38
cgtcctgatg actctctcac tatc                                          24

<210> SEQ ID NO 39
<211> LENGTH: 22
<212> TYPE: DNA
<213> ORGANISM: Artificial Sequence
<220> FEATURE:
<223> OTHER INFORMATION: Synthetic primer

<400> SEQUENCE: 39
tgtgacaaag agacctggag aa                                            22

<210> SEQ ID NO 40
<211> LENGTH: 20
<212> TYPE: DNA
<213> ORGANISM: Artificial Sequence
<220> FEATURE:
<223> OTHER INFORMATION: Synthetic primer

<400> SEQUENCE: 40
gtttctggac tctcccttgc                                               20

<210> SEQ ID NO 41
<211> LENGTH: 20
<212> TYPE: DNA
<213> ORGANISM: Artificial Sequence
<220> FEATURE:
<223> OTHER INFORMATION: Synthetic primer

<400> SEQUENCE: 41
caatctctgg attcggtggt                                               20

<210> SEQ ID NO 42
<211> LENGTH: 20
<212> TYPE: DNA
<213> ORGANISM: Artificial Sequence
<220> FEATURE:
<223> OTHER INFORMATION: Synthetic primer

<400> SEQUENCE: 42
tttcctgtag gggatcagga                                               20

<210> SEQ ID NO 43
<211> LENGTH: 22
<212> TYPE: DNA
<213> ORGANISM: Artificial Sequence
<220> FEATURE:
<223> OTHER INFORMATION: Synthetic primer
```

<400> SEQUENCE: 43
gcctggagaa actctgactc tg                                           22

<210> SEQ ID NO 44
<211> LENGTH: 20
<212> TYPE: DNA
<213> ORGANISM: Artificial Sequence
<220> FEATURE:
<223> OTHER INFORMATION: Synthetic primer

<400> SEQUENCE: 44
aaccaggaga gtcccattca                                              20

<210> SEQ ID NO 45
<211> LENGTH: 20
<212> TYPE: DNA
<213> ORGANISM: Artificial Sequence
<220> FEATURE:
<223> OTHER INFORMATION: Synthetic primer

<400> SEQUENCE: 45
ctggtatgta ccgcctctgg                                              20

<210> SEQ ID NO 46
<211> LENGTH: 21
<212> TYPE: DNA
<213> ORGANISM: Artificial Sequence
<220> FEATURE:
<223> OTHER INFORMATION: Synthetic primer

<400> SEQUENCE: 46
ctgtggtgaa aagaccagga g                                            21

<210> SEQ ID NO 47
<211> LENGTH: 20
<212> TYPE: DNA
<213> ORGANISM: Artificial Sequence
<220> FEATURE:
<223> OTHER INFORMATION: Synthetic primer

<400> SEQUENCE: 47
ctgaggcagt gaccatcaaa                                              20

<210> SEQ ID NO 48
<211> LENGTH: 20
<212> TYPE: DNA
<213> ORGANISM: Artificial Sequence
<220> FEATURE:
<223> OTHER INFORMATION: Synthetic primer

<400> SEQUENCE: 48
tccccTgcac agattaaagc                                              20

<210> SEQ ID NO 49
<211> LENGTH: 20
<212> TYPE: DNA
<213> ORGANISM: Artificial Sequence
<220> FEATURE:
<223> OTHER INFORMATION: Synthetic primer

<400> SEQUENCE: 49
tgcaggagtc agacactggt                                              20

```
<210> SEQ ID NO 50
<211> LENGTH: 190
<212> TYPE: DNA
<213> ORGANISM: Danio rerio

<400> SEQUENCE: 50
agagactctt caagcagcag cgtgactctg agtggacaga atatgcagac tgaggacaca      60
gctgtgtatt attgcgccag agagaatagc gggggccagt actttgacta ctggggaaa     120 ggaaccaaag tgacagtttc ctcagctcaa ccatctgcgc cccagtcagt cttcggtttg    180
tctcagtgca                                                           190

<210> SEQ ID NO 51
<211> LENGTH: 99
<212> TYPE: DNA
<213> ORGANISM: Danio rerio

<400> SEQUENCE: 51
gattcacagt tagcagagac tcttcaagca gcagcgtgac tctgagtgga cagaatatgc     60
agactgagga cacagctgtg tattattgcg ccagagagt                            99

<210> SEQ ID NO 52
<211> LENGTH: 106
<212> TYPE: DNA
<213> ORGANISM: Danio rerio

<400> SEQUENCE: 52
aatagcgggg gccagtactt tgactactgg gggaaaggaa ccaaagtgac agtttcctca     60
gctcaaccat ctgcgcccca gtcagtcttc ggtttgtctc agtgca                   106

<210> SEQ ID NO 53
<211> LENGTH: 51
<212> TYPE: DNA
<213> ORGANISM: Danio rerio

<400> SEQUENCE: 53
actactactt tgactactgg gggaaaggaa ccaaagtgac agtttcctca g               51

<210> SEQ ID NO 54
<211> LENGTH: 15
<212> TYPE: DNA
<213> ORGANISM: Danio rerio

<400> SEQUENCE: 54
aatagcgggg gccag                                                      15

<210> SEQ ID NO 55
<211> LENGTH: 11
<212> TYPE: DNA
<213> ORGANISM: Danio rerio

<400> SEQUENCE: 55
tatagcgggg g                                                          11

<210> SEQ ID NO 56
<211> LENGTH: 190
<212> TYPE: DNA
<213> ORGANISM: Danio rerio
```

```
<400> SEQUENCE: 56
agagattctt ccagcagcag cgtgactctg agtggacaga atatgcagag tgaggacaca      60
gctgtgtatt attgcgccag agagagcatg gagtggcgag cctttgatta ctggggaaag    120
ggaacaatgg tcactgtcac atcagctcaa ccatctgcgc cccagtcagt cttcggtttg    180
tctcagtgca                                                            190

<210> SEQ ID NO 57
<211> LENGTH: 190
<212> TYPE: DNA
<213> ORGANISM: Danio rerio

<400> SEQUENCE: 57
agagactctt ccagcagcag cgtgactctg agtggacaga atatgcagac tgaggacaca     60
gctgtgtatt attgcgccag agagagcatg gagtggcgag cctttgacta ctggggaaag   120
ggaacaatgg tcactgtcac atcagctcaa ccatctgcgc cccagtcagt cttcggtttg   180
tctcagtgca                                                           190

<210> SEQ ID NO 58
<211> LENGTH: 20
<212> TYPE: DNA
<213> ORGANISM: Artificial Sequence
<220> FEATURE:
<223> OTHER INFORMATION: Synthetic primer

<400> SEQUENCE: 58
gggaagtagt ccttgaccag                                                 20

<210> SEQ ID NO 59
<211> LENGTH: 18
<212> TYPE: DNA
<213> ORGANISM: Artificial Sequence
<220> FEATURE:
<223> OTHER INFORMATION: Synthetic primer

<400> SEQUENCE: 59
ggggaagaag ccctggac                                                   18

<210> SEQ ID NO 60
<211> LENGTH: 18
<212> TYPE: DNA
<213> ORGANISM: Artificial Sequence
<220> FEATURE:
<223> OTHER INFORMATION: Synthetic primer

<400> SEQUENCE: 60
ggccacgctg ctcgtatc                                                   18

<210> SEQ ID NO 61
<211> LENGTH: 20
<212> TYPE: DNA
<213> ORGANISM: Artificial Sequence
<220> FEATURE:
<223> OTHER INFORMATION: Synthetic primer

<400> SEQUENCE: 61
agggaatgtt tttgcagcag                                                 20

<210> SEQ ID NO 62
<211> LENGTH: 20
<212> TYPE: DNA
<213> ORGANISM: Artificial Sequence
```

<220> FEATURE:
<223> OTHER INFORMATION: Synthetic primer

<400> SEQUENCE: 62
ccacagggct gttatccttt                                               20

<210> SEQ ID NO 63
<211> LENGTH: 19
<212> TYPE: DNA
<213> ORGANISM: Artificial Sequence
<220> FEATURE:
<223> OTHER INFORMATION: Synthetic primer

<400> SEQUENCE: 63
cgcagaccct ctcactcac                                                19

<210> SEQ ID NO 64
<211> LENGTH: 20
<212> TYPE: DNA
<213> ORGANISM: Artificial Sequence
<220> FEATURE:
<223> OTHER INFORMATION: Synthetic primer

<400> SEQUENCE: 64
tggagctgag gtgaagaagc                                               20

<210> SEQ ID NO 65
<211> LENGTH: 20
<212> TYPE: DNA
<213> ORGANISM: Artificial Sequence
<220> FEATURE:
<223> OTHER INFORMATION: Synthetic primer

<400> SEQUENCE: 65
tgcaatctgg gtctgagttg                                               20

<210> SEQ ID NO 66
<211> LENGTH: 19
<212> TYPE: DNA
<213> ORGANISM: Artificial Sequence
<220> FEATURE:
<223> OTHER INFORMATION: Synthetic primer

<400> SEQUENCE: 66
ggctcaggac tggtgaagc                                                19

<210> SEQ ID NO 67
<211> LENGTH: 20
<212> TYPE: DNA
<213> ORGANISM: Artificial Sequence
<220> FEATURE:
<223> OTHER INFORMATION: Synthetic primer

<400> SEQUENCE: 67
tggagcagag gtgaaaaagc                                               20

<210> SEQ ID NO 68
<211> LENGTH: 19
<212> TYPE: DNA
<213> ORGANISM: Artificial Sequence
<220> FEATURE:
<223> OTHER INFORMATION: Synthetic primer

<400> SEQUENCE: 68
ggtgcagctg ttggagtct                                                19

```
<210> SEQ ID NO 69
<211> LENGTH: 20
<212> TYPE: DNA
<213> ORGANISM: Artificial Sequence
<220> FEATURE:
<223> OTHER INFORMATION: Synthetic primer

<400> SEQUENCE: 69
actgttgaag ccttcggaga                                              20

<210> SEQ ID NO 70
<211> LENGTH: 20
<212> TYPE: DNA
<213> ORGANISM: Artificial Sequence
<220> FEATURE:
<223> OTHER INFORMATION: Synthetic primer

<400> SEQUENCE: 70
aaacccacac agaccctcac                                              20

<210> SEQ ID NO 71
<211> LENGTH: 20
<212> TYPE: DNA
<213> ORGANISM: Artificial Sequence
<220> FEATURE:
<223> OTHER INFORMATION: Synthetic primer

<400> SEQUENCE: 71
agtctggggc tgaggtgaag                                              20

<210> SEQ ID NO 72
<211> LENGTH: 18
<212> TYPE: DNA
<213> ORGANISM: Artificial Sequence
<220> FEATURE:
<223> OTHER INFORMATION: Synthetic primer

<400> SEQUENCE: 72
ggcccaggac tggtgaag                                                18

<210> SEQ ID NO 73
<211> LENGTH: 18
<212> TYPE: DNA
<213> ORGANISM: Artificial Sequence
<220> FEATURE:
<223> OTHER INFORMATION: Synthetic primer

<400> SEQUENCE: 73
ggtgcagctg gtggagtc                                                18

<210> SEQ ID NO 74
<211> LENGTH: 18
<212> TYPE: DNA
<213> ORGANISM: Artificial Sequence
<220> FEATURE:
<223> OTHER INFORMATION: Synthetic primer

<400> SEQUENCE: 74
aagaccgatg ggcccttg                                                18

<210> SEQ ID NO 75
<211> LENGTH: 18
<212> TYPE: DNA
<213> ORGANISM: Artificial Sequence
<220> FEATURE:
<223> OTHER INFORMATION: Synthetic primer
```

<400> SEQUENCE: 75
gaagaccttg gggctggt                                                    18

<210> SEQ ID NO 76
<211> LENGTH: 20
<212> TYPE: DNA
<213> ORGANISM: Artificial Sequence
<220> FEATURE:
<223> OTHER INFORMATION: Synthetic primer

<400> SEQUENCE: 76
gggaattctc acaggagacg                                                  20

<210> SEQ ID NO 77
<211> LENGTH: 19
<212> TYPE: DNA
<213> ORGANISM: Artificial Sequence
<220> FEATURE:
<223> OTHER INFORMATION: Synthetic primer

<400> SEQUENCE: 77
gaagacggat gggctctgt                                                   19

<210> SEQ ID NO 78
<211> LENGTH: 19
<212> TYPE: DNA
<213> ORGANISM: Artificial Sequence
<220> FEATURE:
<223> OTHER INFORMATION: Synthetic primer

<400> SEQUENCE: 78
gggtgtctgc accctgata                                                   19

<210> SEQ ID NO 79
<211> LENGTH: 19
<212> TYPE: DNA
<213> ORGANISM: Artificial Sequence
<220> FEATURE:
<223> OTHER INFORMATION: Synthetic primer

<400> SEQUENCE: 79
ttcacaactg ggggactca                                                   19

<210> SEQ ID NO 80
<211> LENGTH: 19
<212> TYPE: DNA
<213> ORGANISM: Artificial Sequence
<220> FEATURE:
<223> OTHER INFORMATION: Synthetic primer

<400> SEQUENCE: 80
ctcacagctg ggggacact                                                   19

<210> SEQ ID NO 81
<211> LENGTH: 18
<212> TYPE: DNA
<213> ORGANISM: Artificial Sequence
<220> FEATURE:
<223> OTHER INFORMATION: Synthetic primer

<400> SEQUENCE: 81
actcacagct gggggatg                                                    18

```
<210> SEQ ID NO 82
<211> LENGTH: 20
<212> TYPE: DNA
<213> ORGANISM: Artificial Sequence
<220> FEATURE:
<223> OTHER INFORMATION: Synthetic primer

<400> SEQUENCE: 82
gcctcacaag tcgtggactc                                               20

<210> SEQ ID NO 83
<211> LENGTH: 20
<212> TYPE: DNA
<213> ORGANISM: Artificial Sequence
<220> FEATURE:
<223> OTHER INFORMATION: Synthetic primer

<400> SEQUENCE: 83
cagcctgcag actcagctac                                               20

<210> SEQ ID NO 84
<211> LENGTH: 20
<212> TYPE: DNA
<213> ORGANISM: Artificial Sequence
<220> FEATURE:
<223> OTHER INFORMATION: Synthetic primer

<400> SEQUENCE: 84
ggcagcagac actgcttctt                                               20

<210> SEQ ID NO 85
<211> LENGTH: 20
<212> TYPE: DNA
<213> ORGANISM: Artificial Sequence
<220> FEATURE:
<223> OTHER INFORMATION: Synthetic primer

<400> SEQUENCE: 85
gaccacagac tcaggcgttt                                               20

<210> SEQ ID NO 86
<211> LENGTH: 20
<212> TYPE: DNA
<213> ORGANISM: Artificial Sequence
<220> FEATURE:
<223> OTHER INFORMATION: Synthetic primer

<400> SEQUENCE: 86
gctcagtgat tcagccacct                                               20

<210> SEQ ID NO 87
<211> LENGTH: 20
<212> TYPE: DNA
<213> ORGANISM: Artificial Sequence
<220> FEATURE:
<223> OTHER INFORMATION: Synthetic primer

<400> SEQUENCE: 87
cccagtgatt cagccaccta                                               20

<210> SEQ ID NO 88
<211> LENGTH: 20
<212> TYPE: DNA
<213> ORGANISM: Artificial Sequence
<220> FEATURE:
<223> OTHER INFORMATION: Synthetic primer
```

<400> SEQUENCE: 88
ctcagcgatt cagcctccta                                               20

<210> SEQ ID NO 89
<211> LENGTH: 21
<212> TYPE: DNA
<213> ORGANISM: Artificial Sequence
<220> FEATURE:
<223> OTHER INFORMATION: Synthetic primer

<400> SEQUENCE: 89
tcccagctca gttactcagg a                                             21

<210> SEQ ID NO 90
<211> LENGTH: 18
<212> TYPE: DNA
<213> ORGANISM: Artificial Sequence
<220> FEATURE:
<223> OTHER INFORMATION: Synthetic primer

<400> SEQUENCE: 90
cagccatgca ggcatcta                                                 18

<210> SEQ ID NO 91
<211> LENGTH: 19
<212> TYPE: DNA
<213> ORGANISM: Artificial Sequence
<220> FEATURE:
<223> OTHER INFORMATION: Synthetic primer

<400> SEQUENCE: 91
gcccagcctg gtgatacag                                                19

<210> SEQ ID NO 92
<211> LENGTH: 24
<212> TYPE: DNA
<213> ORGANISM: Artificial Sequence
<220> FEATURE:
<223> OTHER INFORMATION: Synthetic primer

<400> SEQUENCE: 92
ccatacctag tgatgtaggc atct                                          24

<210> SEQ ID NO 93
<211> LENGTH: 19
<212> TYPE: DNA
<213> ORGANISM: Artificial Sequence
<220> FEATURE:
<223> OTHER INFORMATION: Synthetic primer

<400> SEQUENCE: 93
acatcacagc cacccagac                                                19

<210> SEQ ID NO 94
<211> LENGTH: 20
<212> TYPE: DNA
<213> ORGANISM: Artificial Sequence
<220> FEATURE:
<223> OTHER INFORMATION: Synthetic primer

<400> SEQUENCE: 94
caacctgaag actcggctgt                                               20

<210> SEQ ID NO 95
<211> LENGTH: 20
<212> TYPE: DNA
<213> ORGANISM: Artificial Sequence
<220> FEATURE:
<223> OTHER INFORMATION: Synthetic primer

<400> SEQUENCE: 95
ttgcagctac tcaacctgga                                              20

<210> SEQ ID NO 96
<211> LENGTH: 20
<212> TYPE: DNA
<213> ORGANISM: Artificial Sequence
<220> FEATURE:
<223> OTHER INFORMATION: Synthetic primer

<400> SEQUENCE: 96
ccagactggg gactcagcta                                              20

<210> SEQ ID NO 97
<211> LENGTH: 18
<212> TYPE: DNA
<213> ORGANISM: Artificial Sequence
<220> FEATURE:
<223> OTHER INFORMATION: Synthetic primer

<400> SEQUENCE: 97
cccagcctgg agactctg                                                18

<210> SEQ ID NO 98
<211> LENGTH: 18
<212> TYPE: DNA
<213> ORGANISM: Artificial Sequence
<220> FEATURE:
<223> OTHER INFORMATION: Synthetic primer

<400> SEQUENCE: 98
ccagcctgga gactcagc                                                18

<210> SEQ ID NO 99
<211> LENGTH: 19
<212> TYPE: DNA
<213> ORGANISM: Artificial Sequence
<220> FEATURE:
<223> OTHER INFORMATION: Synthetic primer

<400> SEQUENCE: 99
agcctcccat cccagagac                                               19

<210> SEQ ID NO 100
<211> LENGTH: 18
<212> TYPE: DNA
<213> ORGANISM: Artificial Sequence
<220> FEATURE:
<223> OTHER INFORMATION: Synthetic primer

<400> SEQUENCE: 100
ctgccgtgca tgacctct                                                18

<210> SEQ ID NO 101
<211> LENGTH: 19
<212> TYPE: DNA
<213> ORGANISM: Artificial Sequence
<220> FEATURE:
<223> OTHER INFORMATION: Synthetic primer

```
<400> SEQUENCE: 101
caaaggatcc cagcctgaa                                              19

<210> SEQ ID NO 102
<211> LENGTH: 20
<212> TYPE: DNA
<213> ORGANISM: Artificial Sequence
<220> FEATURE:
<223> OTHER INFORMATION: Synthetic primer

<400> SEQUENCE: 102
cacagcccct aaacctgaag                                             20

<210> SEQ ID NO 103
<211> LENGTH: 18
<212> TYPE: DNA
<213> ORGANISM: Artificial Sequence
<220> FEATURE:
<223> OTHER INFORMATION: Synthetic primer

<400> SEQUENCE: 103
ccgtgcagcc tgaagatt                                               18

<210> SEQ ID NO 104
<211> LENGTH: 20
<212> TYPE: DNA
<213> ORGANISM: Artificial Sequence
<220> FEATURE:
<223> OTHER INFORMATION: Synthetic primer

<400> SEQUENCE: 104
gcttctcagc ctggtgactc                                             20

<210> SEQ ID NO 105
<211> LENGTH: 21
<212> TYPE: DNA
<213> ORGANISM: Artificial Sequence
<220> FEATURE:
<223> OTHER INFORMATION: Synthetic primer

<400> SEQUENCE: 105
gctccagatg aaagactctg c                                           21

<210> SEQ ID NO 106
<211> LENGTH: 18
<212> TYPE: DNA
<213> ORGANISM: Artificial Sequence
<220> FEATURE:
<223> OTHER INFORMATION: Synthetic primer

<400> SEQUENCE: 106
ctgcccttgt gagcgact                                               18

<210> SEQ ID NO 107
<211> LENGTH: 17
<212> TYPE: DNA
<213> ORGANISM: Artificial Sequence
<220> FEATURE:
<223> OTHER INFORMATION: Synthetic primer

<400> SEQUENCE: 107
agcgacgcgg ctgagta                                                17
```

```
<210> SEQ ID NO 108
<211> LENGTH: 17
<212> TYPE: DNA
<213> ORGANISM: Artificial Sequence
<220> FEATURE:
<223> OTHER INFORMATION: Synthetic primer

<400> SEQUENCE: 108
accgacccgg ctgagta                                                  17

<210> SEQ ID NO 109
<211> LENGTH: 20
<212> TYPE: DNA
<213> ORGANISM: Artificial Sequence
<220> FEATURE:
<223> OTHER INFORMATION: Synthetic primer

<400> SEQUENCE: 109
tctgtgcatt ggagtgatgc                                               20

<210> SEQ ID NO 110
<211> LENGTH: 20
<212> TYPE: DNA
<213> ORGANISM: Artificial Sequence
<220> FEATURE:
<223> OTHER INFORMATION: Synthetic primer

<400> SEQUENCE: 110
gtgcagtgga gtgacacagc                                               20

<210> SEQ ID NO 111
<211> LENGTH: 23
<212> TYPE: DNA
<213> ORGANISM: Artificial Sequence
<220> FEATURE:
<223> OTHER INFORMATION: Synthetic primer

<400> SEQUENCE: 111
tcagttcaag tgtcagactc agc                                           23

<210> SEQ ID NO 112
<211> LENGTH: 24
<212> TYPE: DNA
<213> ORGANISM: Artificial Sequence
<220> FEATURE:
<223> OTHER INFORMATION: Synthetic primer

<400> SEQUENCE: 112
gaaagactca gttcaagagt caga                                          24

<210> SEQ ID NO 113
<211> LENGTH: 22
<212> TYPE: DNA
<213> ORGANISM: Artificial Sequence
<220> FEATURE:
<223> OTHER INFORMATION: Synthetic primer

<400> SEQUENCE: 113
cagtccaggt atcagactca gc                                            22

<210> SEQ ID NO 114
<211> LENGTH: 18
<212> TYPE: DNA
<213> ORGANISM: Artificial Sequence
<220> FEATURE:
<223> OTHER INFORMATION: Synthetic primer
```

```
<400> SEQUENCE: 114
ggtgcagctg tcggactc                                              18

<210> SEQ ID NO 115
<211> LENGTH: 21
<212> TYPE: DNA
<213> ORGANISM: Artificial Sequence
<220> FEATURE:
<223> OTHER INFORMATION: Synthetic primer

<400> SEQUENCE: 115
tgctcaagag gaagactcag c                                          21

<210> SEQ ID NO 116
<211> LENGTH: 18
<212> TYPE: DNA
<213> ORGANISM: Artificial Sequence
<220> FEATURE:
<223> OTHER INFORMATION: Synthetic primer

<400> SEQUENCE: 116
ggaggcagat gctgctgt                                              18

<210> SEQ ID NO 117
<211> LENGTH: 19
<212> TYPE: DNA
<213> ORGANISM: Artificial Sequence
<220> FEATURE:
<223> OTHER INFORMATION: Synthetic primer

<400> SEQUENCE: 117
ccacgctacg ctgagagac                                             19

<210> SEQ ID NO 118
<211> LENGTH: 21
<212> TYPE: DNA
<213> ORGANISM: Artificial Sequence
<220> FEATURE:
<223> OTHER INFORMATION: Synthetic primer

<400> SEQUENCE: 118
cgtgctacct tgagagatgc t                                          21

<210> SEQ ID NO 119
<211> LENGTH: 18
<212> TYPE: DNA
<213> ORGANISM: Artificial Sequence
<220> FEATURE:
<223> OTHER INFORMATION: Synthetic primer

<400> SEQUENCE: 119
tccctgagcg acactgct                                              18

<210> SEQ ID NO 120
<211> LENGTH: 20
<212> TYPE: DNA
<213> ORGANISM: Artificial Sequence
<220> FEATURE:
<223> OTHER INFORMATION: Synthetic primer

<400> SEQUENCE: 120
caacccatgt gagtgatgct                                            20
```

-continued

```
<210> SEQ ID NO 121
<211> LENGTH: 20
<212> TYPE: DNA
<213> ORGANISM: Artificial Sequence
<220> FEATURE:
<223> OTHER INFORMATION: Synthetic primer

<400> SEQUENCE: 121
cagatctcag ctggaccaca                                                   20

<210> SEQ ID NO 122
<211> LENGTH: 21
<212> TYPE: DNA
<213> ORGANISM: Artificial Sequence
<220> FEATURE:
<223> OTHER INFORMATION: Synthetic primer

<400> SEQUENCE: 122
gcactgttgc tcttgaagtc c                                                 21

<210> SEQ ID NO 123
<211> LENGTH: 20
<212> TYPE: DNA
<213> ORGANISM: Artificial Sequence
<220> FEATURE:
<223> OTHER INFORMATION: Synthetic primer

<400> SEQUENCE: 123
gattaaaccc ggccactttc                                                   20

<210> SEQ ID NO 124
<211> LENGTH: 18
<212> TYPE: DNA
<213> ORGANISM: Artificial Sequence
<220> FEATURE:
<223> OTHER INFORMATION: Synthetic primer

<400> SEQUENCE: 124
ggggactcgg ccatgtat                                                     18

<210> SEQ ID NO 125
<211> LENGTH: 19
<212> TYPE: DNA
<213> ORGANISM: Artificial Sequence
<220> FEATURE:
<223> OTHER INFORMATION: Synthetic primer

<400> SEQUENCE: 125
gggggactca gccgtgtat                                                    19

<210> SEQ ID NO 126
<211> LENGTH: 18
<212> TYPE: DNA
<213> ORGANISM: Artificial Sequence
<220> FEATURE:
<223> OTHER INFORMATION: Synthetic primer

<400> SEQUENCE: 126
gggggacaca gccatgta                                                     18

<210> SEQ ID NO 127
<211> LENGTH: 19
<212> TYPE: DNA
<213> ORGANISM: Artificial Sequence
<220> FEATURE:
<223> OTHER INFORMATION: Synthetic primer
```

<400> SEQUENCE: 127
gaggactccg ccgtgtatc                                               19

<210> SEQ ID NO 128
<211> LENGTH: 19
<212> TYPE: DNA
<213> ORGANISM: Artificial Sequence
<220> FEATURE:
<223> OTHER INFORMATION: Synthetic primer

<400> SEQUENCE: 128
gcgggactca gccatgtat                                               19

<210> SEQ ID NO 129
<211> LENGTH: 18
<212> TYPE: DNA
<213> ORGANISM: Artificial Sequence
<220> FEATURE:
<223> OTHER INFORMATION: Synthetic primer

<400> SEQUENCE: 129
ggactcggcc gtgtatct                                                18

<210> SEQ ID NO 130
<211> LENGTH: 18
<212> TYPE: DNA
<213> ORGANISM: Artificial Sequence
<220> FEATURE:
<223> OTHER INFORMATION: Synthetic primer

<400> SEQUENCE: 130
agaacccagg gactcagc                                                18

<210> SEQ ID NO 131
<211> LENGTH: 19
<212> TYPE: DNA
<213> ORGANISM: Artificial Sequence
<220> FEATURE:
<223> OTHER INFORMATION: Synthetic primer

<400> SEQUENCE: 131
ctggaggact cagccatgt                                               19

<210> SEQ ID NO 132
<211> LENGTH: 24
<212> TYPE: DNA
<213> ORGANISM: Artificial Sequence
<220> FEATURE:
<223> OTHER INFORMATION: Synthetic primer

<400> SEQUENCE: 132
ctggaggatt ctggagttta tttc                                         24

<210> SEQ ID NO 133
<211> LENGTH: 21
<212> TYPE: DNA
<213> ORGANISM: Artificial Sequence
<220> FEATURE:
<223> OTHER INFORMATION: Synthetic primer

<400> SEQUENCE: 133
aggagattcg gcagcttatt t                                            21

```
<210> SEQ ID NO 134
<211> LENGTH: 20
<212> TYPE: DNA
<213> ORGANISM: Artificial Sequence
<220> FEATURE:
<223> OTHER INFORMATION: Synthetic primer

<400> SEQUENCE: 134
gcttgaggat tcagcagtgt                                               20

<210> SEQ ID NO 135
<211> LENGTH: 23
<212> TYPE: DNA
<213> ORGANISM: Artificial Sequence
<220> FEATURE:
<223> OTHER INFORMATION: Synthetic primer

<400> SEQUENCE: 135
ttggtgactc tgctgtgtat ttc                                           23

<210> SEQ ID NO 136
<211> LENGTH: 20
<212> TYPE: DNA
<213> ORGANISM: Artificial Sequence
<220> FEATURE:
<223> OTHER INFORMATION: Synthetic primer

<400> SEQUENCE: 136
agaagactcg gccctgtatc                                               20

<210> SEQ ID NO 137
<211> LENGTH: 19
<212> TYPE: DNA
<213> ORGANISM: Artificial Sequence
<220> FEATURE:
<223> OTHER INFORMATION: Synthetic primer

<400> SEQUENCE: 137 gggggactcag ccctgtact                                               19

<210> SEQ ID NO 138
<211> LENGTH: 21
<212> TYPE: DNA
<213> ORGANISM: Artificial Sequence
<220> FEATURE:
<223> OTHER INFORMATION: Synthetic primer

<400> SEQUENCE: 138
gggggactca gctttgtatt t                                             21

<210> SEQ ID NO 139
<211> LENGTH: 16
<212> TYPE: DNA
<213> ORGANISM: Artificial Sequence
<220> FEATURE:
<223> OTHER INFORMATION: Synthetic primer

<400> SEQUENCE: 139
ggggactcgg cccttt                                                   16

<210> SEQ ID NO 140
<211> LENGTH: 19
<212> TYPE: DNA
<213> ORGANISM: Artificial Sequence
<220> FEATURE:
<223> OTHER INFORMATION: Synthetic primer
```

```
<400> SEQUENCE: 140
gacgactcgg ccctgtatc                                              19

<210> SEQ ID NO 141
<211> LENGTH: 19
<212> TYPE: DNA
<213> ORGANISM: Artificial Sequence
<220> FEATURE:
<223> OTHER INFORMATION: Synthetic primer

<400> SEQUENCE: 141
ggactcggcc ctgtatctc                                              19

<210> SEQ ID NO 142
<211> LENGTH: 23
<212> TYPE: DNA
<213> ORGANISM: Artificial Sequence
<220> FEATURE:
<223> OTHER INFORMATION: Synthetic primer

<400> SEQUENCE: 142
tcagtgactc tggcttctat ctc                                         23

<210> SEQ ID NO 143
<211> LENGTH: 20
<212> TYPE: DNA
<213> ORGANISM: Artificial Sequence
<220> FEATURE:
<223> OTHER INFORMATION: Synthetic primer

<400> SEQUENCE: 143
cctcctccca gacatctgta                                             20

<210> SEQ ID NO 144
<211> LENGTH: 21
<212> TYPE: DNA
<213> ORGANISM: Artificial Sequence
<220> FEATURE:
<223> OTHER INFORMATION: Synthetic primer

<400> SEQUENCE: 144
cgctcccaga catctgtgta t                                           21

<210> SEQ ID NO 145
<211> LENGTH: 20
<212> TYPE: DNA
<213> ORGANISM: Artificial Sequence
<220> FEATURE:
<223> OTHER INFORMATION: Synthetic primer

<400> SEQUENCE: 145
gctaccagct cccagacatc                                             20

<210> SEQ ID NO 146
<211> LENGTH: 23
<212> TYPE: DNA
<213> ORGANISM: Artificial Sequence
<220> FEATURE:
<223> OTHER INFORMATION: Synthetic primer

<400> SEQUENCE: 146
ccctctcaga catctgtgta ctt                                         23
```

```
<210> SEQ ID NO 147
<211> LENGTH: 20
<212> TYPE: DNA
<213> ORGANISM: Artificial Sequence
<220> FEATURE:
<223> OTHER INFORMATION: Synthetic primer

<400> SEQUENCE: 147
ccctcccaaa catctgtgta                                              20

<210> SEQ ID NO 148
<211> LENGTH: 22
<212> TYPE: DNA
<213> ORGANISM: Artificial Sequence
<220> FEATURE:
<223> OTHER INFORMATION: Synthetic primer

<400> SEQUENCE: 148
cctcccagac atctgtgtac tt                                           22

<210> SEQ ID NO 149
<211> LENGTH: 23
<212> TYPE: DNA
<213> ORGANISM: Artificial Sequence
<220> FEATURE:
<223> OTHER INFORMATION: Synthetic primer

<400> SEQUENCE: 149
ccctcccaga catctgtata ctt                                          23

<210> SEQ ID NO 150
<211> LENGTH: 19
<212> TYPE: DNA
<213> ORGANISM: Artificial Sequence
<220> FEATURE:
<223> OTHER INFORMATION: Synthetic primer

<400> SEQUENCE: 150
cccaaccaga cctctctgt                                               19

<210> SEQ ID NO 151
<211> LENGTH: 24
<212> TYPE: DNA
<213> ORGANISM: Artificial Sequence
<220> FEATURE:
<223> OTHER INFORMATION: Synthetic primer

<400> SEQUENCE: 151
ccaaccagac atctatgtac ctct                                         24

<210> SEQ ID NO 152
<211> LENGTH: 22
<212> TYPE: DNA
<213> ORGANISM: Artificial Sequence
<220> FEATURE:
<223> OTHER INFORMATION: Synthetic primer

<400> SEQUENCE: 152
ccctcacata cctctcagta cc                                           22

<210> SEQ ID NO 153
<211> LENGTH: 21
<212> TYPE: DNA
<213> ORGANISM: Artificial Sequence
<220> FEATURE:
<223> OTHER INFORMATION: Synthetic primer
```

<400> SEQUENCE: 153
cccaaccaga cagctcttta c                                        21

<210> SEQ ID NO 154
<211> LENGTH: 22
<212> TYPE: DNA
<213> ORGANISM: Artificial Sequence
<220> FEATURE:
<223> OTHER INFORMATION: Synthetic primer

<400> SEQUENCE: 154
gaacccgaca gctttctatc tc                                       22

<210> SEQ ID NO 155
<211> LENGTH: 19
<212> TYPE: DNA
<213> ORGANISM: Artificial Sequence
<220> FEATURE:
<223> OTHER INFORMATION: Synthetic primer

<400> SEQUENCE: 155
tgcccatcct gaagacagc                                           19

<210> SEQ ID NO 156
<211> LENGTH: 19
<212> TYPE: DNA
<213> ORGANISM: Artificial Sequence
<220> FEATURE:
<223> OTHER INFORMATION: Synthetic primer

<400> SEQUENCE: 156
catgagccct gaagacagc                                           19

<210> SEQ ID NO 157
<211> LENGTH: 18
<212> TYPE: DNA
<213> ORGANISM: Artificial Sequence
<220> FEATURE:
<223> OTHER INFORMATION: Synthetic primer

<400> SEQUENCE: 157
ctcggaaccg ggagacac                                            18

<210> SEQ ID NO 158
<211> LENGTH: 18
<212> TYPE: DNA
<213> ORGANISM: Artificial Sequence
<220> FEATURE:
<223> OTHER INFORMATION: Synthetic primer

<400> SEQUENCE: 158
cagagccgag ggactcag                                            18

<210> SEQ ID NO 159
<211> LENGTH: 19
<212> TYPE: DNA
<213> ORGANISM: Artificial Sequence
<220> FEATURE:
<223> OTHER INFORMATION: Synthetic primer

<400> SEQUENCE: 159
gggggacttg gctgtgtat                                           19

```
<210> SEQ ID NO 160
<211> LENGTH: 25
<212> TYPE: DNA
<213> ORGANISM: Artificial Sequence
<220> FEATURE:
<223> OTHER INFORMATION: Synthetic primer

<400> SEQUENCE: 160
ccagacagct tctaggttac ttcag                                              25

<210> SEQ ID NO 161
<211> LENGTH: 22
<212> TYPE: DNA
<213> ORGANISM: Artificial Sequence
<220> FEATURE:
<223> OTHER INFORMATION: Synthetic primer

<400> SEQUENCE: 161
gctccctctc agacttctgt tt                                                 22

<210> SEQ ID NO 162
<211> LENGTH: 20
<212> TYPE: DNA
<213> ORGANISM: Artificial Sequence
<220> FEATURE:
<223> OTHER INFORMATION: Synthetic primer

<400> SEQUENCE: 162
caggagacct gaagacagca                                                    20

<210> SEQ ID NO 163
<211> LENGTH: 20
<212> TYPE: DNA
<213> ORGANISM: Artificial Sequence
<220> FEATURE:
<223> OTHER INFORMATION: Synthetic primer

<400> SEQUENCE: 163
tcatagagga tggtggcaga                                                    20

<210> SEQ ID NO 164
<211> LENGTH: 19
<212> TYPE: DNA
<213> ORGANISM: Artificial Sequence
<220> FEATURE:
<223> OTHER INFORMATION: Synthetic primer

<400> SEQUENCE: 164
cacctccttc ccattcacc                                                     19

<210> SEQ ID NO 165
<211> LENGTH: 20
<212> TYPE: DNA
<213> ORGANISM: Artificial Sequence
<220> FEATURE:
<223> OTHER INFORMATION: Synthetic primer

<400> SEQUENCE: 165
agccacagtc tgctctaccc                                                    20
```